(12) United States Patent
Allen et al.

(10) Patent No.: US 9,359,474 B2
(45) Date of Patent: Jun. 7, 2016

(54) CATALYSTS AND METHODS FOR POLYMER SYNTHESIS

(71) Applicant: Novomer, Inc., Ithaca, NY (US)

(72) Inventors: Scott D. Allen, Ithaca, NY (US); Gabriel Job, Ithaca, NY (US); Jay J. Farmer, Ithaca, NY (US)

(73) Assignee: Novomer, Inc., Ithaca, NY (US)

( * ) Notice: Subject to any disclaimer, the term of this patent is extended or adjusted under 35 U.S.C. 154(b) by 0 days.

(21) Appl. No.: 14/355,334

(22) PCT Filed: Nov. 3, 2012

(86) PCT No.: PCT/US2012/063462
§ 371 (c)(1),
(2) Date: Apr. 30, 2014

(87) PCT Pub. No.: WO2013/067460
PCT Pub. Date: May 10, 2013

(65) Prior Publication Data
US 2014/0343246 A1 Nov. 20, 2014

Related U.S. Application Data

(60) Provisional application No. 61/555,924, filed on Nov. 4, 2011.

(51) Int. Cl.
C08G 65/04 (2006.01)
C08G 64/34 (2006.01)
C09B 57/10 (2006.01)

(52) U.S. Cl.
CPC ............... *C08G 64/34* (2013.01); *C09B 57/10* (2013.01)

(58) Field of Classification Search
CPC ................................ C08G 64/34; C09B 57/10
USPC ........................... 570/183, 187; 528/409, 412
See application file for complete search history.

(56) References Cited

U.S. PATENT DOCUMENTS

| 6,870,004 | B1 | 3/2005 | Nguyen et al. |
| 7,304,172 | B2 | 12/2007 | Coates et al. |
| 7,399,822 | B2 | 7/2008 | Coates et al. |
| 8,247,520 | B2 | 8/2012 | Allen et al. |
| 8,470,956 | B2 | 6/2013 | Allen et al. |
| 8,604,155 | B2 | 12/2013 | Allen et al. |
| 8,633,123 | B2 | 1/2014 | Allen et al. |
| 8,921,508 | B2 | 12/2014 | Allen et al. |
| 8,946,109 | B2 | 2/2015 | Allen et al. |
| 8,951,930 | B2 | 2/2015 | Allen et al. |
| 8,956,989 | B2 | 2/2015 | Allen et al. |
| 2010/0121026 | A1 | 5/2010 | Lee et al. |
| 2010/0323201 | A1 | 12/2010 | Son et al. |
| 2011/0152497 | A1* | 6/2011 | Allen et al. ............ 528/405 |
| 2011/0201779 | A1* | 8/2011 | Cherian et al. ........ 528/405 |
| 2011/0230580 | A1 | 9/2011 | Allen et al. |
| 2013/0144033 | A1* | 6/2013 | Allen et al. ............ 528/405 |
| 2014/0228538 | A1 | 8/2014 | Allen et al. |
| 2014/0296522 | A1 | 10/2014 | Lee et al. |
| 2014/0336354 | A1 | 11/2014 | Job et al. |
| 2015/0232496 | A1 | 8/2015 | Job et al. |
| 2015/0252145 | A1 | 9/2015 | Allen et al. |

FOREIGN PATENT DOCUMENTS

| WO | WO-2008/136591 A1 | 11/2008 |
| WO | WO-2010/013948 A2 | 2/2010 |
| WO | WO-2010/022388 A2 | 2/2010 |
| WO | WO-2010/028362 A1 | 3/2010 |
| WO | WO-2011/105846 A2 | 9/2011 |
| WO | WO-2011/163133 A1 | 12/2011 |
| WO | WO-2012/158573 A1 | 11/2012 |
| WO | WO-2013/012895 A1 | 1/2013 |
| WO | WO-2013/067460 A1 | 5/2013 |
| WO | WO-2013/090276 A1 | 6/2013 |
| WO | WO-2014/031811 A1 | 2/2014 |

OTHER PUBLICATIONS

International Search Report of PCT/US12/63462, 3 pages (mailed Jan. 17, 2013).
Written Opinion of PCT/US12/63462, 9 pages (mailed Jan. 17, 2013).
Sujith, S.S. et al., A Highly Active and Recyclable Catalytic System for CO2/Propylene Oxide Copolymerization, Angew. Chem. Intl. Ed., 47(38): 7306-7309 (2008).

\* cited by examiner

*Primary Examiner* — Shane Fang
(74) *Attorney, Agent, or Firm* — Choate, Hall & Stewart, LLP; Charles E. Lyon; John P. Rearick

(57) ABSTRACT

The present invention provides unimolecular metal complexes having increased activity in the copolymerization of carbon dioxide and epoxides. Also provided are methods of using such metal complexes in the synthesis of polymers. According to one aspect, the present invention provides metal complexes comprising an activating species with co-catalytic activity tethered to a multidentate ligand that is coordinated to the active metal center of the complex.

14 Claims, No Drawings

CATALYSTS AND METHODS FOR POLYMER SYNTHESIS

CROSS REFERENCE TO RELATED APPLICATIONS

The present application claims priority to U.S. provisional patent application Ser. No. 61/555,924, filed Nov. 4, 2011, the entire contents of which are hereby incorporated herein by reference.

BACKGROUND

Catalysts capable of effecting the copolymerization of epoxides and carbon dioxide to form aliphatic polycarbonates (APCs) have been known in the art since the 1960s. The early catalysts were based on heterogeneous zinc compounds and suffered from low reactivity, a lack of selectivity for polymer formation vs. cyclic carbonate formation, and a tendency to produce polycarbonates contaminated with ether linkages.

Improved catalysts based on transition metals have been discovered over the past decade or so. These newer catalysts have increased reactivity and improved selectivity. Nevertheless, even using highly active catalysts such as those disclosed in U.S. Pat. No. 7,304,172, the reaction times required to make high molecular weight polymer are typically quite long. In addition, the best-performing catalysts disclosed in the '172 patent require the addition of a separate co-catalyst to achieve optimum activity Attempts to improve these transition metal catalysts have been made. Catalysts described by Lee and co-workers (WO2008/136591 and Sujith et al., Angew Chem. Int'l. Ed., 120, 7416-7419, 2008) use the approach of tethering co-catalyst moieties directly to the metal ligand and in some cases result in high catalysis rates.

These next-generation catalytic systems suffer from lengthy and complicated syntheses and are therefore expensive. Attempts have been made to recycle these catalysts and their precursors to lower costs over time, but there remains a need for less expensive catalysts with high activity for epoxide $CO_2$ copolymerization.

SUMMARY

As noted above, catalysts described by Lee and co-workers (WO2008/136591 and Angew Chem. Int'l. Ed. 2008) use the approach of tethering co-catalyst moieties directly to the metal ligand and in some cases result in high catalysis rates. These catalysts take the general form:

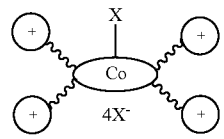

where each

moiety represents a tethered cationic group that presumably acts as a cocatalyst for the polymerization reaction. The preferred catalysts in WO2008/136591 ("the '591 PCT publication") have a total of four such moieties and the ligands are symmetrical in the sense that each aryl ring of the salen ligand has the same substitution pattern, with each aryl ring bearing a substituent having two cationic moieties in the preferred species.

The '591 PCT publication also presents examples of catalysts where only one aryl ring of the salen ligand bears a substituent having a cationic substituent. However, the results demonstrate that these catalysts are not as active as the bis-substituted versions. For example, comparing Example Nos. 9 and 12 from the table on pg. 49 of the '591 PCT publication shows reaction data for catalysts 5 and 7 as depicted below:

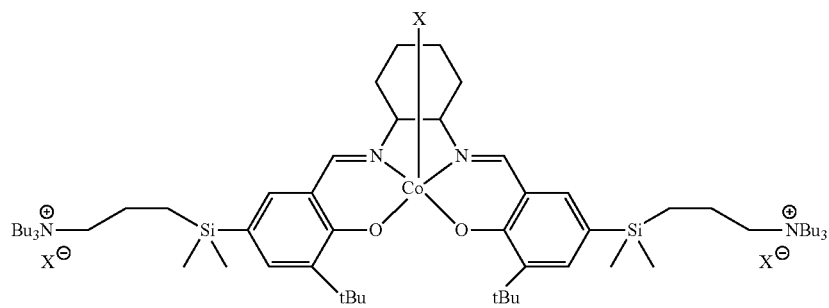

(X = 2,4-dinitrophenolate)

5

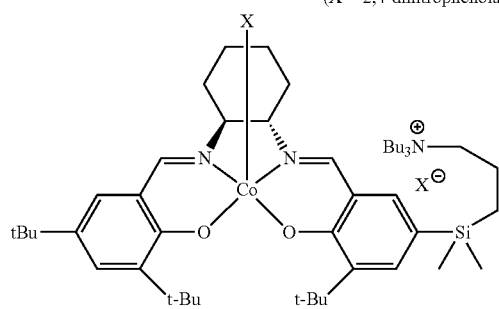

(X = 2,4-dinitrophenolate)

7

Catalyst 5 is shown in Ex. No. 9 to have a turnover frequency of 3330 h$^{-1}$, and provides a selectivity of 94%. Under identical reaction conditions, catalyst 7 in Ex. No. 12 shows a turnover frequency of only 1500 h$^{-1}$ and a lower selectivity of 89%.

Among other things, the present invention encompasses the recognition that, unexpectedly, and contrary to what would be expected based on the data presented in the '591 PCT publication, metal complexes having two or more tethered cationic groups present on one aryl ring of the ligand, and no such cationic groups on the other aryl ring demonstrate catalytic activity comparable to the known analogs where both aryl rings are substituted with cationic groups.

These compounds have several advantages, including but not limited to one or more of the following: they can be less expensive to produce, they have a lower molecular weight and less catalyst mass is needed for polymerizations, and/or they are more easily handled, characterized, and recycled due to the fact that they have fewer counterions present.

In certain embodiments, the provided metal complexes comprise a salen ligand derived from two different salicylaldehyde precursors. In certain embodiments, one salicaldehyde precursor is characterized in that it comprises two or more cationic functional groups and the other salicylaldehyde precursor is characterized in that it comprises no cationic functional groups.

In certain embodiments, the present invention encompasses metal complexes having a structure:

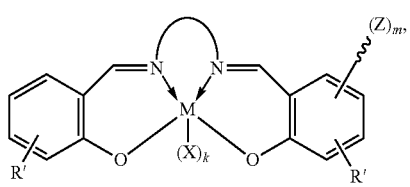

I where the substituents and variables are as defined below and described in the examples and embodiments herein.

In another aspect, the present invention encompasses methods of using these metal complexes to catalyze the copolymerization of epoxides and carbon dioxide to form aliphatic polycarbonates.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Certain compounds of the present invention can comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the invention are enantiopure compounds. In certain embodiments, mixtures of enantiomers or diastereomers are provided.

Furthermore, certain compounds, as described herein may have one or more double bonds that can exist as either a Z or E isomer, unless otherwise indicated. The invention additionally encompasses the compounds as individual isomers substantially free of other isomers and alternatively, as mixtures of various isomers, e.g., racemic mixtures of enantiomers. In addition to the above-mentioned compounds per se, this invention also encompasses compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a compound may, in some embodiments, be provided substantially free of one or more corresponding stereoisomers, and may also be referred to as "stereochemically enriched."

Where a particular enantiomer is preferred, it may, in some embodiments be provided substantially free of the opposite enantiomer, and may also be referred to as "optically enriched." "Optically enriched," as used herein, means that the compound is made up of a significantly greater proportion of one enantiomer. In certain embodiments the compound is made up of at least about 90% by weight of an enantiomer. In some embodiments the compound is made up of at least about 95%, 97%, 98%, 99%, 99.5%, 99.7%, 99.8%, or 99.9% by weight of an enantiomer. In some embodiments the enantiomeric excess of provided compounds is at least about 90%, 95%, 97%, 98%, 99%, 99.5%, 99.7%, 99.8%, or 99.9%. In some embodiments, enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and Spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl. In certain embodiments, the term aliphatic group encompasses aliphatic groups wherein one or more hydrogen atoms are replaced with a halogen atom. In certain embodiments, the term aliphatic group encompasses chlorinated or fluorinated aliphatic groups including perfluorinated compounds.

The term "epoxide", as used herein, refers to a substituted or unsubstituted oxirane. Such substituted oxiranes include monosubstituted oxiranes, disubstituted oxiranes, trisubstituted oxiranes, and tetrasubstituted oxiranes. Such epoxides may be further optionally substituted as defined herein. In certain embodiments, epoxides comprise a single oxirane moiety. In certain embodiments, epoxides comprise two or more oxirane moieties.

The term "polymer", as used herein, refers to a molecule of high relative molecular mass, the structure of which comprises the multiple repetition of units derived, actually or conceptually, from molecules of low relative molecular mass. In certain embodiments, a polymer is comprised of only one monomer species (e.g., polyethylene oxide). In certain embodiments, a polymer of the present invention is a copolymer, terpolymer, heteropolymer, block copolymer, or tapered heteropolymer of one or more epoxides.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic groups is bicyclic. In some embodiments, a carbocyclic group is tricyclic. In some embodiments, a carbocyclic group is polycyclic.

The term "alkyl," as used herein, refers to saturated, straight- or branched-chain hydrocarbon radicals derived by removal of a single hydrogen atom from an aliphatic moiety. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in yet other embodiments alkyl groups contain 1-3 carbon atoms, and in yet other embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived by the removal of a single hydrogen atom from a straight- or branched-chain aliphatic moiety having at least one carbon-carbon double bond. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms, in some embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, allyl, 1,3-butadienyl, butenyl, 1-methyl-2-buten-1-yl, allyl, 1,3-butadienyl, allenyl, and the like.

The term "alkynyl," as used herein, refers to a monovalent group derived by the removal of a single hydrogen atom from a straight- or branched-chain aliphatic moiety having at least one carbon-carbon triple bond. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, but are not limited to, ethynyl, 2-propynyl (propargyl), 1-propynyl, and the like.

The term "carbocycle" and "carbocyclic ring" as used herein, refer to monocyclic and polycyclic moieties wherein the rings contain only carbon atoms. Unless otherwise specified, carbocycles may be saturated, partially unsaturated or aromatic, and contain 3 to 20 carbon atoms. Representative carbocyles include cyclopropane, cyclobutane, cyclopentane, cyclohexane, bicyclo[2,2,1]heptane, norbornene, phenyl, cyclohexene, naphthalene, and spiro[4.5]decane, to name but a few.

The term "aryl" used alone or as part of a larger moiety as in "aralkyl", "aralkoxy", or "aryloxyalkyl", refers to monocyclic and polycyclic ring systems having a total of six to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like.

The term "heteroaliphatic," as used herein, refers to aliphatic groups wherein one or more carbon atoms are independently replaced by one or more atoms selected from the group consisting of oxygen, sulfur, nitrogen, phosphorus, or boron. In certain embodiments, one to six carbon atoms are independently replaced by one or more of oxygen, sulfur, nitrogen, or phosphorus. Heteroaliphatic groups may be substituted or unsubstituted, branched or unbranched, cyclic or acyclic, and include saturated, unsaturated or partially unsaturated groups.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono- or polycyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-14-membered bicyclic heterocyclic moiety that is saturated, partially unsaturated, or aromatic and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

The term "acyl" as used herein refers to a group having a formula —C(O)R where R is hydrogen or an optionally substituted aliphatic, aryl, or heterocyclic group.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. In preferred embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy) methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl(CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxany lidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethylcarbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzylcarbamate, 1,1-dimethyl-3-(N,N-dimethylcarboxamido)propylcarbamate, 1,1-dimethylpropynylcarbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzylcarbamate, 1-methylcyclobutylcarbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fern), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protecting Groups in Organic Synthesis*, T. W. Greene and P. G. M. Wuts, 3$^{rd}$ edition, John Wiley & Sons, 1999, the entirety of which is incorporated herein by reference.

When substituents are described herein, the term "radical" or "optionally substituted radical" is sometimes used. In this context, "radical" means a moiety or functional group having an available position for attachment to the structure on which the substituent is bound. In general the point of attachment would bear a hydrogen atom if the substituent were an independent neutral molecule rather than a substituent. The terms "radical" or "optionally-substituted radical" in this context are thus interchangeable with "group" or "optionally-substituted group".

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted group" or "optionally substituted radical" may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

In some chemical structures herein, substituents are shown attached to a bond that crosses a bond in a ring of the depicted molecule. This convention indicates that one or more of the substituents may be attached to the ring at any available position (usually in place of a hydrogen atom of the parent structure). In cases where an atom of a ring so substituted has two substitutable positions, two groups may be present on the same ring atom. Unless otherwise indicated, when more than one substituent is present, each is defined independently of the others, and each may have a different structure. In cases where the substituent shown crossing a bond of the ring is —R, this has the same meaning as if the ring were said to be "optionally substituted" as described in the preceding paragraph.

Suitable monovalent substituents on a substitutable carbon atom of an "optionally substituted" group are independently halogen; —(CH$_2$)$_{0-4}$R°; —(CH$_2$)$_{0-4}$OR°; —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)N(R°)$_2$; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched)alkylene)C(O)O—N(R°)$_2$, wherein each R° may be substituted as defined below and is independently hydrogen, C$_{1-8}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3- to 12-membered saturated, partially unsaturated, or aryl mono- or polycyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, (CH$_2$)$_{0-2}$R•, (haloR•), —(CH$_2$)$_{0-2}$OH, —(CH$_2$)$_{0-2}$R•, —(CH$_2$)$_{0-2}$CH(OR•)$_2$; —O(haloR•), —CN, —N$_3$, —(CH$_2$)$_{0-2}$C(O)R•, —(CH$_2$)$_{0-2}$C(O)OH, —(CH$_2$)$_{0-2}$C(O)OR•, —(CH$_2$)$_{0-4}$C(O)N(R°)$_2$; —(CH$_2$)$_{0-2}$SR•, —(CH$_2$)$_{0-2}$SH, —(CH$_2$)$_{0-2}$NH$_2$, —(CH$_2$)$_{0-2}$NHR•, —(CH$_2$)$_{0-2}$NR•$_2$, —NO$_2$, —SiR•$_3$, —OSiR•$_3$, —C(O)SR•, (C$_{1-4}$ straight or branched alkylene)C(O)OR•, or —SSR• wherein each R• is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5- to 6-membered saturated, partially unsaturated, or aryl ring having 0-4 heteroatoms independently selected from nitrogen, oxygen, or sulfur.

Suitable substituents on the aliphatic group of R* include halogen, —R*, -(haloR*), —OH, —OR*, —O(haloR*), —CN, —C(O)OH, —C(O)OR*, —NH$_2$, —NHR*, —NR*$_2$, or —NO$_2$, wherein each R* is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5- to 6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3- to 12-membered saturated, partially unsaturated, or aryl mono- or bicyclic ring having 0-4 heteroatoms independently selected from nitrogen, oxygen, or sulfur. A substitutable nitrogen may be substituted with three R$^†$ substituents to provide a charged ammonium moiety —N$^+$(R$^†$)$_3$, wherein the ammonium moiety is further complexed witth a suitable counterion.

Suitable substituents on the aliphatic group of Rt are independently halogen, —R$^∀$, (haloR$^∀$), —OH, —OR$^∀$, —O(haloR$^∀$), —CN, —C(O)OH, —C(O)OR$^∀$, —NH$_2$, —NHR$^∀$, —NR$^∀_2$, or —NO$_2$, wherein each R$^∀$ is unsubstituted or where preceded by "halo" is substituted only with one or more halogens, and is independently C$_{1-4}$ aliphatic, —CH$_2$Ph, —O(CH$_2$)$_{0-4}$Ph, or a 5- to 6-membered saturated, partially unsaturated, or aryl ring having 0-4 heteroatoms independently selected from nitrogen, oxygen, or sulfur.

As used herein, the term "catalyst" refers to a substance the presence of which increases the rate and/or extent of a chemical reaction, while not being consumed or undergoing a permanent chemical change itself.

As used herein, the term "multidentate" refers to ligands having multiple sites capable of coordinating to a single metal center.

As used herein, the term "activating moiety" refers to a moiety comprising one or more activating functional groups. In certain embodiments, an activating moiety improves the catalytic activity of a metal complex. In some embodiments, such improved catalytic activity is characterized by higher conversion of starting materials compared to a metal complex lacking an activating moiety. In some embodiments, such improved catalytic activity is characterized by higher rate of conversion of starting materials compared to a metal complex lacking an activating moiety. In some embodiments, such improved catalytic activity is characterized by higher yield of product compared to a metal complex lacking an activating moiety.

DETAILED DESCRIPTION OF CERTAIN EMBODIMENTS

The present invention provides, among other things, metal complexes for the copolymerization of carbon dioxide and epoxides and methods of using the same. In certain embodiments, provided metal complexes contain a metal-salen complex tethered to two or more cationic activating moieties. In some embodiments, each activating moiety comprises a linker and one or more cationic functional groups. In some embodiments, provided metal complexes act as polymerization catalysts.

In certain embodiments, the present invention encompasses metal complexes comprising a metal atom coordinated with a salen ligand, the salen ligand comprising two halves with each half coordinated to the metal atom via an imine and an oxygen atom wherein the metal complex is characterized in that one of the two halves of the salen ligand has two or more cationic activating moieties covalently tethered to it and the other half has no tethered activating moieties.

In certain embodiments, the cationic activating moieties tethered to the ligand are independently selected from the group consisting of onium salts, nitrogen-containing functional groups, phosphorous-containing functional groups, and arsenic-containing functional groups. In certain embodiments, at least one activating moiety comprises an ammonium salt. In certain embodiments, at least one activating moiety comprises a guanidinium salt. In certain embodiments, at least one activating moiety comprises an amidinium salt.

In certain embodiments, the half of the ligand having no tethered cationic activating moieties is derived from salicylaldehyde optionally substituted with one or more aliphatic groups.

In certain embodiments, the half of the ligand having no tethered cationic activating moieties comprises or is derived from a gamma dicarbonyl compound. In certain embodiments, a gamma dicarbonyl compound comprises optionally substituted acetylacetone. In certain embodiments, a gamma dicarbonyl compound comprises optionally substituted malonic acid derivative.

In certain embodiments, the present invention encompasses metal complexes having a structure:

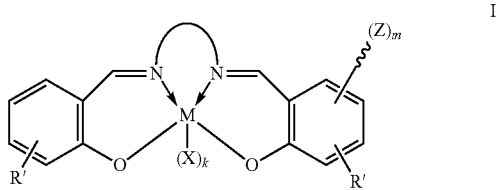

wherein:
M is a metal atom;
X is a nucleophile capable of ring opening an epoxide;
k is an integer from 0-2 inclusive;
R' represents one or more substituents optionally present on the phenyl rings and each R' is independently selected from the group consisting of: halogen, —NO$_2$, —CN, —SR$^y$, —S(O)R$^y$, —S(O)$_2$R$^y$, —NR$^y$C(O)R$^y$, —OC(O)R$^y$, —CO$_2$R$^y$, —NCO, —CNO, —SiR$_3$, —N$_3$, —OR$^y$, —OC(O)N(R$^y$)$_2$, —N(R$^y$)$_2$, —NR$^y$C(O)R$^y$, —NR$^y$C(O)OR$^y$, —C(O)R$^y$, —C(O)N(R$^y$)$_2$, —SO$_2$N(R$^y$)$_2$, —N(R$^y$)C(O)NR$^y$)$_2$, —N(R)SO$_2$R; or an optionally substituted radical selected from the group consisting of C$_{1-20}$ aliphatic; C$_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur, where two or more adjacent R' groups can be taken together to form an optionally substituted saturated, partially unsaturated, or aromatic 5- to 12-membered ring containing 0 to 4 heteroatoms;

$R^y$ at each occurrence is independently hydrogen, an optionally substituted radical selected the group consisting of acyl; $C_{1-6}$ aliphatic; $C_{1-6}$ heteroaliphatic; carbamoyl; arylalkyl; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; an oxygen protecting group; and a nitrogen protecting group, where two R groups on the same nitrogen atom can optionally be taken together to form an optionally substituted 3- to 7-membered ring;

⌢ represents is an optionally substituted moiety linking the two nitrogen atoms of the diamine portion of the salen ligand, where

⌢ is selected from the group consisting of phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; or an optionally substituted $C_{2-20}$ aliphatic group, wherein one or more methylene units are optionally and independently replaced by —$NR^y$—, —$N(R^y)C(O)$—, —$C(O)N(R^y)$—, —$OC(O)N(R^y)$—, —$N(R^y)C(O)O$—, —OC(O) O—, —O—, —C(O)—, —OC(O)—, —C(O)O—, —S—, —SO—, —$SO_2$—, —C(=S)—, —C(=$NR^y$)—, —C(=$NOR^y$)— or —N=N—; and ∼∼∼($Z)_m$ represents one or more activating moieties, where " ∼∼∼ " is a covalent linker containing one or more atoms selected from the group consisting of C, O, N, S, and Si; Z is a cationic functional group and each m is independently an integer from 1 to 4 indicating the number of individual activating functional groups present in each activating moiety;

wherein a total of at least two cationic functional groups (Z) are present on the metal complex.

(i) Z Groups.

As described above, Z groups are cationic functional groups, and metal complexes encompassed by the present invention have two or more such groups. Z groups typically contain at least one nitrogen, phosphorous, arsenic, or sulfur atom with a positive charge, though in some cases a Z group may have two or more such atoms or the positive charge may be delocalized across two or more atoms in the functional group through resonance structures. Each Z group may be the same or different.

In certain embodiments, each cationic functional group (Z) is independently selected from the group consisting of:

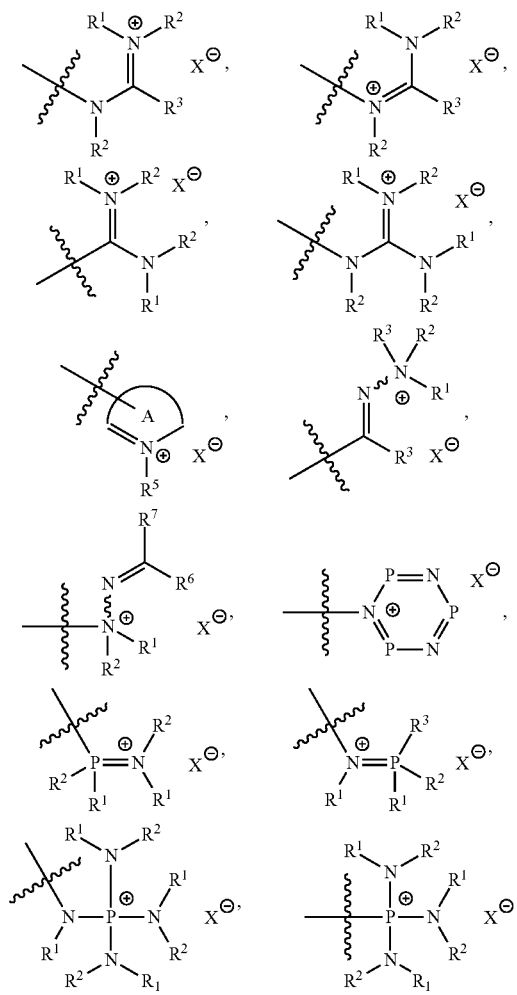

-continued

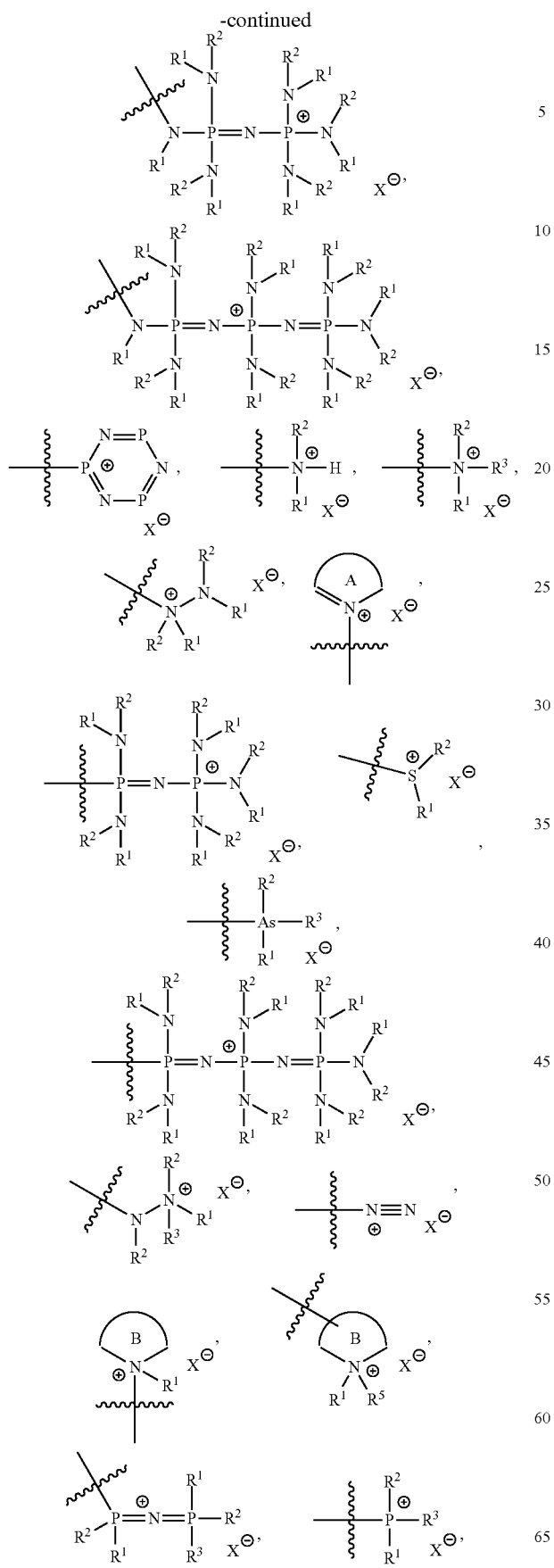

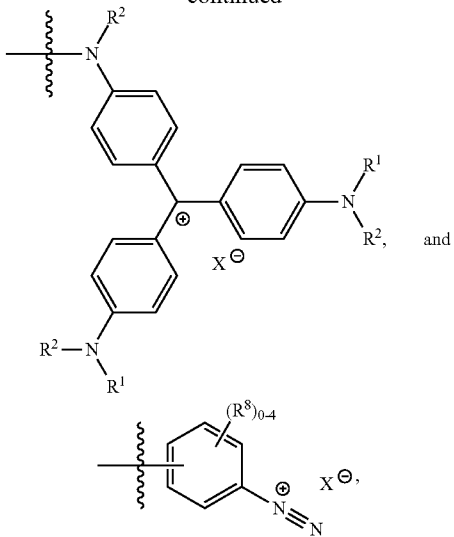

or a combination of two or more of these,
wherein:
each occurrence of $R^1$, $R^2$, and $R^3$ is independently hydrogen or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; wherein any two or more $R^1$, $R^2$, and $R^3$ groups can be taken together with intervening atoms to form one or more optionally substituted rings optionally containing one or more additional heteroatoms;
$R^5$ is $R^2$ or hydroxyl; wherein $R^1$ and $R^5$ can be taken together with intervening atoms to form one or more optionally substituted carbocyclic, heterocyclic, aryl, or heteroaryl rings;
each $R^6$ and $R^7$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein $R^6$ and $R^7$ can be taken together with intervening atoms to form one or more optionally substituted rings optionally containing one or more heteroatoms, and an $R^6$ and $R^7$ group can be taken with an $R^1$ or $R^2$ group to form one or more optionally substituted rings;

each occurrence of $R^8$ is independently selected from the group consisting of: halogen, $-NO_2$, $-CN$, $-SR^y$, $-S(O)R^y$, $-S(O)_2R^y$, $-NR^yC(O)R^y$, $-OC(O)R^y$, $-CO_2R^y$, $-NCO$, $-CNO$, $-SiR_3$, $-N_3$, $-OR^y$, $-OC(O)N(R^y)_2$, $-N(R^y)_2$, $-NR^yC(O)R^y$, $-NR^yC(O)O$ $R^y$, $-C(O)R^y$, $-C(O)N(R^y)_2$, $-SO_2N(R^y)_2$, $-N(R^y)C(O)N(R^y)_2$, $-N(R)SO_2R$; or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein each $R^y$ is independently as defined above and described in classes and subclasses herein, and where two or more adjacent $R^8$ groups can be taken together to form an optionally substituted saturated, partially unsaturated, or aromatic 5- to 12-membered ring containing 0 to 4 heteroatoms;

$X^-$ is any anion;

Ring A is an optionally substituted, 5- to 10-membered heteroaryl group; and

Ring B is an optionally substituted, 3- to 8-membered saturated or partially unsaturated monocyclic heterocyclic ring having 0-2 heteroatoms in addition to the depicted ring nitrogen atom independently selected from nitrogen, oxygen, or sulfur.

In certain embodiments, each cationic functional group (Z), is independently selected from the group consisting of:

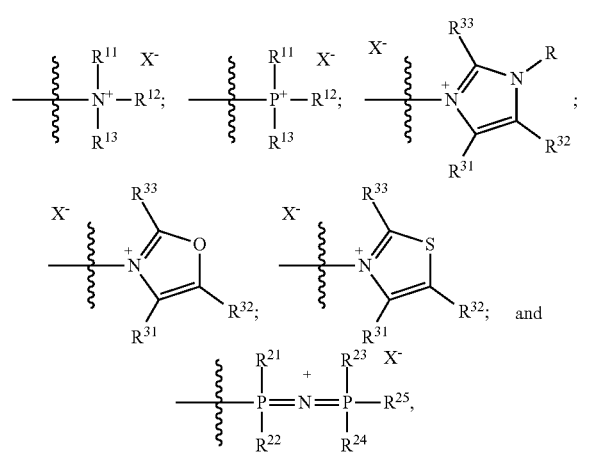

where $X^-$ is any anion;

$R^{11}$, $R^{12}$, $R^{13}$, $R^{21}$, $R^{22}$, $R^{23}$, $R^{24}$ and $R^{25}$ are each independently hydrogen; $C_1$-$C_{20}$ alkyl; $C_1$-$C_{20}$ alkyl having one or more functional moieties selected from the group consisting of halogen, nitrogen, oxygen, silicon, sulfur and phosphorus; $C_2$-$C_{20}$ alkenyl; $C_2$-$C_{20}$ alkenyl having one or more functional moieties selected from the group consisting of halogen, nitrogen, oxygen, silicon, sulfur and phosphorus; $C_7$-$C_{20}$ alkylaryl; $C_7$-$C_{20}$ alkylaryl having one or more functional moieties selected from the group consisting of halogen, nitrogen, oxygen, silicon, sulfur and phosphorus; $C_7$-$C_{20}$ arylalkyl; $C_7$-$C_{20}$ arylalkyl having one or more functional moieties selected from the group consisting of halogen, nitrogen, oxygen, silicon, sulfur and phosphorus; or a metalloid radical of group XIV metal substituted by hydrocarbyl, two of $R^{11}$, $R^{12}$ and $R^{13}$, or two of $R^{21}$, $R^{22}$, $R^{23}$, $R^{24}$ and $R^{25}$ being optionally fused together to form a bridged structure;

$R^{31}$, $R^{32}$ and $R^{33}$ are each independently hydrogen; $C_1$-$C_{20}$ alkyl; $C_1$-$C_{20}$ alkyl having one or more functional moieties selected from the group consisting of halogen, nitrogen, oxygen, silicon, sulfur and phosphorus; $C_2$-$C_{20}$ alkenyl; $C_2$-$C_{20}$ alkenyl having one or more functional moieties selected from the group consisting of halogen, nitrogen, oxygen, silicon, sulfur and phosphorus; $C_7$-$C_{20}$ alkylaryl; $C_7$-$C_{20}$ alkylaryl having one or more functional moieties selected from the group consisting of halogen, nitrogen, oxygen, silicon, sulfur and phosphorus; $C_7$-$C_{20}$ arylalkyl; $C_7$-$C_{20}$ arylalkyl having one or more functional moieties selected from the group consisting of halogen, nitrogen, oxygen, silicon, sulfur and phosphorus; or a metalloid radical of group XIV metal substituted by hydrocarbyl, two of $R^{31}$, $R^{32}$ and $R^{33}$ being optionally fused together to form a bridged structure;

R is hydrogen; $C_1$-$C_{20}$ alkyl; $C_1$-$C_{20}$ alkyl having one or more functional moieties selected from the group consisting of halogen, nitrogen, oxygen, silicon, sulfur and phosphorus; $C_2$-$C_{20}$ alkenyl; $C_2$-$C_{20}$ alkenyl having one or more functional moieties selected from the group consisting of halogen, nitrogen, oxygen, silicon, sulfur and phosphorus; $C_7$-$C_{20}$ alkylaryl; $C_7$-$C_{20}$ alkylaryl having one or more functional moieties selected from the group consisting of halogen, nitrogen, oxygen, silicon, sulfur and phosphorus; $C_7$-$C_{20}$ arylalkyl; $C_7$-$C_{20}$ arylalkyl having one or more functional moieties selected from the group consisting of halogen, nitrogen, oxygen, silicon, sulfur and phosphorus.

It will be appreciated that for provided metal complexes and portions thereof, where a cationic group is depicted, a $X^-$ counterion group is intended whether explicitly shown or not.

In certain embodiments, at least one Z group is an ammonium group. In certain embodiments, a Z group comprises an alkylammonium group. In certain embodiments, a Z group has a formula:

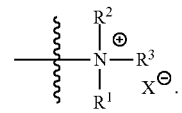

where $R^1$, $R^2$, $R^3$ and $X^-$ are as defined above. In certain embodiments, each $R^1$, $R^2$, and $R^3$ group on the ammonium moiety is an alkyl group. In certain embodiments, each $R^1$, $R^2$, and $R^3$ group is independently a $C_1$-$C_{20}$ straight chain, branched, or cyclic alkyl group. In certain embodiments, each $R^1$, $R^2$, and $R^3$ group is independently a $C_1$-$C_{12}$ straight or branched alkyl group. In certain embodiments, each $R^1$, $R^2$, and $R^3$ group is independently a $C_1$-$C_8$ straight or branched alkyl group. In certain embodiments, each $R^1$, $R^2$, and $R^3$ group is independently a $C_1$-$C_6$ straight or branched alkyl group. In certain embodiments, each $R^1$, $R^2$, and $R^3$ group is independently a $C_1$-$C_6$ n-alkyl group. In certain embodiments, each $R^1$, $R^2$, and $R^3$ group is independently selected from the group consisting of: methyl, ethyl, n-propyl, isopropyl, n-butyl, sec-butyl, tert-butyl, n-pentyl, and n-hexyl. In certain embodiments, two or more of $R^1$, $R^2$, and $R^3$ are taken together with the nitrogen atom to form a ring. Such compounds include analogs of known nitrogen heterocycles such as pyrrolidine, piperidine, morpholine, piperazine, dabco, quinuclidine and the like.

In certain embodiments, a Z group comprises a heterocyclic ammonium group. In certain embodiments, such compounds comprise cationic heterocycles such as imidizolium, oxazolium, thiazolium, pyridinium, pyrimidinium and the like.

In certain embodiments, at least one cationic activating functional group is a guanidinium group. In certain embodiments, such guanidinium groups have a structure:

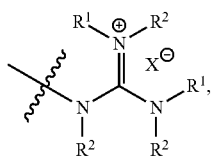

wherein each $R^1$ and $R^2$ is independently as defined above and described in classes and subclasses herein. In some embodiments, each $R^1$ and $R^2$ is independently hydrogen or optionally substituted $C_{1-20}$ aliphatic. In some embodiments, each $R^1$ and $R^2$ is independently hydrogen or optionally substituted $C_{1-10}$ aliphatic. In some embodiments, each $R^1$ and $R^2$ is independently hydrogen or $C_{1-12}$ aliphatic. In some embodiments, each $R^1$ and $R^2$ is independently hydrogen or $C_{1-20}$ heteroaliphatic. In some embodiments, each $R^1$ and $R^2$ is independently hydrogen or phenyl. In some embodiments, each $R^1$ and $R^2$ is independently hydrogen or 8- to 10-membered aryl. In some embodiments, each $R^1$ and $R^2$ is independently hydrogen or 5- to 10-membered heteroaryl. In some embodiments, each $R^1$ and $R^2$ is independently hydrogen or 3- to 7-membered heterocyclic. In some embodiments, one or more of $R^1$ and $R^2$ is optionally substituted $C_1$-12 aliphatic.

In some embodiments, where a Z group is a guanidium, any two or more $R^1$ or $R^2$ groups are taken together with intervening atoms to form one or more optionally substituted carbocyclic, heterocyclic, aryl, or heteroaryl rings. In certain embodiments, $R^1$ and $R^2$ groups are taken together to form an optionally substituted 5- or 6-membered ring. In some embodiments, three or more $R^1$ and/or $R^2$ groups are taken together to form an optionally substituted fused ring system.

In certain embodiments, two $R^1$ or $R^2$ groups are taken together with intervening atoms to form a compound selected from:

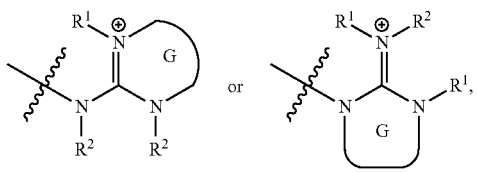

wherein each $R^1$ and $R^2$ is independently as defined above and described in classes and subclasses herein, and Ring G is an optionally substituted 5- to 7-membered saturated or partially unsaturated heterocyclic ring.

In certain embodiments, multiple $R^1$ and $R^2$ groups are taken together with intervening atoms to form a bicyclic guanidinium group:

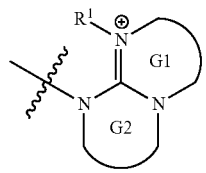

wherein $R^1$ is as defined above and described in classes and subclasses herein, and Ring G1 and G2 are independently optionally substituted 5- to 7-membered saturated or partially unsaturated heterocyclic rings.

It will be appreciated that when a guanidinium cation is depicted as

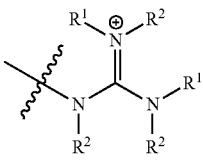

all such resonance forms are contemplated and encompassed by the present disclosure. For example, such groups can also be depicted as

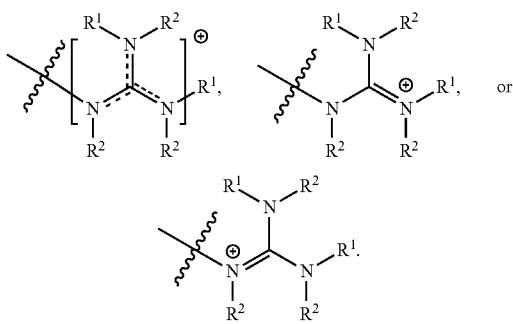

In specific embodiments, a guanidinium activating functional group is selected from the group consisting of:

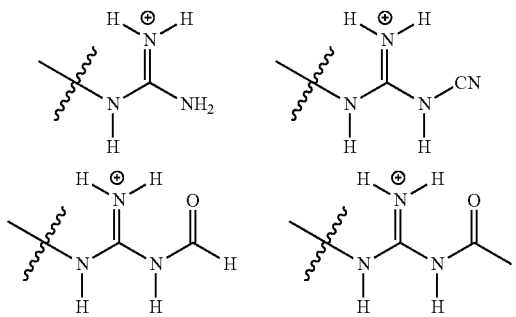

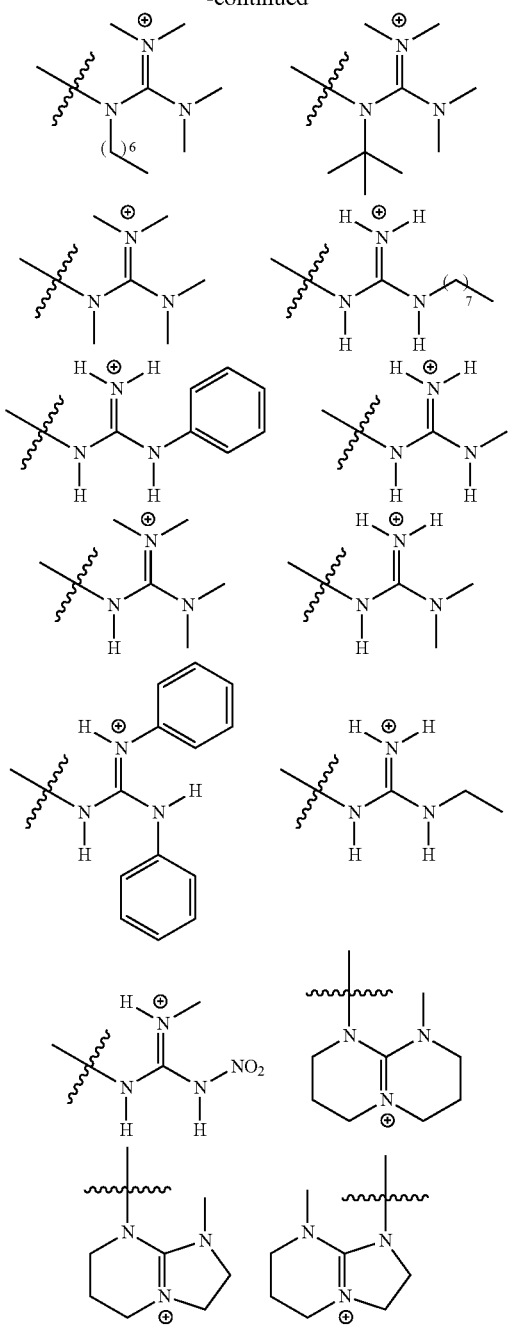

In some embodiments, an activating functional group is a sulfonium group or an arsonium group:

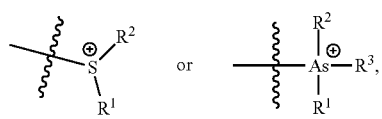

wherein each of $R^1$, $R^2$, and $R^3$ are as defined above and described in classes and subclasses herein.

In specific embodiments, an arsonium activating functional group is selected from the group consisting of:

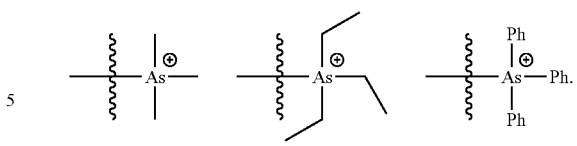

In some embodiments, an activating functional group is an optionally substituted nitrogen-containing heterocycle. In certain embodiments, the nitrogen-containing heterocycle is an aromatic heterocycle. In certain embodiments, the optionally substituted nitrogen-containing heterocycle is selected from the group consisting of: pyridine, imidazole, pyrrolidine, pyrazole, quinoline, thiazole, dithiazole, oxazole, triazole, pyrazolem, isoxazole, isothiazole, tetrazole, pyrazine, thiazine, and triazine.

In some embodiments, a nitrogen-containing heterocycle includes a quaternarized nitrogen atom. In certain embodiments, a nitrogen-containing heterocycle includes an iminium moiety such as

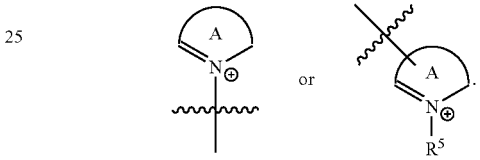

In certain embodiments, the optionally substituted nitrogen-containing heterocycle is selected from the group consisting of pyridinium, imidazolium, pyrrolidinium, pyrazolium, quinolinium, thiazolium, dithiazolium, oxazolium, triazolium, isoxazolium, isothiazolium, tetrazolium, pyrazinium, thiazinium, and triazinium.

In certain embodiments, a nitrogen-containing heterocycle is linked to a metal complex via a ring nitrogen atom. In some embodiments, a ring nitrogen to which the attachment is made is thereby quaternized, and in some embodiments, linkage to a metal complex takes the place of an N—H bond and the nitrogen atom thereby remains neutral. In certain embodiments, an optionally substituted N-linked nitrogen-containing heterocycle is a pyridinium derivative. In certain embodiments, optionally substituted N-linked nitrogen-containing heterocycle is an imidazolium derivative. In certain embodiments, optionally substituted N-linked nitrogen-containing heterocycle is a thiazolium derivative. In certain embodiments, optionally substituted N-linked nitrogen-containing heterocycle is a pyridinium derivative.

In some embodiments, an activating functional group is

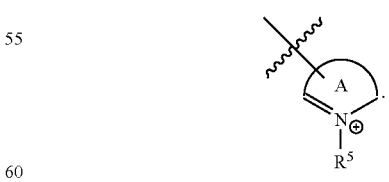

In certain embodiments, ring A is an optionally substituted, 5- to 10-membered heteroaryl group. In some embodiments, Ring A is an optionally substituted, 6-membered heteroaryl group. In some embodiments, Ring A is a ring of a fused heterocycle. In some embodiments, Ring A is an optionally substituted pyridyl group.

In some embodiments, when Z is

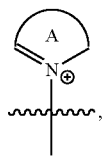

ring A is other than an imidazole, an oxazole, or a thiazole.

In specific embodiments, a nitrogen-containing heterocycle activating functional group is selected from the group consisting of:

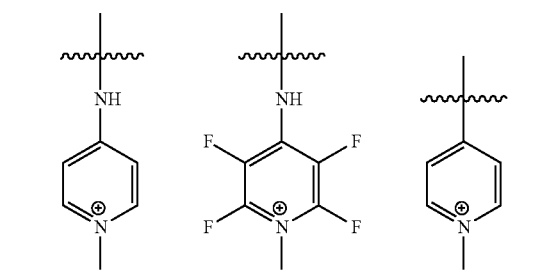

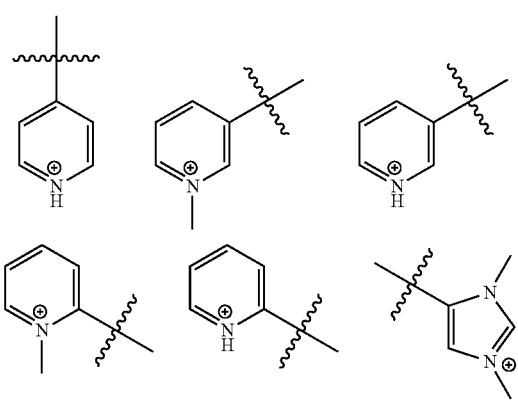

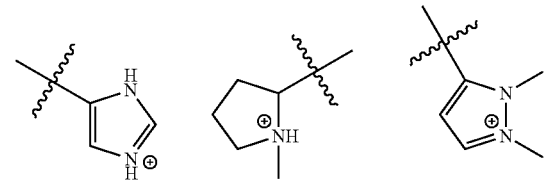

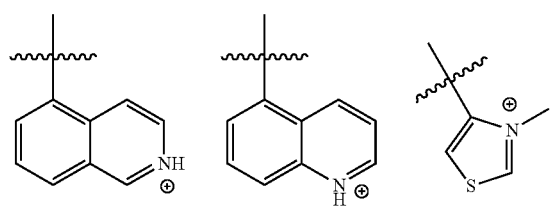

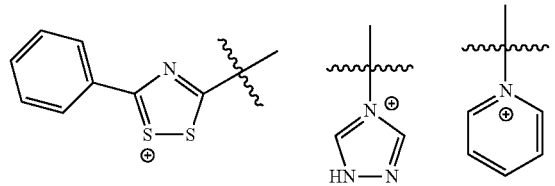

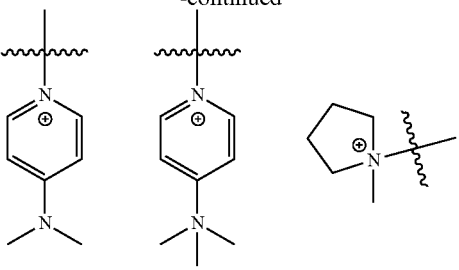

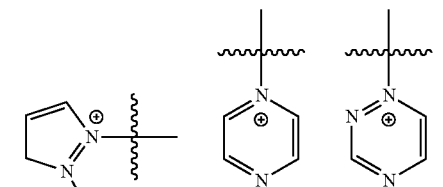

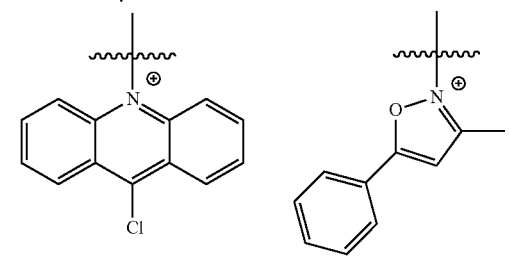

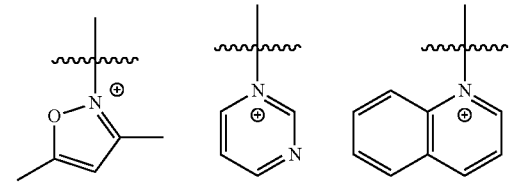

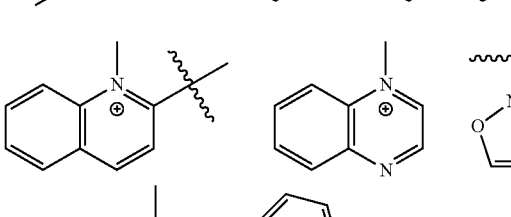

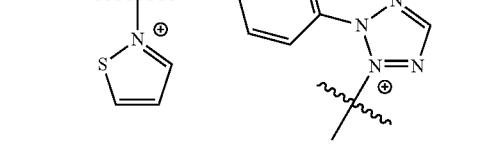

In certain embodiments, Ring B is a 5-membered saturated or partially unsaturated monocyclic heterocyclic ring. In certain embodiments, Ring B is a 6-membered saturated or partially unsaturated heterocycle. In certain embodiments, Ring B is a 7-membered saturated or partially unsaturated heterocycle. In certain embodiments, Ring B is tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. In some embodiments, Ring B is piperidinyl.

In some embodiments, an activating functional group an amidinum group. In certain embodiments an amidinium Z group is

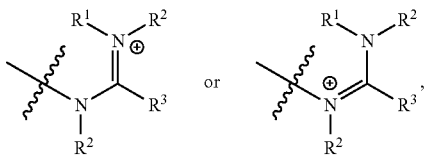

where each $R^1$, $R^2$, and $R^3$ is independently as defined above and described in classes and subclasses herein.

In some embodiments, an amidinium Z group is

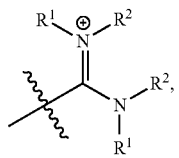

wherein each $R^1$ and $R^2$ is independently as defined above and described in classes and subclasses herein.

In certain embodiments where a Z group is an amidinium, $R^1$ and $R^2$ groups are taken together with intervening atoms to form a compound selected from:

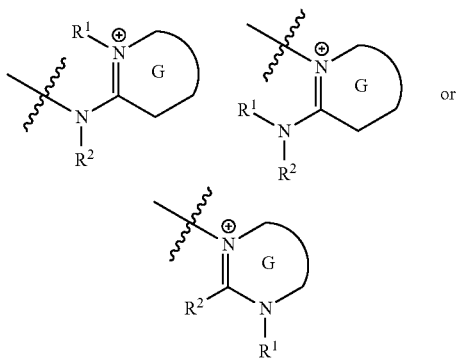

wherein each $R^1$ and $R^2$ is independently as defined above and described in classes and subclasses herein, and Ring G is an optionally substituted, 5- to 7-membered saturated or partially unsaturated heterocyclic ring.

In certain embodiments, multiple $R^1$ and $R^2$ groups are taken together with intervening atoms to form a bicyclic amidinium group:

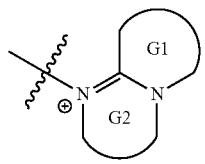

wherein $R^1$ is as defined above and described in classes and subclasses herein, and Ring G1 and G2 are independently optionally substituted 5- to 7-membered saturated or partially unsaturated heterocyclic rings.

In certain embodiments, an activating functional group is selected from the group consisting of:

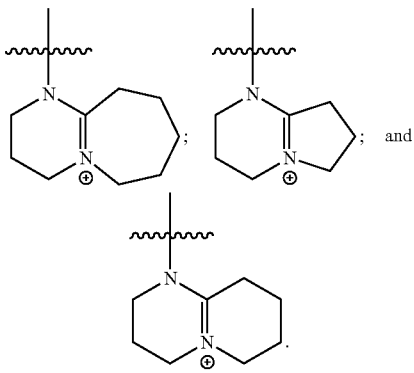

In some embodiments, an activating functional group is

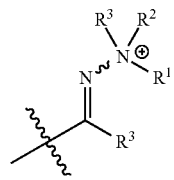

wherein each $R^1$, $R^2$, and $R^3$ is independently as defined above and described in classes and subclasses herein.

In some embodiments, an activating functional group is

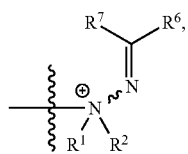

wherein each of $R^1$, $R^2$, $R^6$, and $R^7$ is as defined above and described in classes and subclasses herein. In certain embodiments, $R^6$ and $R^7$ are each independently an optionally substituted group selected from the group consisting of $C_{1-20}$ aliphatic; $C_{1-20}$ heteroaliphatic; phenyl, and 8-10-membered aryl. In some embodiments, $R^6$ and $R^7$ are each independently an optionally substituted $C_{1-20}$ aliphatic. In some embodiments, $R^6$ and $R^7$ are each independently an optionally substituted $C_{1-20}$ heteroaliphatic having. In some embodiments, $R^6$ and $R^7$ are each independently an optionally substituted phenyl or 8-10-membered aryl. In some embodiments, $R^6$ and Rare each independently an optionally substituted 5- to 10-membered heteroaryl. In some embodiments, $R^6$ and $R^7$ can be taken together with intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted 5- to 10-membered heteroaryl. In some embodiments, $R^6$ and $R^7$ are each independently an optionally substituted $C_{1-6}$ aliphatic. In some embodiments, each occurrence of $R^6$ and $R^7$ is independently methyl, ethyl, propyl, butyl, pentyl, hexyl, heptyl, octyl, or benzyl. In some embodiments, each occurrence of $R^6$ and $R^7$ is independently perfluoro. In some embodiments, each occurrence of $R^6$ and $R^7$ is independently —$CF_2CF_3$.

In some embodiments, an activating functional group is

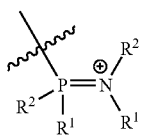

wherein each $R^1$ and $R^2$ is independently as defined above and described in classes and subclasses herein, both singly and in combination.

In some embodiments, an activating functional group is

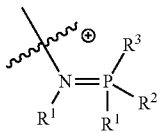

wherein each $R^1$, $R^2$, and $R^3$ is independently as defined above and described in classes and subclasses herein.

In some embodiments, an activating functional group is

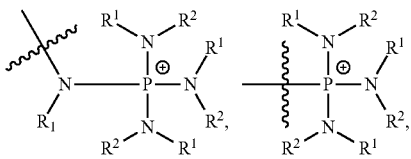

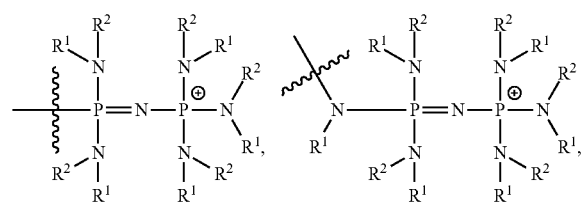

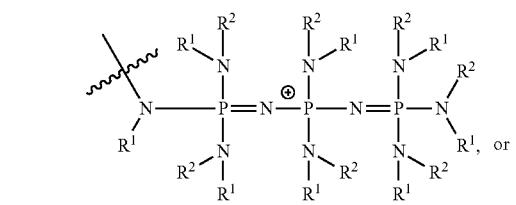

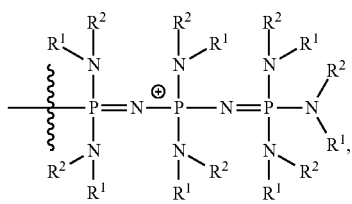

wherein each $R^1$ and $R^2$ is independently as defined above and described in classes and subclasses herein.

In some embodiments, an activating functional group is

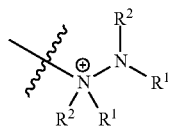

wherein each $R^1$ and $R^2$ is independently as defined above and described in classes and subclasses herein.

In some embodiments, an activating functional group is

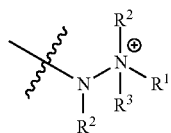

wherein each $R^1$, $R^2$, and $R^3$ is independently as defined above and described in classes and subclasses herein.

In some embodiments, an activating functional group is

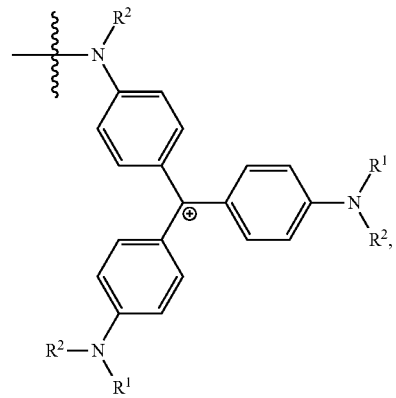

wherein each $R^1$ and $R^2$ is independently as defined above and described in classes and subclasses herein.

(ii) Linkers and Aryl Ring Substitution Patterns

As noted above, metal complexes of the present invention comprise two or more of the Z groups just described. These Z groups are attached to only one of the two aryl rings comprising the salen ligand. This situation can result from having two or more ⟶ $(Z)_m$ groups attached to one aryl ring, or can result from having one ⟶ $(Z)_m$ group where is m is 2 or more.

In certain embodiments, metal complexes of the present invention comprise two ⟶ $(Z)_m$ groups attached to one aryl ring of a salen ligand. In certain embodiments, such metal complexes have a formula II:

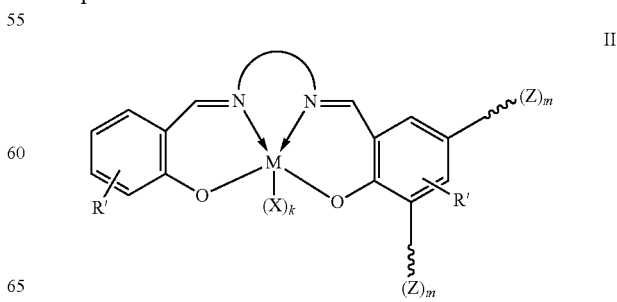

II where R', M, X, —ᴡᴡ , Z, k, and m are as defined above, and each —ᴡᴡ (Z)$_m$ group may be the same or different.

In certain embodiments where a metal complex conforms to formula II, no R' groups are present on the phenyl ring bearing the —ᴡᴡ (Z)$_m$ groups.

In certain embodiments, metal complexes of the present invention comprise one —ᴡᴡ (Z)$_m$ group where m is greater than 1. In certain embodiments of such metal complexes, m is 2. In certain embodiments of such metal complexes, m is 3. In certain embodiments, such metal complexes have a formula Ma or Mb:

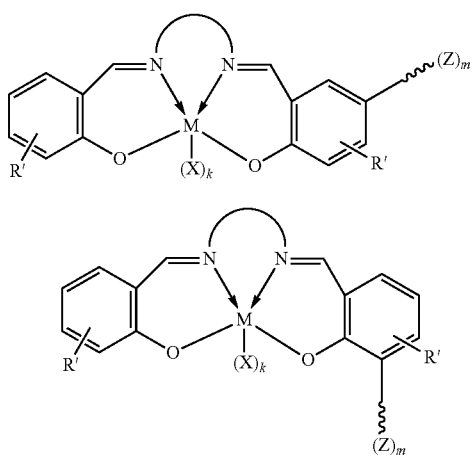

IIIa

IIIb where R', M, X, —ᴡᴡ , Z, and k are as defined above, and m is greater than 1.

As described above, each activating moiety —ᴡᴡ (Z)$_m$ comprises a linker " —ᴡᴡ " coupled to at least one activating functional group Z, with m denoting the number of activating functional groups present on a single linker moiety.

As noted above there may be one or more activating moiety —ᴡᴡ (Z)$_m$ tethered to a given metal complex. Similarly, each activating moiety itself may contain more than one activating functional group Z. In certain embodiments, each activating moiety contains only one activating functional group (i.e. m=1). In some embodiments, each activating moiety contains more than one activating functional groups (i.e. m>1). In certain embodiments, an activating moiety contains two activating functional groups (i.e. m=2). In certain embodiments, an activating moiety contains three activating functional groups (i.e. m=3). In certain embodiments, an activating moiety contains four activating functional groups (i.e. m=4). In certain embodiments where more than one activating functional group is present on an activating moiety, they are all the same functional group. In some embodiments where more than one activating functional group is present on an activating moiety, two or more of the activating functional groups are different.

In certain embodiments, each linker moiety —ᴡᴡ contains 1-30 atoms including at least one carbon atom, and optionally one or more atoms selected from the group consisting of N, O, S, Si, B, and P.

In certain embodiments, the linker is an optionally substituted $C_{2-30}$ aliphatic group wherein one or more methylene units are optionally and independently replaced by —NR$^y$—, —N(R$^y$)C(O)—, —C(O)N(R$^y$)—, —O—, —C(O)—, —OC(O)—, —C(O)O—, —S—, —SO—, —SO$_2$—, —C(=S)—, —C(=NR$^y$)—, or —N=N—, where each occurrence of R$^y$ is independently —H, or an optionally substituted radical selected from the group consisting of $C_{1-6}$ aliphatic, 3- to 7-membered heterocyclic, phenyl, and 8- to 10-membered aryl. In certain embodiments, a linker moiety is a $C_4$-$C_{12}$ aliphatic group substituted with one or more moieties selected from the group consisting of halogen, —NO$_2$, —CN, —SR$^y$, —S(O)R$^y$, —S(O)$_2$R$^y$, —NR$^y$C(O)R$^y$, —OC(O)R$^y$, —CO$_2$R$^y$, —NCO, —CNO, —SiR$_3$, —N$_3$, —OR$^y$, —OC(O)N(R$^y$)$_2$, —N(R$^y$)$_2$, —NR$^y$C(O)R$^y$, —NR$^y$C(O)OR$^y$, —C(O)R$^y$, —C(O)N(R$^y$)$_2$, —SO$_2$N(R$^y$)$_2$, —N(R$^y$)C(O)N(R$^y$)$_2$, —N(R)SO$_2$R; where R$^y$ is —H, or an optionally substituted radical selected from the group consisting of $C_{1-6}$ aliphatic 3- to 7-membered heterocyclic, phenyl, and 8- to 10-membered aryl.

In certain embodiments, a linker moiety is an optionally substituted $C_3$-$C_{30}$ aliphatic group. In certain embodiments, a linker is an optionally substituted $C_{4-24}$ aliphatic group. In certain embodiments, a linker moiety is an optionally substituted $C_4$-$C_{20}$ aliphatic group. In certain embodiments, a linker moiety is an optionally substituted $C_4$-$C_{12}$ aliphatic group. In certain embodiments, a linker is an optionally substituted $C_{4-10}$ aliphatic group. In certain embodiments, a linker is an optionally substituted $C_{4-8}$ aliphatic group. In certain embodiments, a linker moiety is an optionally substituted $C_4$-$C_6$ aliphatic group. In certain embodiments, a linker moiety is an optionally substituted $C_6$-$C_{12}$ aliphatic group. In certain embodiments, a linker moiety is an optionally substituted $C_8$ aliphatic group. In certain embodiments, a linker moiety is an optionally substituted $C_7$ aliphatic group. In certain embodiments, a linker moiety is an optionally substituted $C_6$ aliphatic group. In certain embodiments, a linker moiety is an optionally substituted $C_5$ aliphatic group. In certain embodiments, a linker moiety is an optionally substituted $C_4$ aliphatic group. In certain embodiments, a linker moiety is an optionally substituted $C_3$ aliphatic group. In certain embodiments, a aliphatic group in the linker moiety is an optionally substituted straight alkyl chain. In certain embodiments, the aliphatic group is an optionally substituted branched alkyl chain. In some embodiments, a linker moiety is a $C_4$ to $C_{20}$ alkyl group having one or more methylene groups replaced by —C(R$^a$R$^b$)— where R$^a$ and R$^b$ are each independently $C_1$-$C_4$ alkyl groups. In certain embodiments, a linker moiety consists of an aliphatic group having 4 to 30 carbons including one or more gem-dimethyl substituted carbon atoms.

In certain embodiments, a linker moiety includes one or more optionally substituted cyclic elements selected from the group consisting of saturated or partially unsaturated carbocyclic, aryl, heterocyclic, or heteroaryl. In certain embodiments, a linker moiety consists of the substituted cyclic element, in some embodiments the cyclic element is part of a linker with one or more non-ring heteroatoms or optionally substituted aliphatic groups comprising other parts of the linker moiety.

In some embodiments, a linker moiety is of sufficient length to allow one or more activating functional groups to be positioned near a metal atom of a metal complex. In certain embodiments, structural constraints are built into a linker moiety to control the disposition and orientation of one or more activating functional groups near a metal center of a metal complex. In certain embodiments such structural constraints are selected from the group consisting of cyclic moieties, bicyclic moieties, bridged cyclic moieties and tricyclic moieties. In some embodiments, such structural constraints are the result of acyclic steric interactions. In certain embodiments such structural constraints are selected from the group consisting of cis double bonds, trans double bonds, cis allenes, trans allenes, and triple bonds. In some embodiments, such structural constraints are selected from the group consisting of substituted carbons including geminally disubstituted groups such as sprirocyclic rings, gem dimethyl groups, gem diethyl groups and gem diphenyl groups. In certain embodiments such structural constraints are selected from the group consisting of heteroatom-containing functional groups such as sulfoxides, amides, and oximes.

In certain embodiments, linker moieties are selected from the group consisting of:

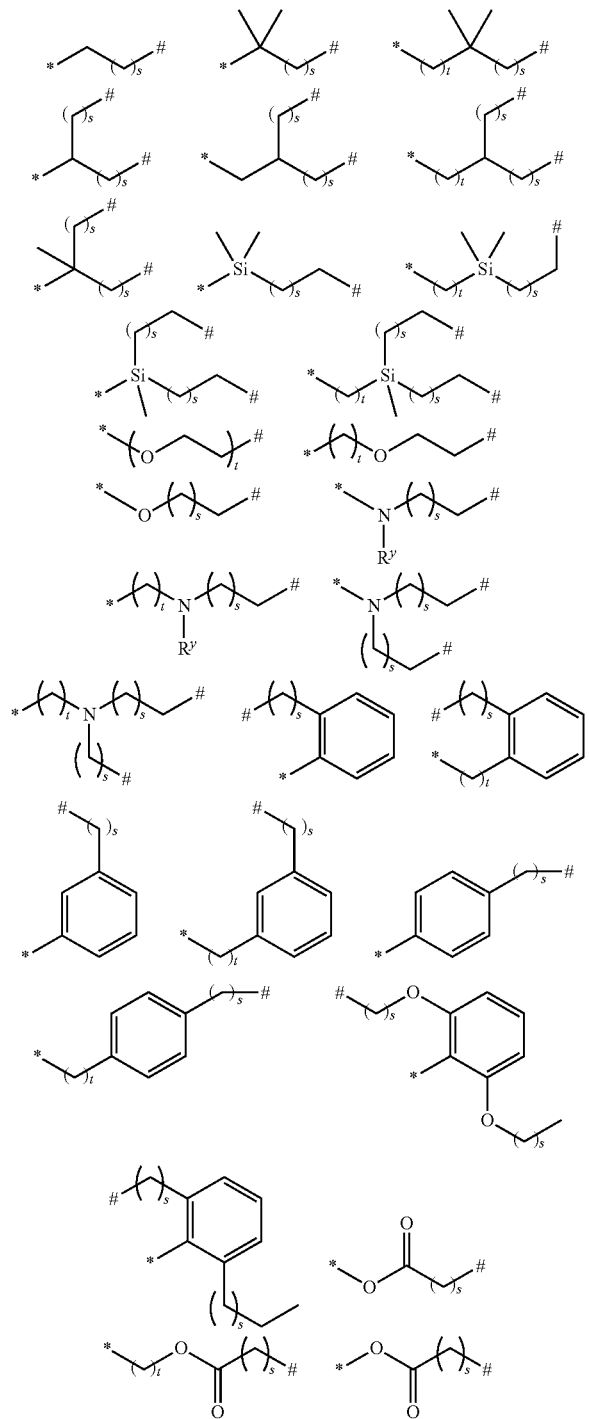
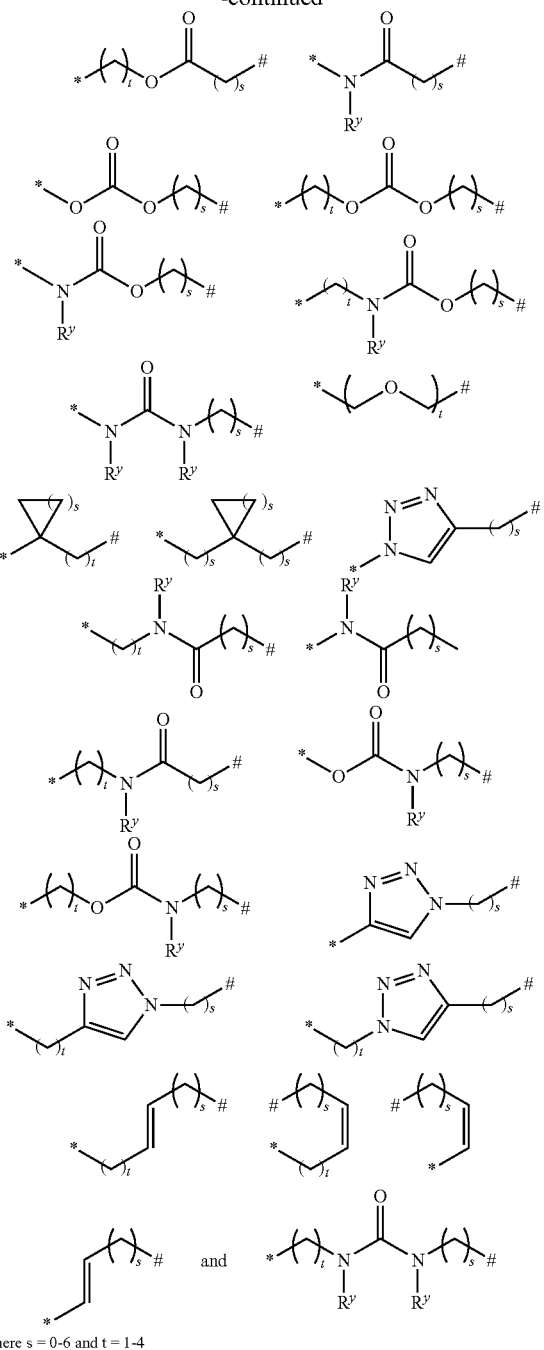

where s = 0-6 and t = 1-4 where * represents the site of attachment to a ligand, and each # represents a site of attachment of an activating functional group.

In some embodiments, s is 0. In some embodiments, s is 1. In some embodiments, s is 2. In some embodiments, s is 3. In some embodiments, s is 4. In some embodiments, s is 5. In some embodiments, s is 6.

In some embodiments, t is 1. In some embodiments, t is 2. In some embodiments, t is 3. In some embodiments, t is 4.

In some embodiments of provided metal complexes, each $R^y$ is —H, or an optionally substituted radical selected from the group consisting of $C_{1-6}$ aliphatic, 3- to 7-membered heterocyclic, phenyl, and 8- to 10-membered aryl. In some embodiments, an $R^y$ group attached to a nitrogen, oxygen, or sulfur atom on a provided metal complex is other than hydrogen.

In some embodiments of provided metal complexes, each R is —H, or an optionally substituted radical selected from the group consisting of $C_{1-6}$ aliphatic, 3- to 7-membered heterocyclic, phenyl, and 8- to 10-membered aryl. In some embodiments, an R group attached to a nitrogen, oxygen, or sulfur atom on a provided metal complex is other than hydrogen.

In some embodiments, an activating moiety  has a formula,

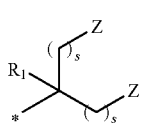

where $R^1$, *, s, and Z are as defined above. In certain embodiments, an activating moiety has a formula

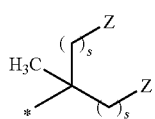

where *, s, and Z are as defined above. In certain embodiments, an activating moiety has a formula

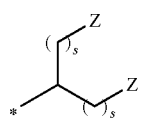

where *, s, and Z are as defined above and described in classes and subclasses herein.

In certain embodiments, an activating moiety has a formula selected from the group consisting of:

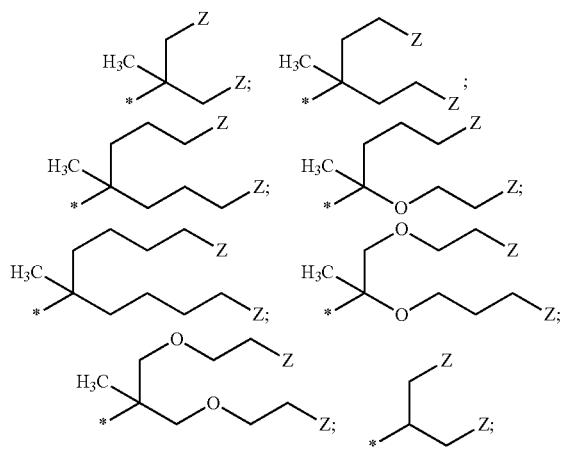

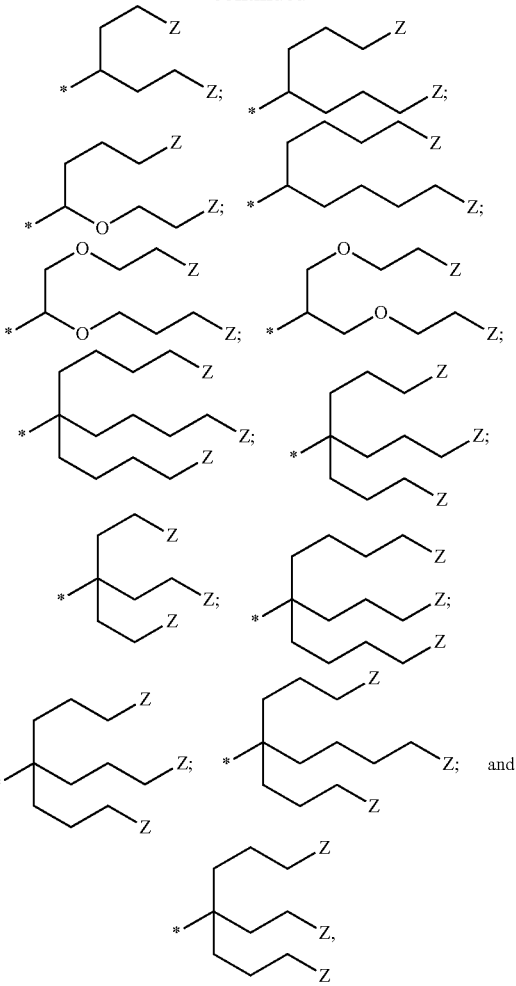

where Z and * are as defined above and described in classes and subclasses herein.

In certain embodiments, an activating moiety has a formula selected from the group consisting of:

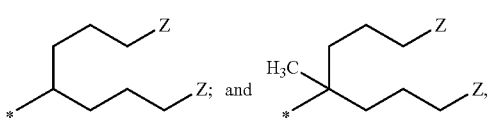

where Z, and * are as defined above and described in classes and subclasses herein.

In certain embodiments, an activating moiety has a formula selected from the group consisting of:

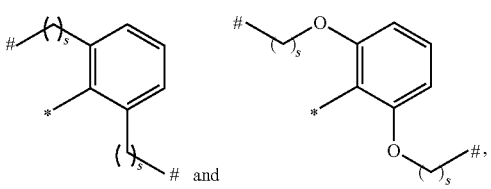

where *, #, and s are as defined above and described in classes and subclasses herein. In certain embodiments, an activating moiety has a formula selected from the group consisting of:

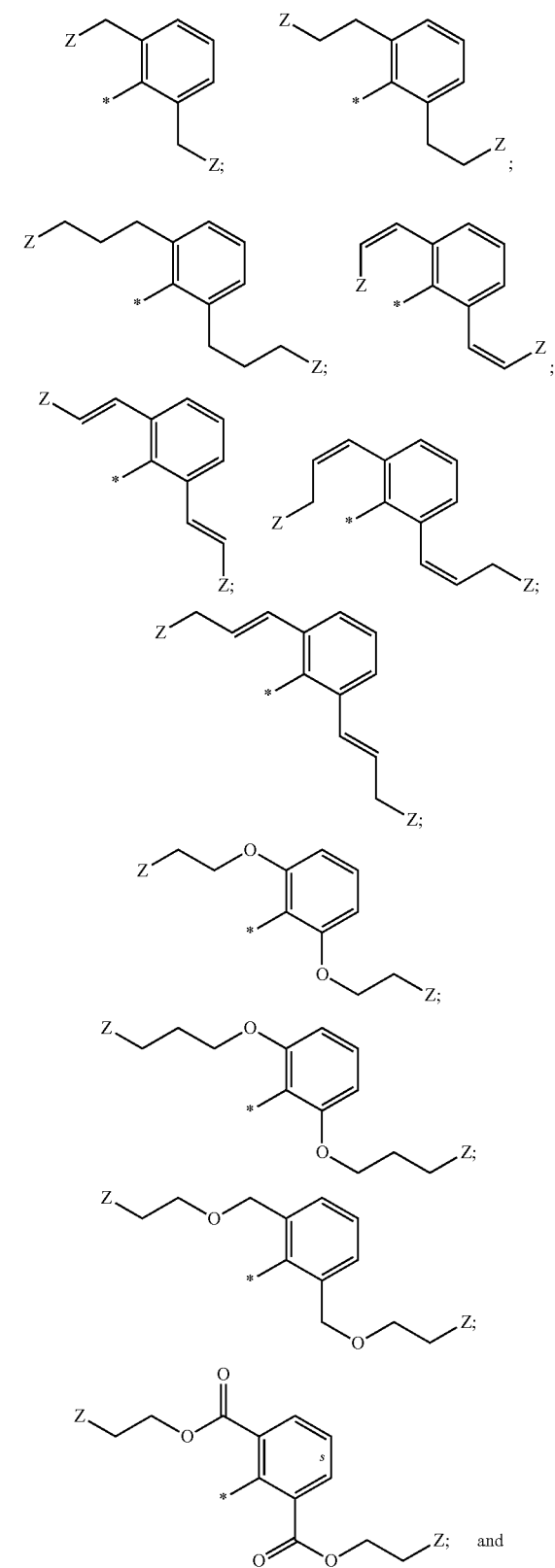

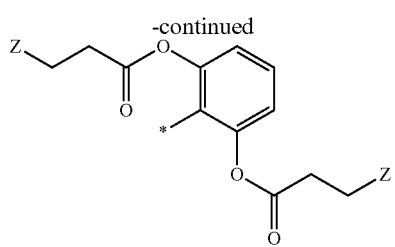

where Z, and * are as defined above and described in classes and subclasses herein.

In certain embodiments, an activating moiety has a formula selected from the group consisting of:

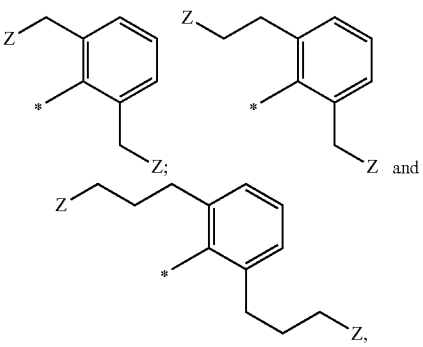

where Z and * are as defined above and described in classes and subclasses herein.

(iii) Metal Complexes

Metal complexes of the present invention conform the general formula I:

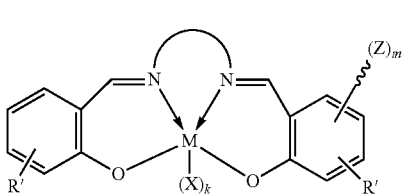

wherein:
M is a metal atom;
X is a nucleophile capable of ring opening an epoxide;
k is an integer from 0-2 inclusive;
R' represents one or more substituents optionally present on the phenyl rings and each R' is independently selected from the group consisting of: halogen, —$NO_2$, —CN, —$SR^y$, —$S(O)R^y$, —$S(O)_2R^y$, —$NR^yC(O)R^y$, —OC(O)$R^y$, —$CO_2R^y$, —NCO, —CNO, —$SiR_3$, —$N_3$, —$OR^y$, —OC(O)N($R^y$)$_2$, —N($R^y$)$_2$, —$NR^yC(O)R^y$, —$NR^yC(O)OR^y$, —C(O)$R^y$, —C(O)N($R^y$)$_2$, —$SO_2$N($R^y$)$_2$, —N($R^y$)C(O)N($R^y$)$_2$, —N(R)$SO_2$R; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur, where two or more adjacent R' groups can be taken together to form an optionally substituted saturated, partially unsaturated, or aromatic 5- to 12-membered ring containing 0 to 4 heteroatoms;

$R^y$ at each occurrence is independently hydrogen, an optionally substituted radical selected the group consisting of acyl; $C_{1-6}$ aliphatic; $C_{1-6}$ heteroaliphatic; carbamoyl; arylalkyl; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; an oxygen protecting group; and a nitrogen protecting group, where two R groups on the same nitrogen atom can optionally be taken together to form an optionally substituted 3- to 7-membered ring;

⌒ represents is an optionally substituted moiety linking the two nitrogen atoms of the diamine portion of the salen ligand, where

⌒ is selected from the group consisting of phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; or an optionally substituted $C_{2-20}$ aliphatic group, wherein one or more methylene units are optionally and independently replaced by —$NR^y$—, —$N(R^y)C(O)$—, —$C(O)N(R^y)$—, —$OC(O)N(R^y)$—, —$N(R^y)C(O)O$—, —$OC(O)O$—, —$O$—, —$C(O)$—, —$OC(O)$—, —$C(O)O$—, —$S$—, —$SO$—, —$SO_2$—, —$C(=S)$—, —$C(=NR^y)$—, —$C(=NOR^y)$— or —$N=N$—;

—⌇⌇⌇ $(Z)_m$ represents one or more activating moieties, where "—⌇⌇⌇" is a covalent linker containing one or more atoms selected from the group consisting of C, O, N, S, and Si; Z is a activating functional group and each m is independently an integer from 1 to 4 indicating the number of individual activating functional groups present in each activating moiety.

In certain embodiments of provided metal complexes, a metal complex has a structure selected from the group consisting of:

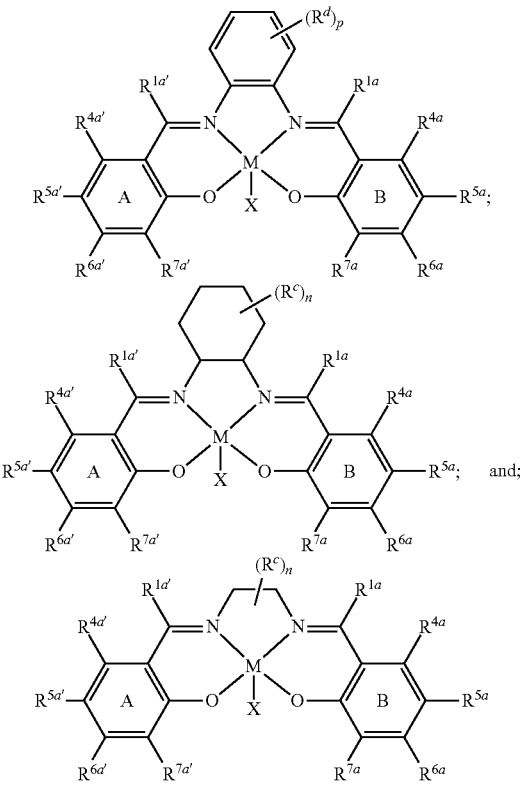

wherein:

$R^{1a}$ and $R^{1a'}$, are independently hydrogen, or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur;

$R^{4a}$, $R^{4a'}$, $R^{5a}$, $R^{5a'}$, $R^{6a}$, $R^{6a'}$, $R^{7a}$, and $R^{7a'}$ are each independently a —⌇⌇⌇ $(Z)_m$ group, hydrogen, halogen, —$NO_2$, —$CN$, —$SR^y$, —$S(O)R^y$, —$S(O)_2R^y$, —$NR^yC(O)R^y$, —$OC(O)R^y$, —$CO_2R^y$, —$NCO$, —$CNO$, —$SiR_3$, —$N_3$, —$OR^y$, —$OC(O)N(R^y)_2$, —N(R$^y$)$_2$, —NR$^y$C(O)R$^y$, —NR$^y$C(O)OR$^y$, —C(O)R$^y$, —C(O)N(R$^y$)$_2$, —SO$_2$N(R$^y$)$_2$, —N(R$^y$)CONR$^y$)$_2$, —N(R)SO$_2$R; or an optionally substituted radical selected from the group consisting of C$_{1-20}$ aliphatic; C$_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur;

wherein [R$^{1a}$ and R$^{4a}$], [R$^{1a'}$ and R$^{4a'}$] and any two adjacent R$^{4a}$, R$^{4a'}$, R$^{5a}$, R$^{5a'}$, R$^{6a}$, R$^{6a'}$, R$^{7a}$, and R$^{7a'}$ groups can be taken together with intervening atoms to form one or more optionally substituted rings;

R$^d$ at each occurrence is independently halogen, —OR, —NR$_2$, —SR, —CN, —NO$_2$, —SO$_2$R, —SOR, —SO$_2$NR$_2$; —CNO, —NRS O$_2$R, —NCO, —N$_3$, —SiR$_3$; or an optionally substituted radical selected from the group consisting of C$_{1-20}$ aliphatic; C$_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; where two or more R$^d$ groups may be taken together with intervening atoms to form one or more optionally substituted rings optionally containing one or more heteroatoms, R$^c$ at each occurrence is independently halogen, —OR, —NR$_2$, —SR, —CN, —NO$_2$, —SO$_2$R, —SOR, —SO$_2$NR$_2$; —CNO, —NRS O$_2$R, —NCO, —N$_3$, —SiR$_3$; or an optionally substituted radical selected from the group consisting of C$_{1-20}$ aliphatic; C$_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; where two or more R$^c$ groups may be taken together with the carbon atoms to which they are attached and any intervening atoms to form one or more optionally substituted rings; when two R$^c$ groups are attached to the same carbon atom, they may optionally be taken together along with the carbon atom to which they are attached to form an optionally substituted moiety selected from the group consisting of: a 3- to 8-membered spirocyclic ring, a carbonyl, an oxime, a hydrazone, and an imine;

n is 0 or an integer from 1 to 4, inclusive;

p is 0 or an integer from 1 to 6, inclusive;

R at each occurrence is independently hydrogen, an optionally substituted radical selected the group consisting of acyl; C$_{1-6}$ aliphatic; C$_{1-6}$ heteroaliphatic; carbamoyl; arylalkyl; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; an oxygen protecting group; and a nitrogen protecting group, where two R groups on the same nitrogen atom can optionally be taken together to form an optionally substituted 3- to 7-membered ring, wherein the metal complex comprises at least two Z groups, and wherein only one of the two aromatic rings denoted "A" and "B" in the structures above has a substituent that is a —ww (Z)$_m$.

In some embodiments, M is Co.

In some embodiments, R$^{1a}$, R$^{1a'}$, R$^{4a}$, R$^{4a'}$, R$^{6a}$, and R$^{6a'}$ are each —H. In some embodiments, R$^{5a}$, R$^{5a'}$, R$^{7a}$ and R$^{7a'}$ are each optionally substituted C$_1$-C$_{12}$ aliphatic. In some embodiments, R$^{4a}$, R$^{4a'}$, R$^{5a}$, R$^{5a'}$, R$^{6a}$, R$^{6a'}$, R$^{7a}$, and R$^{7a'}$ are each independently selected from the group consisting of: —H, —SiR$_3$; methyl, ethyl, n-propyl, i-propyl, n-butyl, sec-butyl, t-butyl, isoamyl, t-amyl, thexyl, and trityl. In some embodiments, R$^{1a}$, R$^{1a'}$, R$^{4a}$, R$^{4a'}$, R$^{6a}$, and R$^{6a'}$ are each —H. In some embodiments, R$^{7a}$ is selected from the group consisting of —H; methyl; ethyl; n-propyl; i-propyl; n-butyl; sec-butyl; t-butyl; isoamyl; t-amyl; thexyl; and trityl. In some embodiments, R$^{5a}$ and R$^{7a}$ are independently selected from the group consisting of —H; methyl; ethyl; n-propyl; i-propyl; n-butyl; sec-butyl; t-butyl; isoamyl; t-amyl; thexyl; and trityl. In certain embodiments, one or more of R$^{5a}$, R$^{5a'}$, R$^{7a}$ and R$^{7a'}$ is a —ww (Z)$_m$ group. In some embodiments, R$^{5a}$ and R$^{5a'}$ are a —ww (Z)$_m$ group.

In certain embodiments, a provided metal complex has a structure selected from the group consisting of:

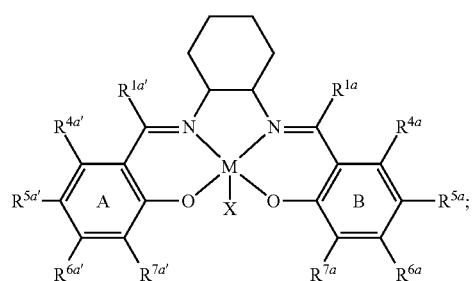

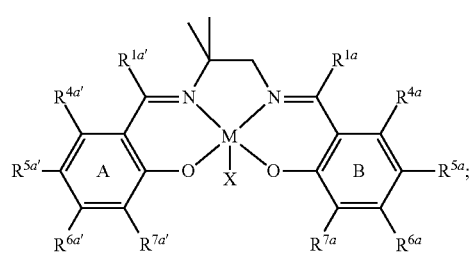

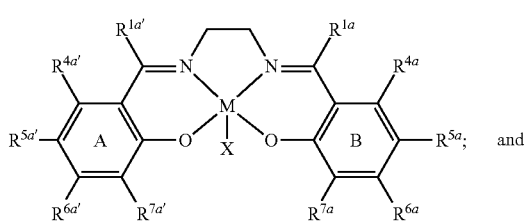

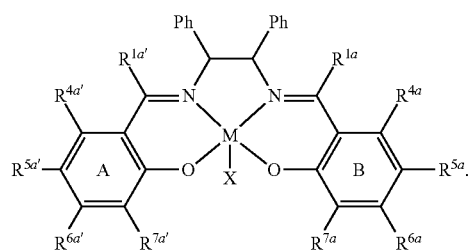

wherein $R^{1a}$, $R^{1a'}$, $R^{4a}$, $R^{4a'}$, $R^{5a}$, $R^{5a'}$, $R^{6a}$, $R^{6a'}$, $R^{7a}$, $R^{7a'}$, M, and X are as defined above and described in classes and subclasses herein, wherein the metal complex comprises at least two Z groups and wherein only one of the two aromatic rings denoted "A" and "B" in the structures above has a substituent that is a —∿∿ $(Z)_m$ group.

In certain embodiments of complexes having formulae described above, one of the phenyl rings denoted A or B in the structures above is selected from the group consisting of:

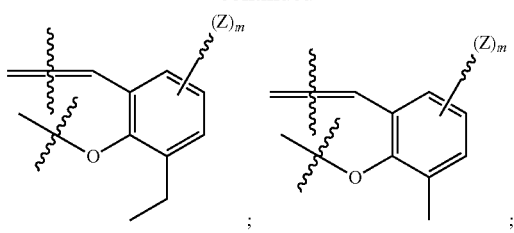

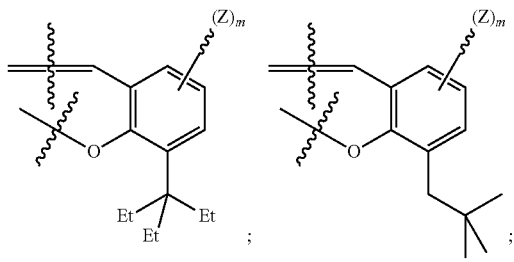

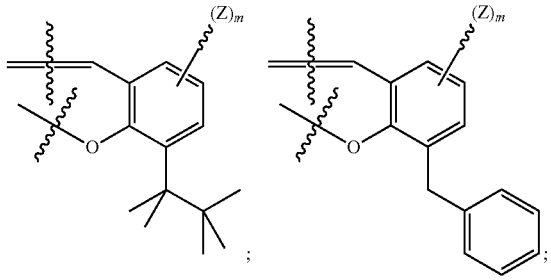

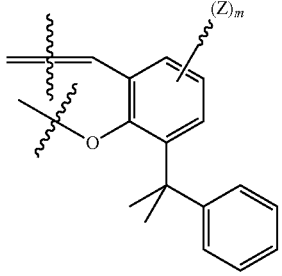

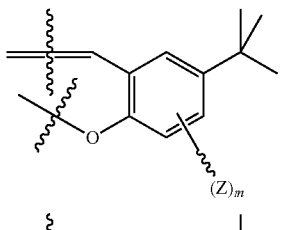

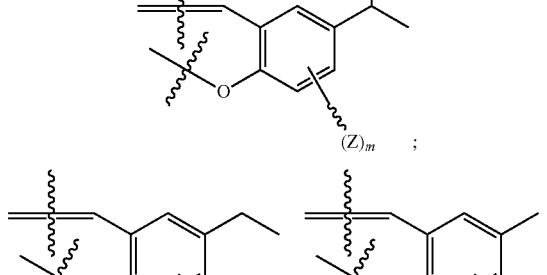

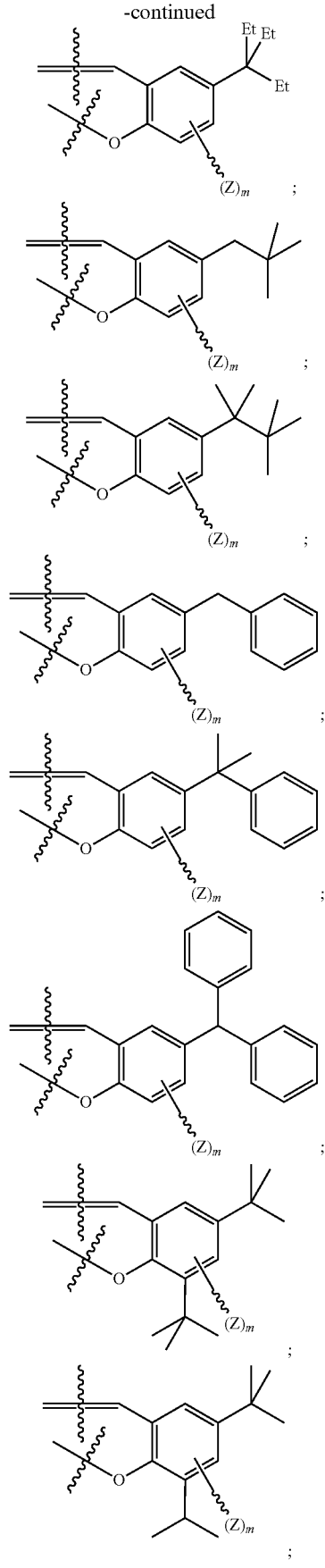
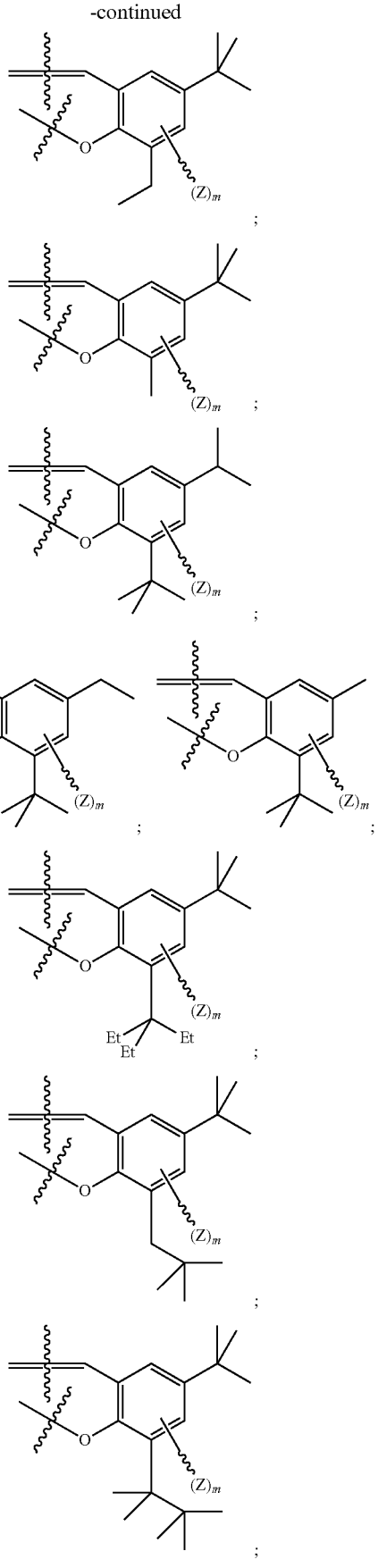

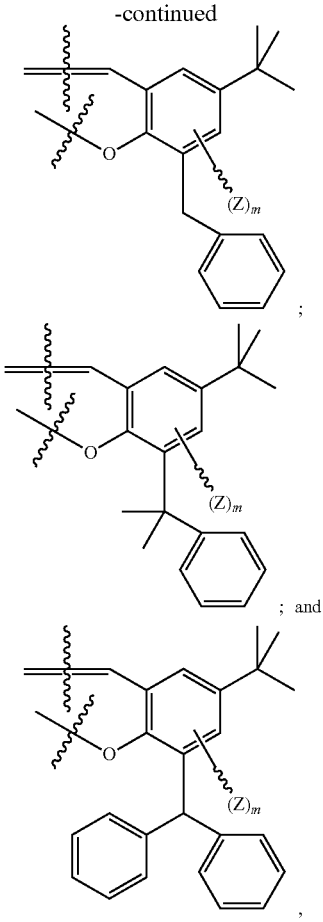

wherein ⁓⁓(Z)ₘ represents one or more independently-defined activating moieties which may be bonded to any one or more unsubstituted positions of the phenyl ring and wherein a total of at least two Z groups are present.

In certain embodiments, there is an activating moiety tethered to the position ortho to a metal-bound oxygen substituent of one of the salicylaldehyde-derived phenyl rings of a salen ligand as in formula IIIa-1:

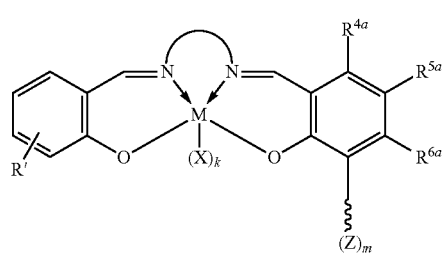

wherein:
M, X, k, R, R', and ⁓⁓(Z)ₘ are as defined above and described in classes and subclasses herein, and $R^{4a}$, $R^{5a}$, and $R^{6a}$ are each independently a ⁓⁓(Z)ₘ group, hydrogen, halogen, —OR, —NR₂, —SR, —CN, —NO₂, —SOR, —SO₂NR₂; —CNO, —NRSO₂R, —NCO, —N₃, —SiR₃; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur;

wherein any two adjacent $R^{4a}$, $R^{5a}$, and $R^{6a}$ groups can be taken together with intervening atoms to form one or more optionally substituted rings;

and wherein each m is independently an integer greater than 1.

In certain embodiments of compounds having formula $R^{4a}$, and $R^{6a}$ are each hydrogen, and $R^{5a}$, is optionally substituted $C_1$-$C_{20}$ aliphatic.

In certain embodiments of complexes IIIa-1, one of the phenyl rings comprising a salicylaldehyde-derived portion of a metal complex is selected from the group consisting of:

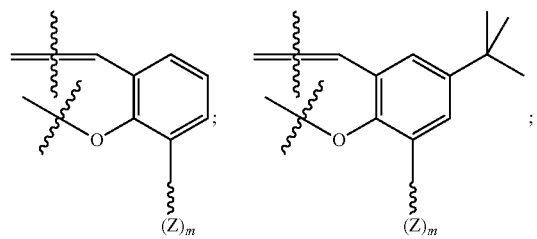

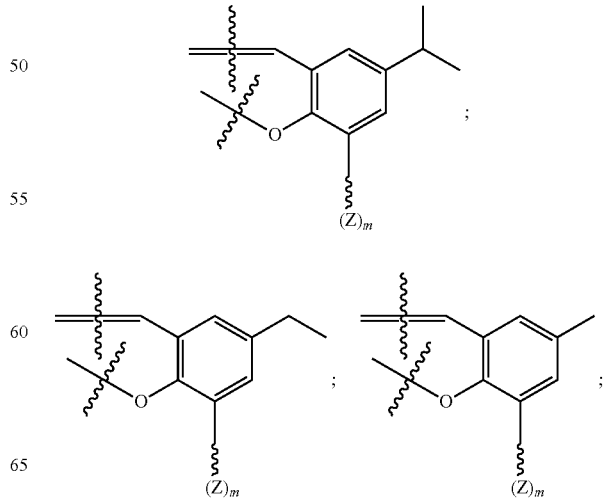

-continued

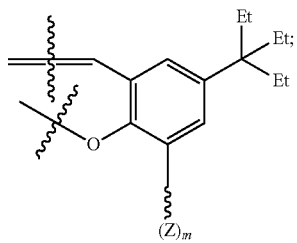

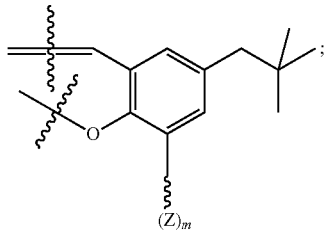

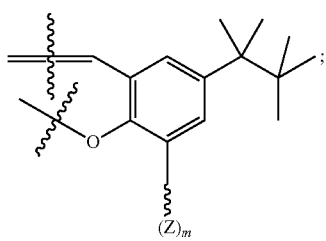

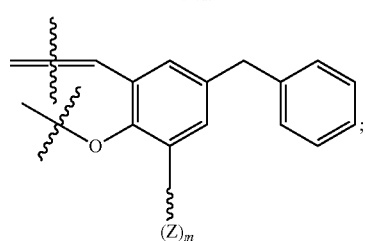

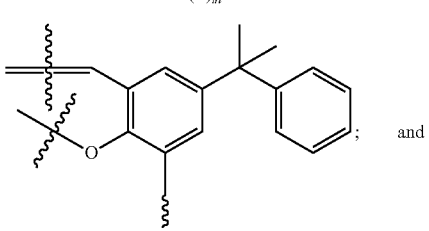

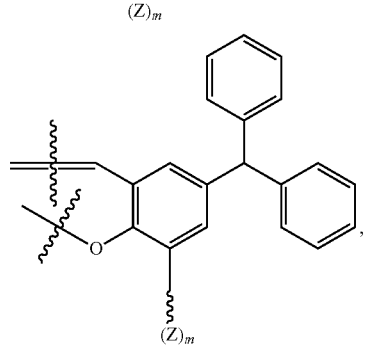

where ⁓⁓ (Z) is as defined above and described in classes and subclasses herein, and m is greater than 1.

In certain embodiments, there is an activating moiety tethered to the position para to the phenolic oxygen of one of the salicylaldehyde-derived phenyl rings of the salen ligand as in structure IVa:

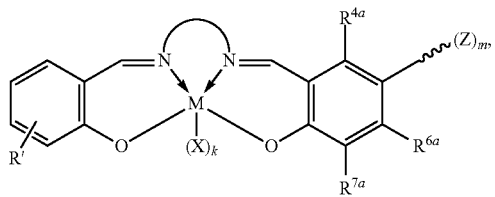

IVa where M, X, k, R', $R^{4a}$, $R^{6a}$, $R^{7a}$,

⌒, and ⁓⁓ $(Z)_m$ are as defined above and described in classes and subclasses herein.

In certain embodiments of compounds having formula IVa, $R^{4a}$ and $R^{6a}$ are hydrogen, and $R^{7a}$ is optionally substituted $C_1$-$C_{20}$ aliphatic.

In certain embodiments of metal complexes IVa, a phenyl ring comprising a salicylaldehyde-derived portion of a metal complex is selected from the group consisting of:

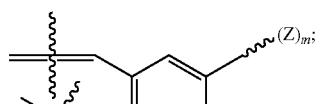

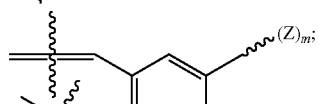

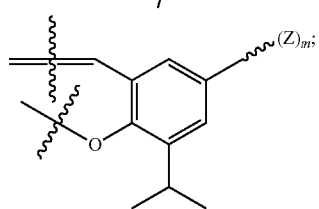

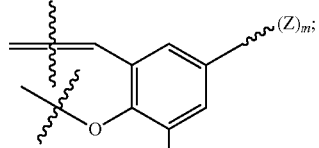

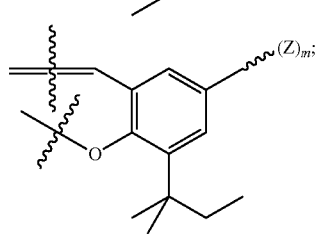

-continued

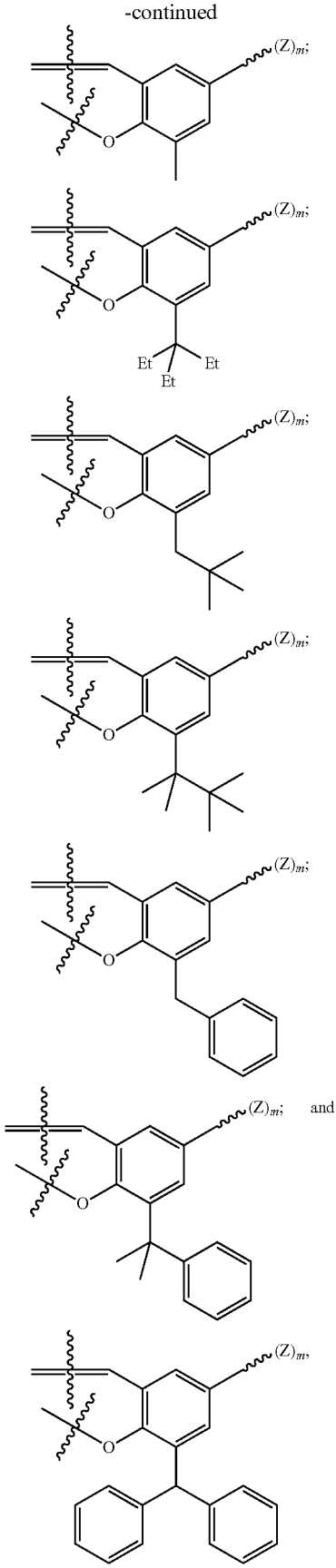

where ⎯⋀⋀⋀ (Z) is as defined above and described in classes and subclasses herein, and m is greater than 1.

In some embodiments, there is an activating moiety tethered to the position para to the imine substituent of one of the salicylaldehyde-derived phenyl rings of a salen ligand as in formulae Va:

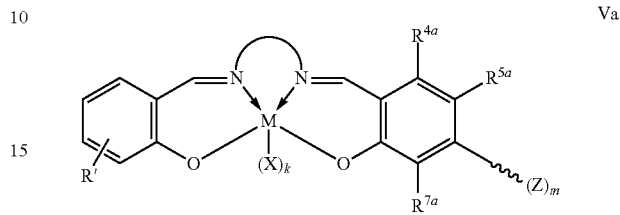

Va where M, X, k, R', $R^{4a}$, $R^{5a}$, $R^{7a}$,

⌢, and ⎯⋀⋀⋀ $(Z)_m$ are as defined above and described in classes and subclasses herein.

In certain embodiments of compounds having formula Va, $R^4$ is hydrogen, and each of $R^{5a}$ and $R^{7a}$ is, independently, hydrogen or optionally substituted $C_1$-$C_{20}$ aliphatic.

In certain embodiments of metal complexes Va, one of the phenyl rings comprising a salicylaldehyde-derived portion of a metal complex is selected from the group consisting of:

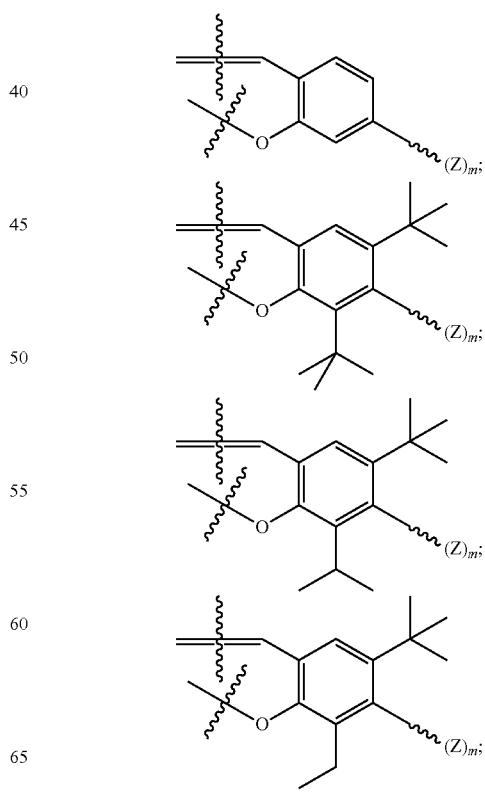

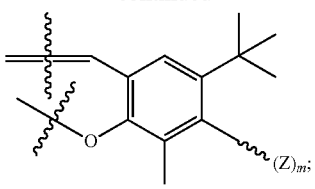
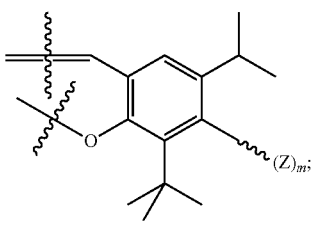
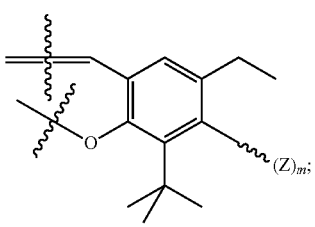
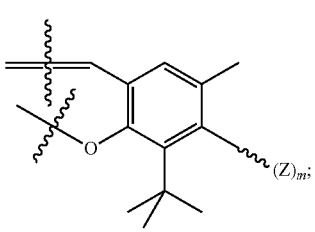
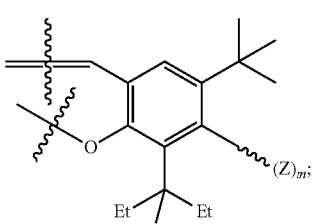
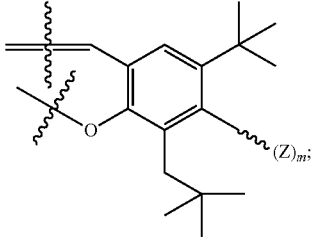
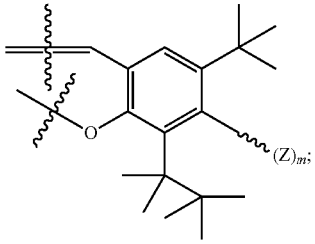
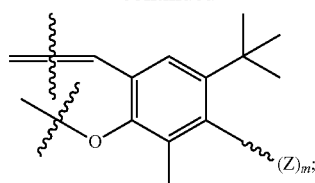
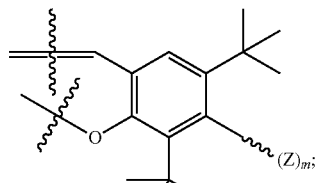
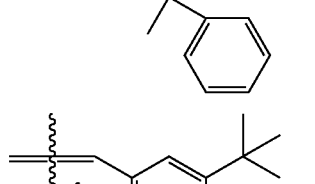
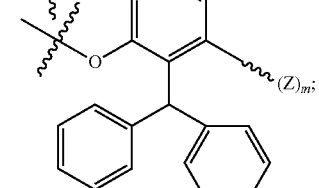
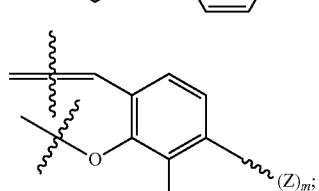
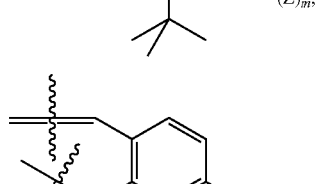
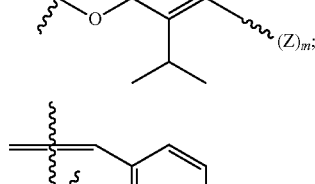
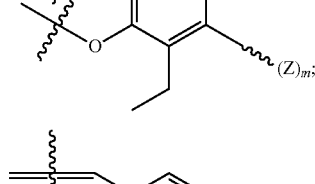
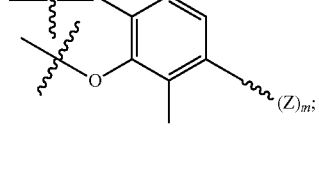

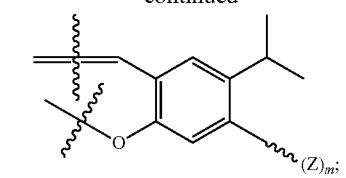

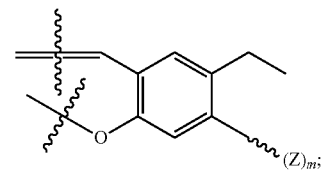

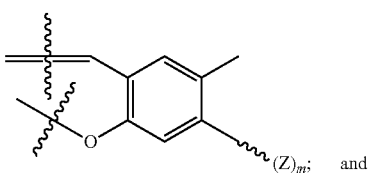 and

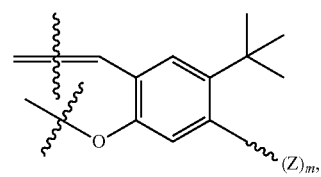

where —⌇⌇ (Z) is as defined above and described in classes and subclasses herein, and m is greater than 1.

In some embodiments, there is an activating moiety tethered to the position ortho to the imine substituent of one or both of the salicylaldehyde-derived phenyl rings of a salen ligand as in formula VIa:

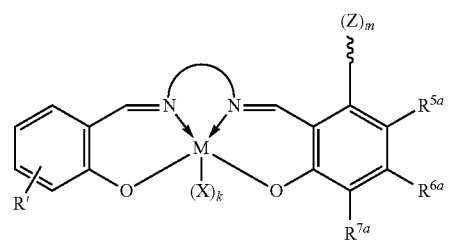

or, where X, k, M, R', $R^{5a}$, $R^{6a}$, $R^{7a}$,

⌒, and —⌇⌇ $(Z)_m$ are as defined above and described in classes and subclasses herein.

In certain embodiments of compounds having formulae VIa, $R^{6a}$ is hydrogen, and each of $R^{5a}$ and $R^{7a}$ is, independently, hydrogen or optionally substituted $C_1$-$C_{20}$ aliphatic.

In certain embodiments of metal complexes VIa one of the phenyl rings is selected from the group consisting of:

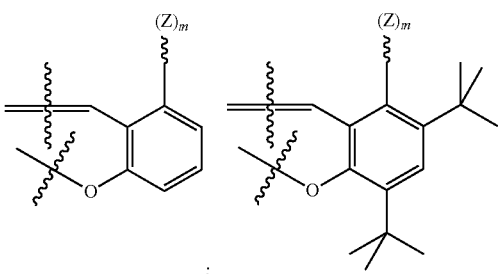

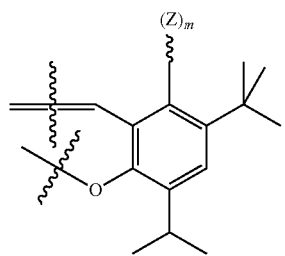

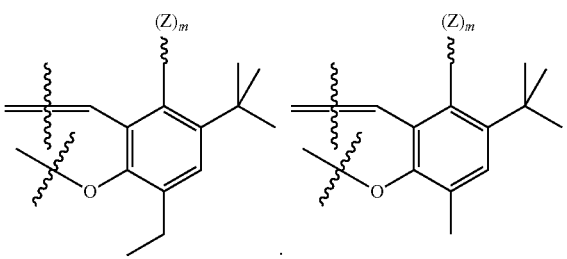

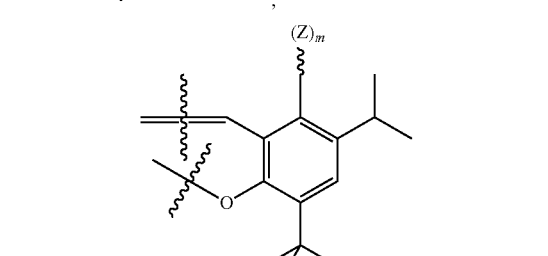

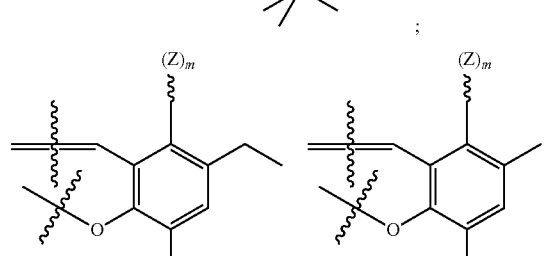

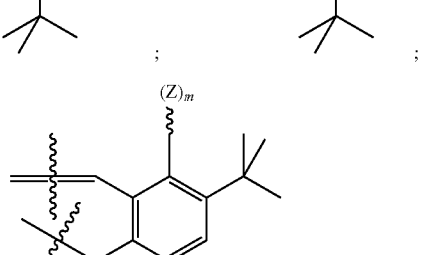

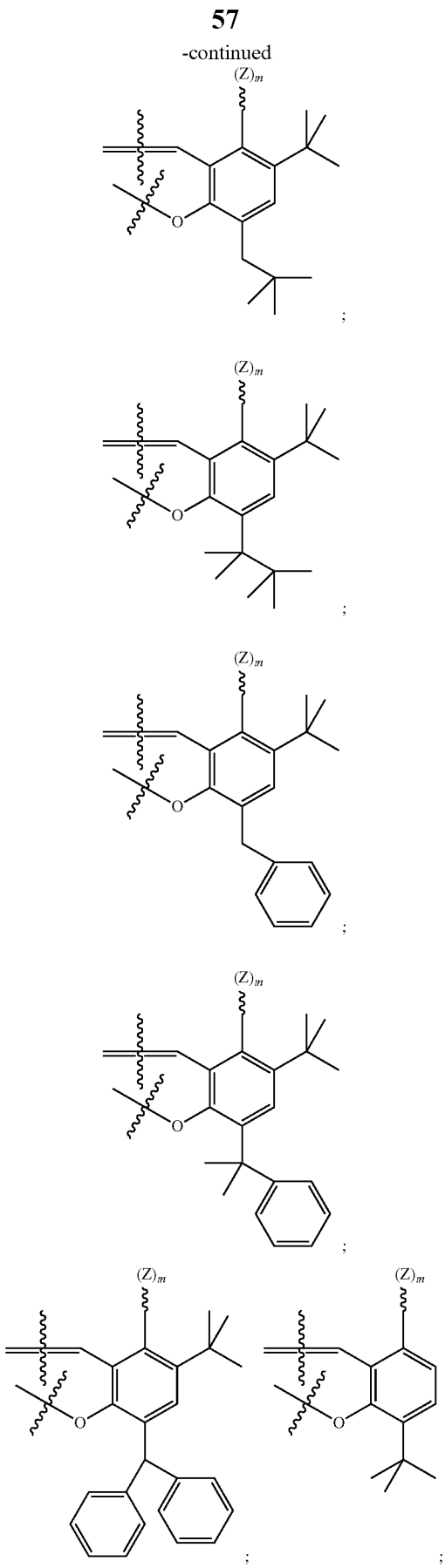
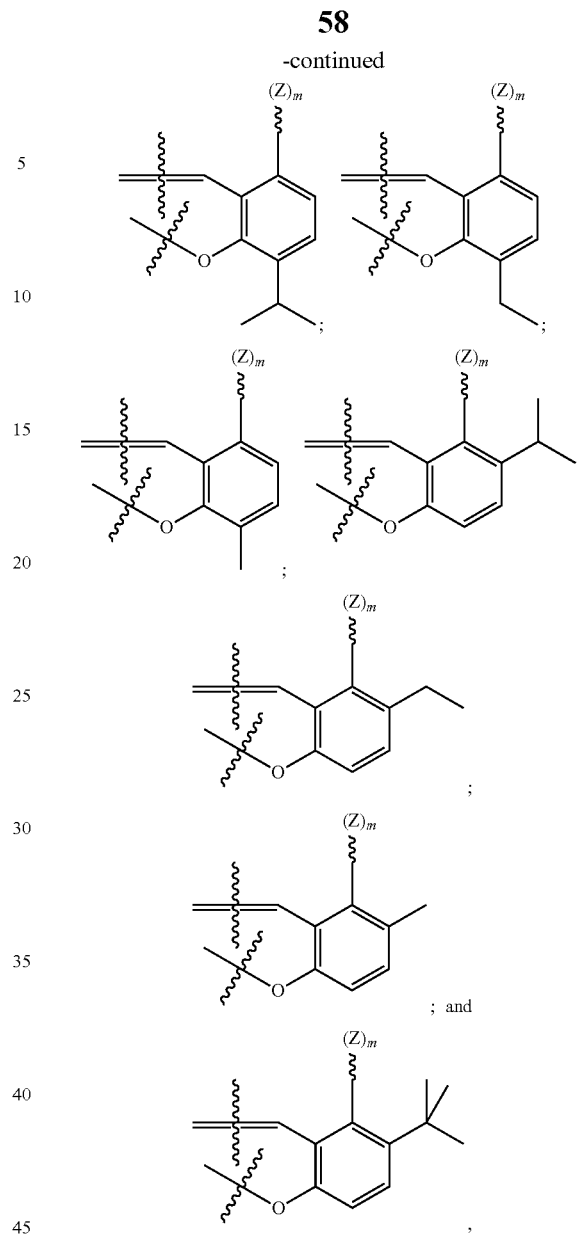
where ⌇⌇ (Z) is as defined above and described in classes and subclasses herein, and m is greater than 1.
In some embodiments, there are activating moieties tethered to the positions ortho and para to the phenolic oxygen of one salicylaldehyde-derived phenyl ring of a salen ligand as in formula VIIa:
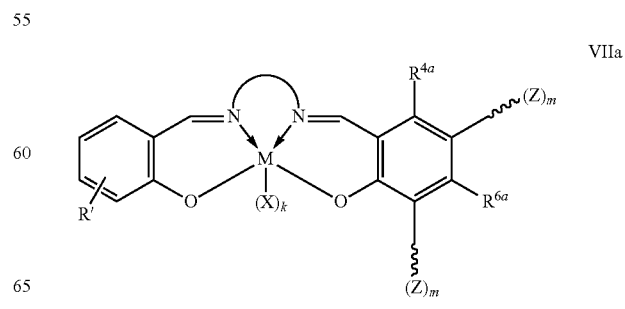

where M, X, k, R', $R^{4a}$, $R^{6a}$, and ⁓ $(Z)_m$ are as defined above and described in classes and subclasses herein.

In certain embodiments of compounds having formula VIIa each of $R^{6a}$ and $R^{4a}$ is, independently, hydrogen or optionally substituted $C_1$-$C_{20}$ aliphatic.

In certain embodiments of compounds having formula VIIa, each $R^{6a}$ and $R^{4a}$ is hydrogen.

In some embodiments, there are activating moieties tethered to the positions ortho and para to the imine substituent of one of the salicylaldehyde-derived phenyl rings of a salen ligand as in formula VIIIa:

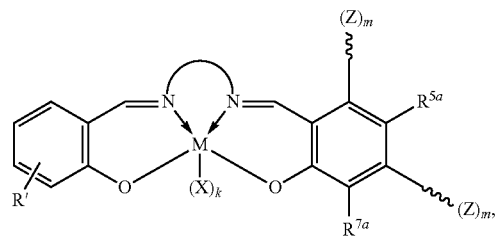

VIIIa where X, k, M, R', $R^{5a}$, $R^{7a}$, and ⁓ $(Z)_m$ are as defined above and described in classes and subclasses herein.

In certain embodiments of compounds having formula VIIIa each of $R^{5a}$ and $R^{7a}$ is independently hydrogen or substituted $C_1$-$C_{20}$ aliphatic.

In certain embodiments of the present invention, metal complexes of structure VIIIa one of the phenyl rings comprising the salicylaldehyde-derived portion of a metal complex is independently selected from the group consisting of:

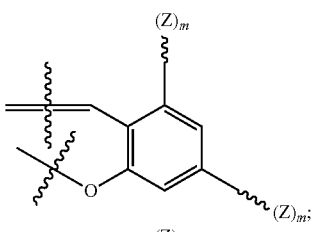
;

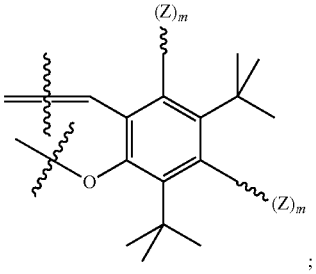
;

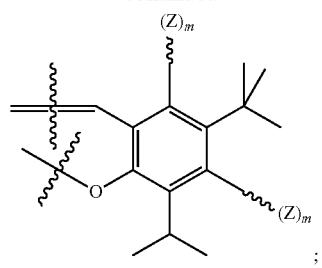
;

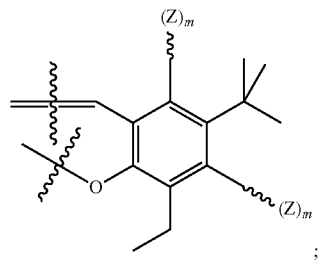
;

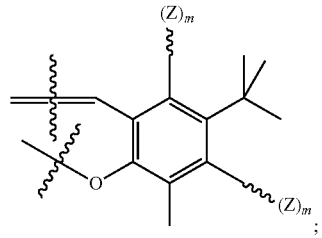
;

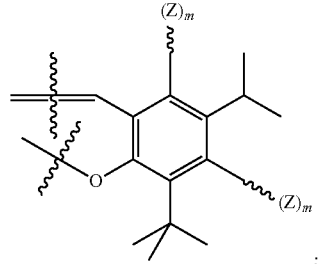
;

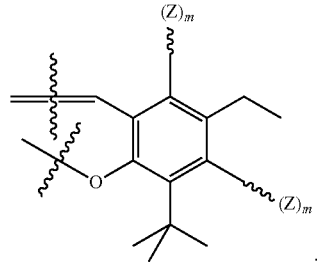
;

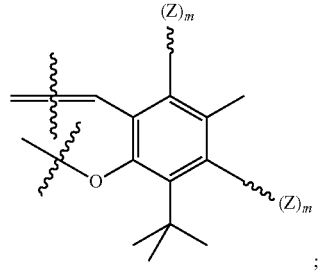
;

61
-continued
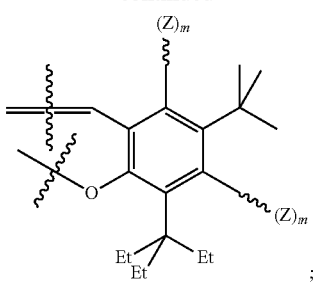
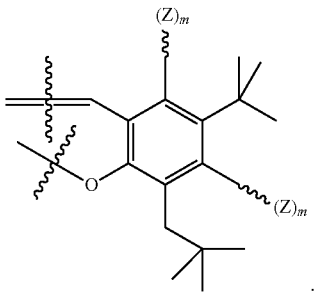
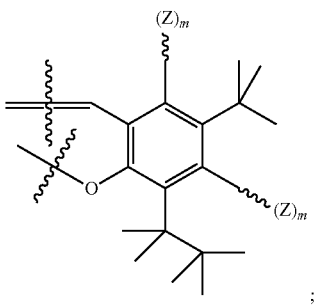
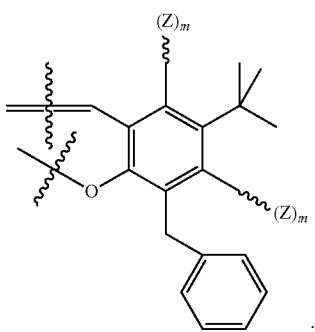
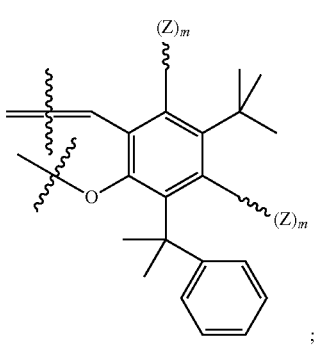
62
-continued
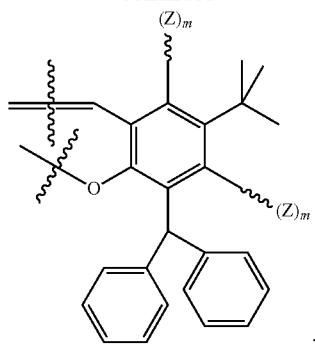
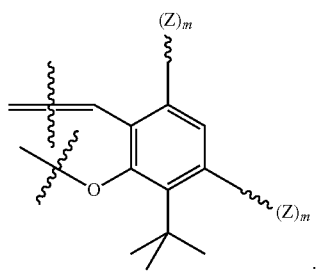
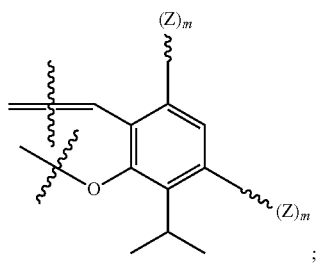
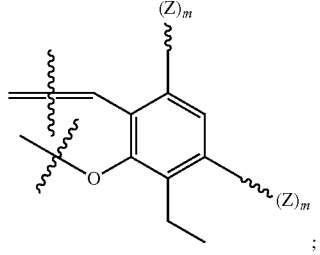
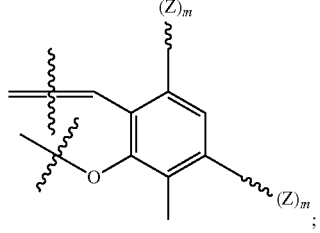
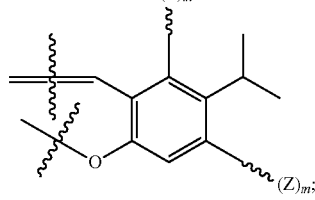

-continued

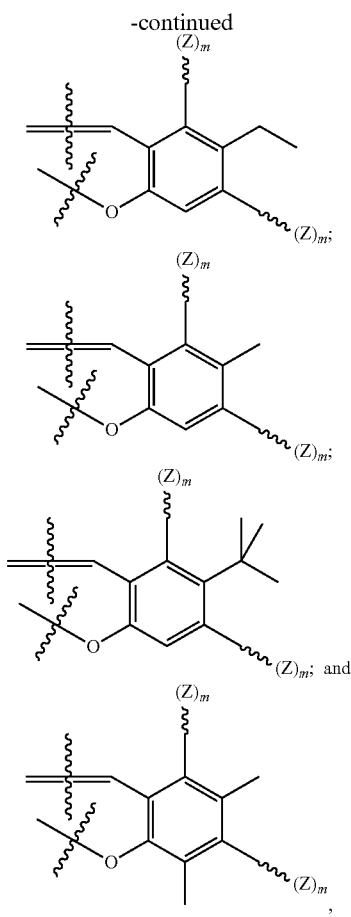

where ⸻⟿ (Z) is as defined above and described in classes and subclasses herein and each m is, independently, 1, 2, 3, or 4.

As shown above, the two phenyl rings derived from salicylaldehyde in the core salen structures are not the same. The phenyl ring not bearing any ⸻⟿ (Z)$_m$ groups may be substituted or unsubstituted. If substituted, one or more R' groups may be present as described above and in the examples and embodiments herein. In certain embodiments, the phenyl ring not bearing any ⸻⟿ (Z)$_m$ groups conforms to the structure:

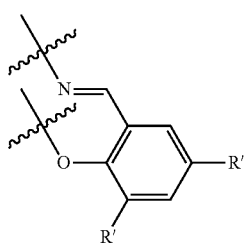

Where each R' group is the same or different.

In certain embodiments, the phenyl ring not bearing any ⸻⟿ (Z)$_m$ groups is substituted with one or two optionally substituted C$_{1-20}$ aliphatic groups. In certain embodiments, the phenyl ring not bearing any ⸻⟿ (Z)$_m$ groups is substituted with one optionally substituted C$_{1-20}$ aliphatic group. In certain embodiments, the optionally substituted C$_{1-20}$ aliphatic group is at the position ortho to the phenol. In certain the optionally substituted C$_{1-20}$ aliphatic group is at the position para to the phenol. In certain embodiments, the phenyl ring not bearing any ⸻⟿ (Z)$_m$ groups is substituted with two optionally substituted C$_{1-20}$ aliphatic groups. In certain embodiments, the two optionally substituted C$_{1-20}$ aliphatic groups are the same. In certain embodiments, the two optionally substituted C$_{1-20}$ aliphatic groups are different. In certain embodiments, the two optionally substituted C$_{1-20}$ aliphatic groups are at the positions ortho and para to the phenol.

In certain embodiments, the phenyl ring not bearing any ⸻⟿ (Z)$_m$ groups is selected from the group consisting of:

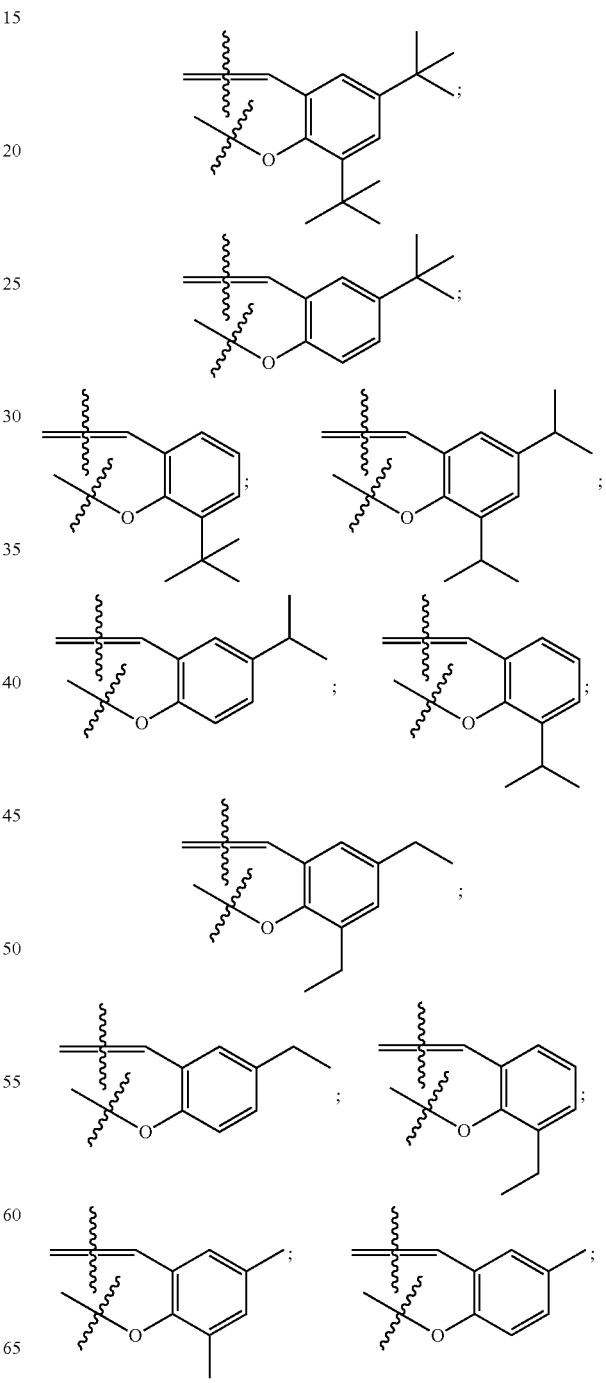

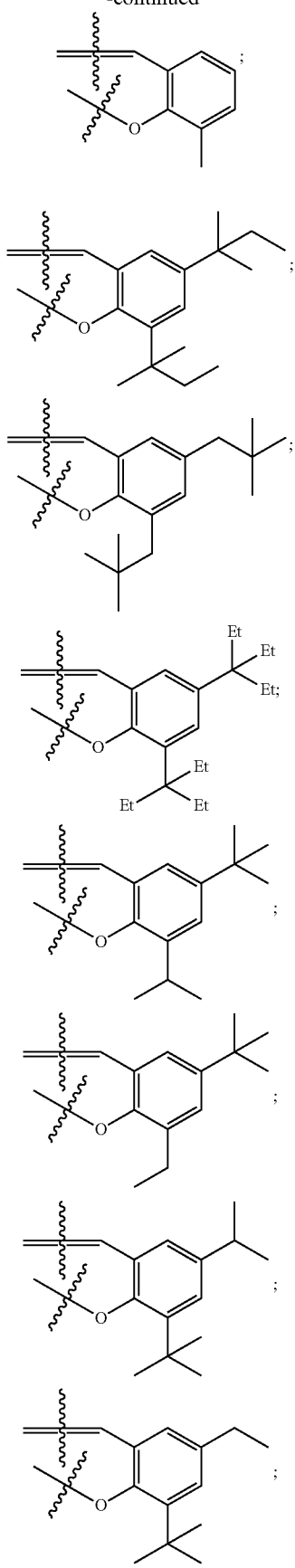
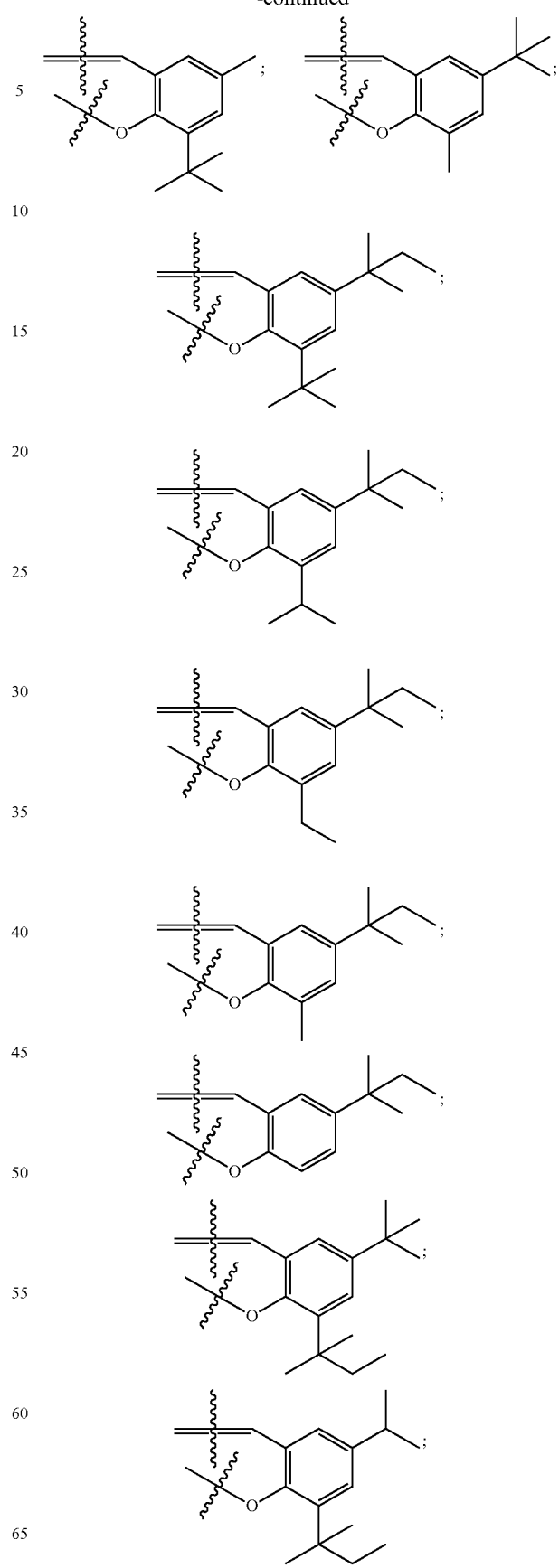

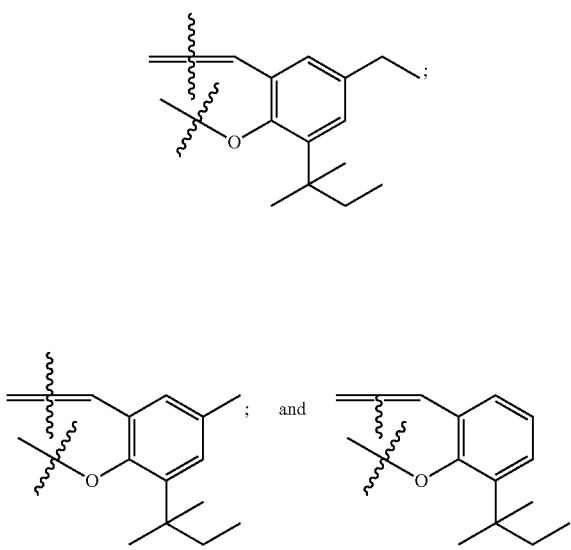
In certain embodiments, metallosalenate complexes of the present invention include, but are not limited to those in Table 1 below:
TABLE 1⊥
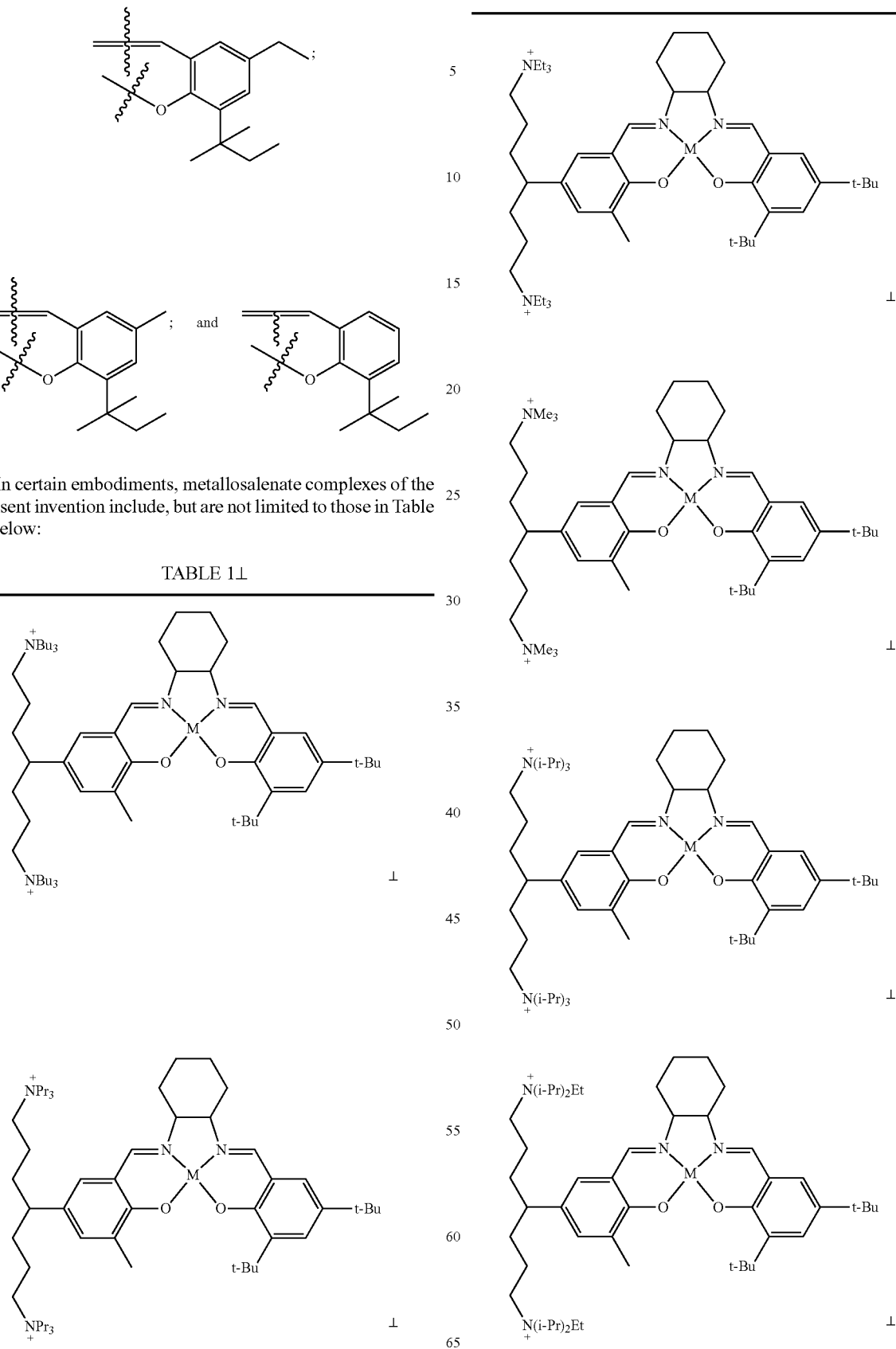

TABLE 1⊥-continued
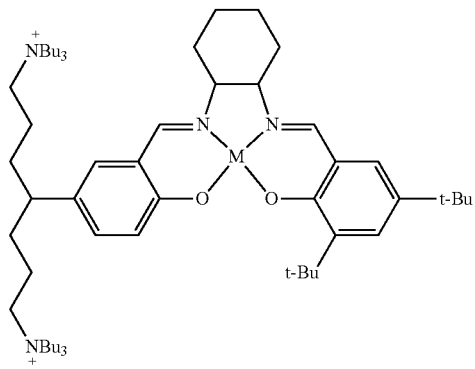
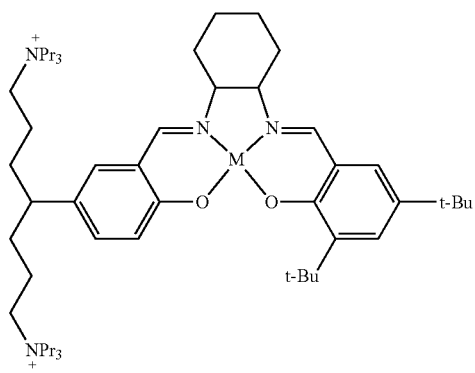
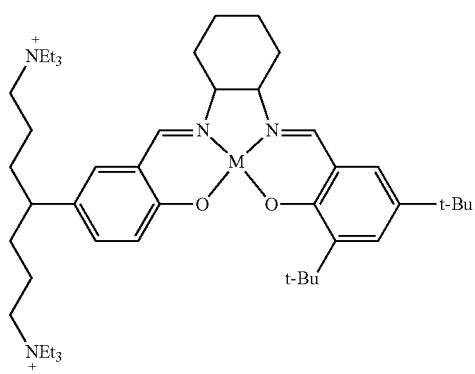
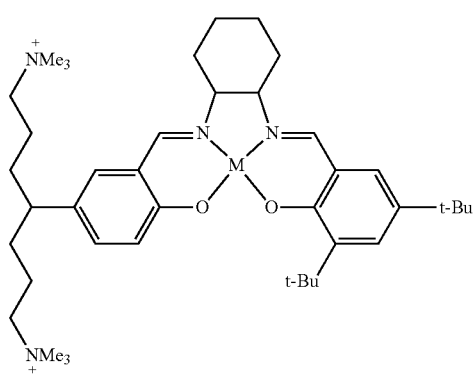
TABLE 1⊥-continued
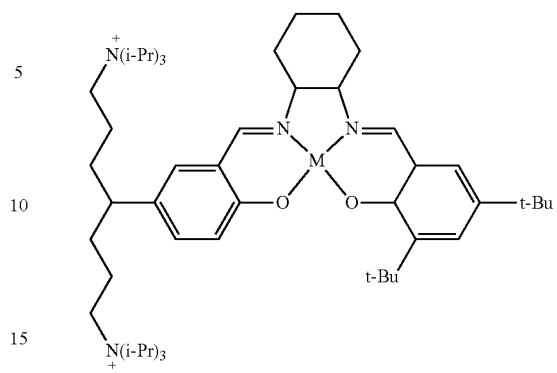
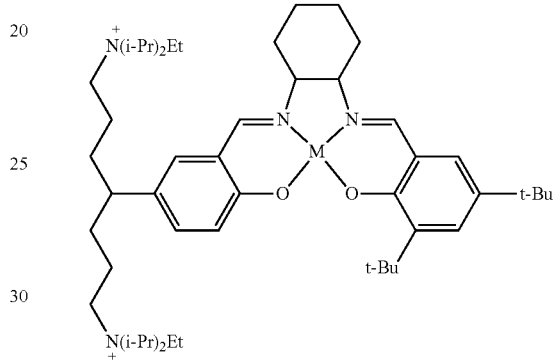
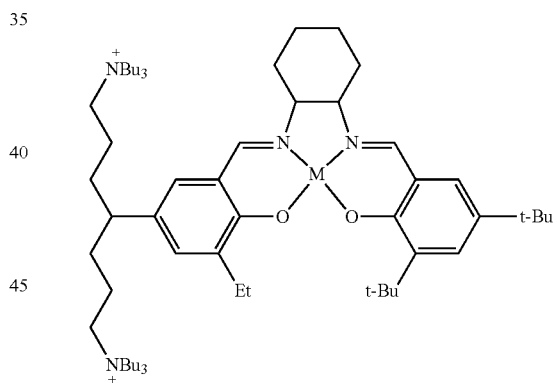
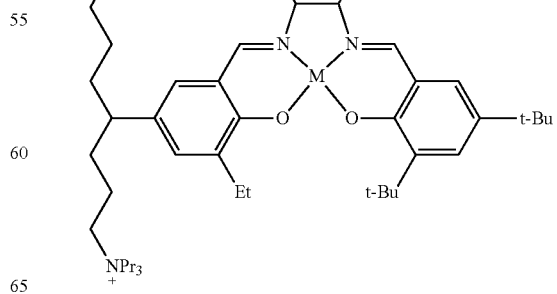

TABLE 1⊥-continued
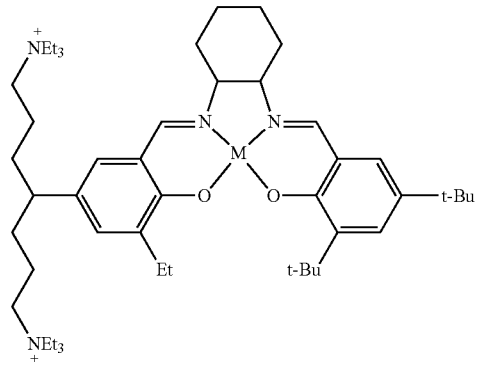
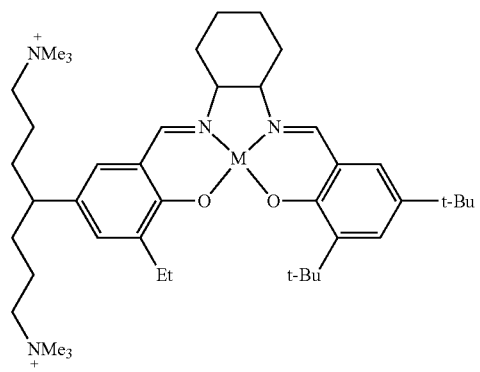
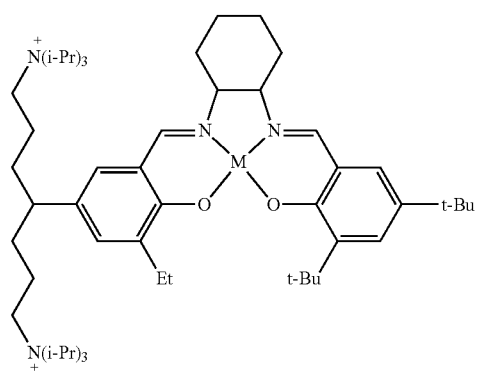
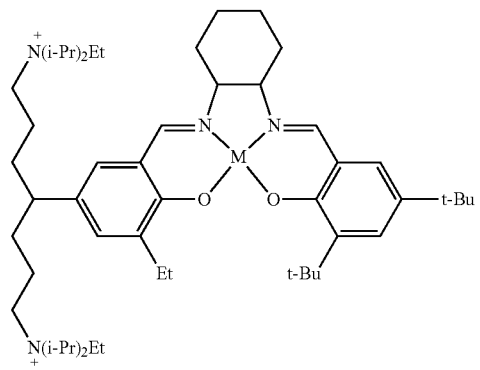
TABLE 1⊥-continued
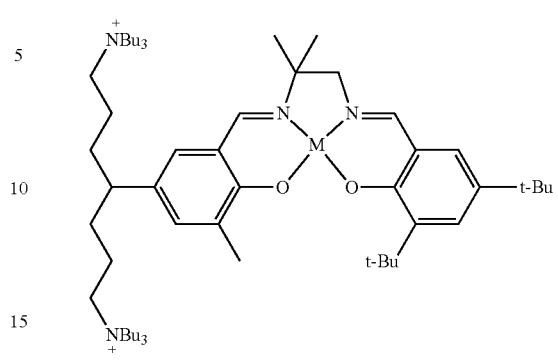
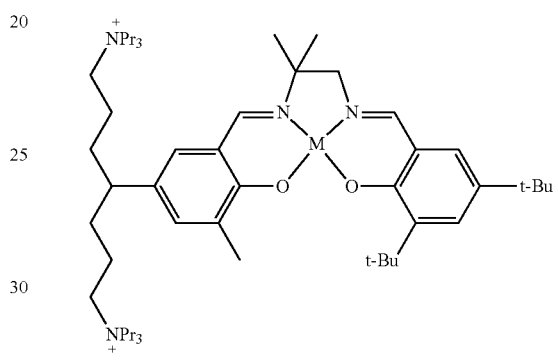
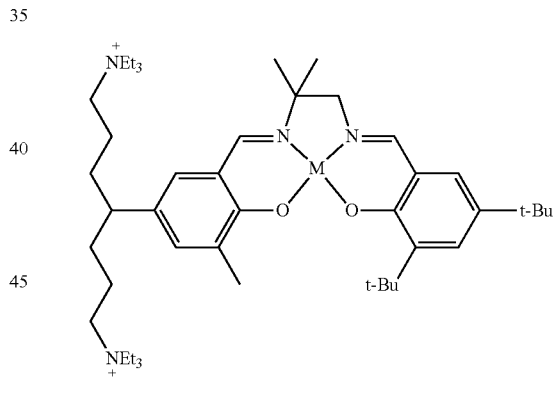
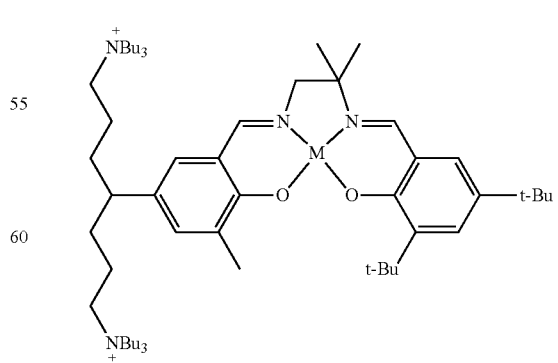

TABLE 1⊥-continued
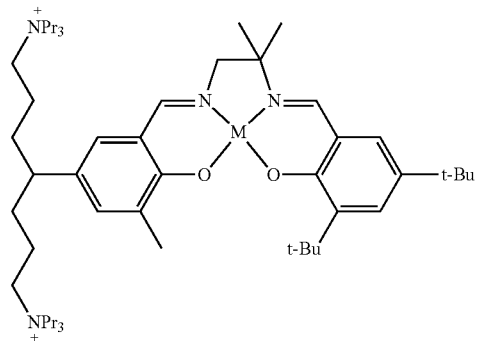
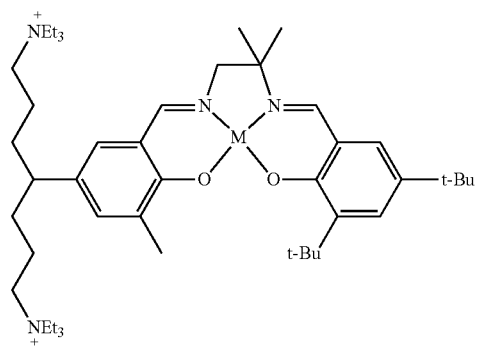
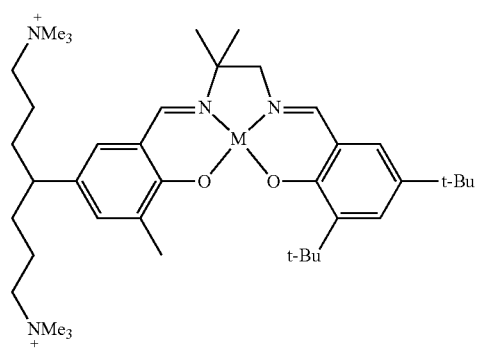
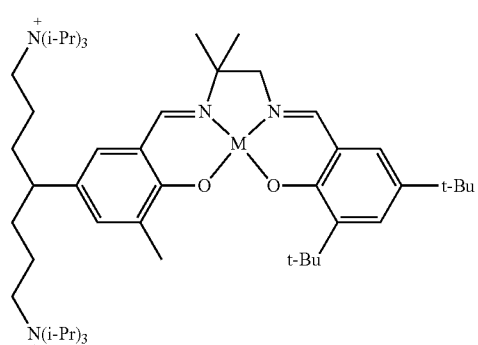
TABLE 1⊥-continued
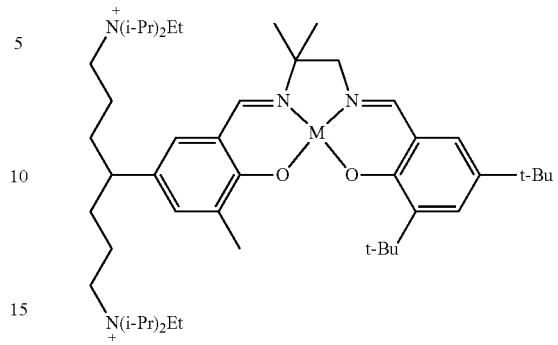
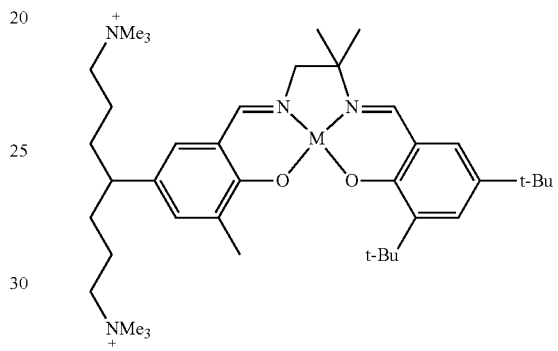
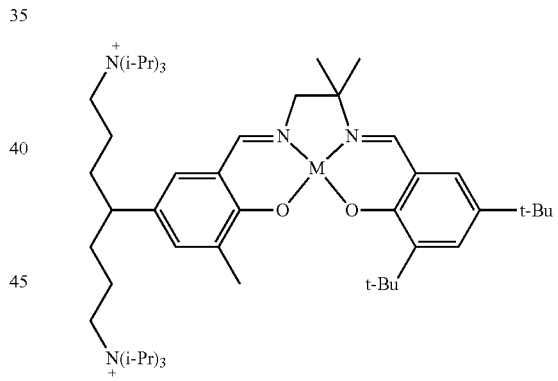
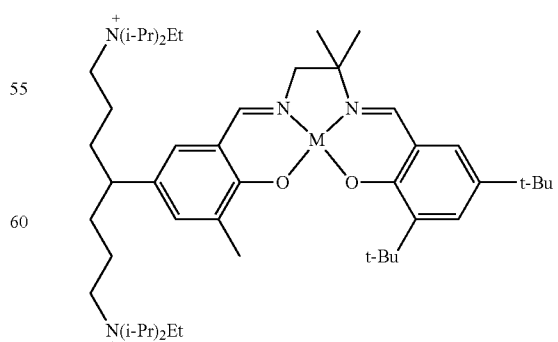

TABLE 1⊥-continued
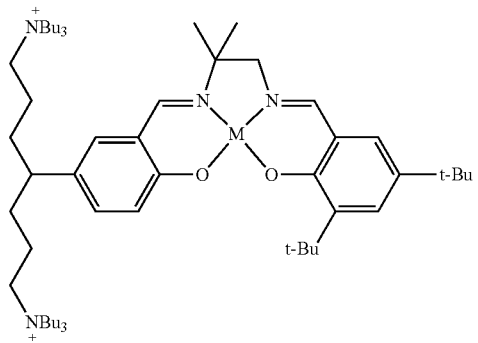
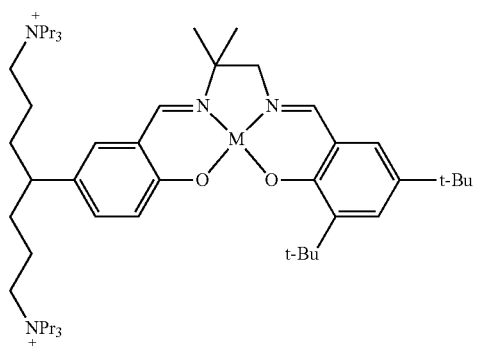
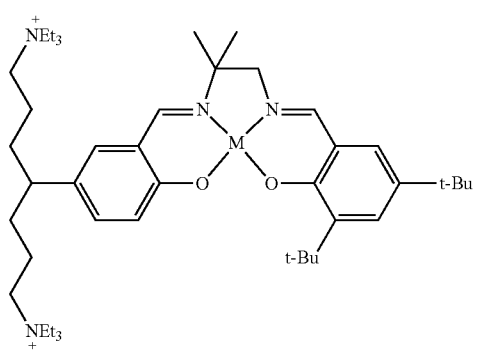
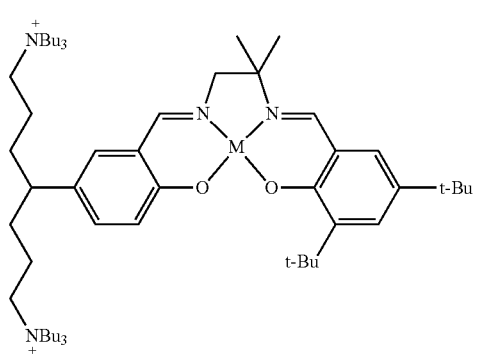
TABLE 1⊥-continued
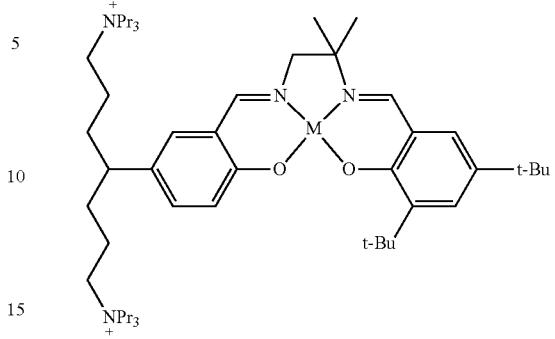
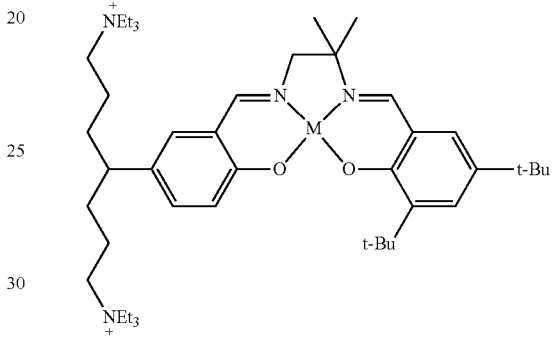
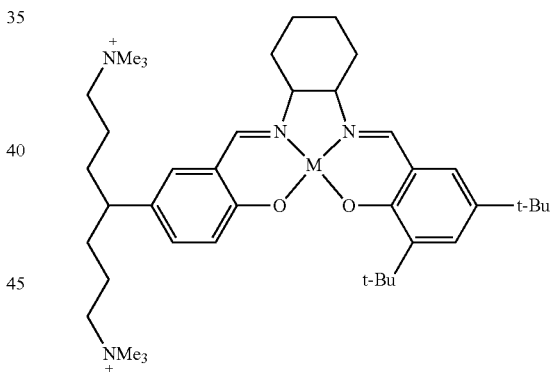
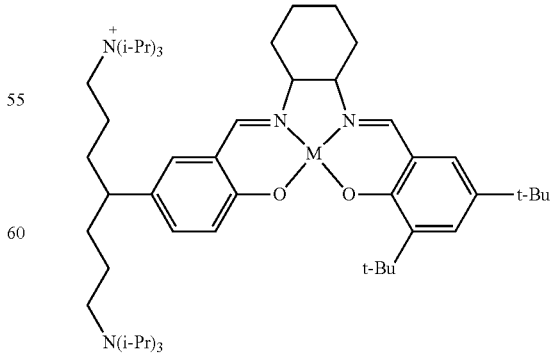

TABLE 1⊥-continued
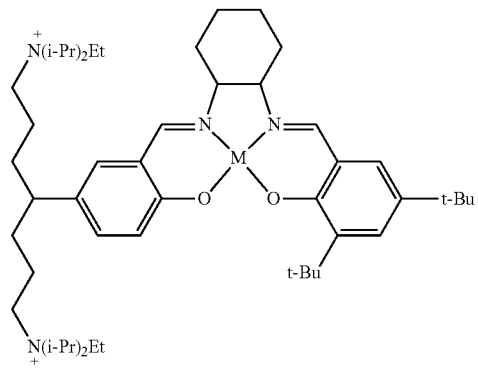
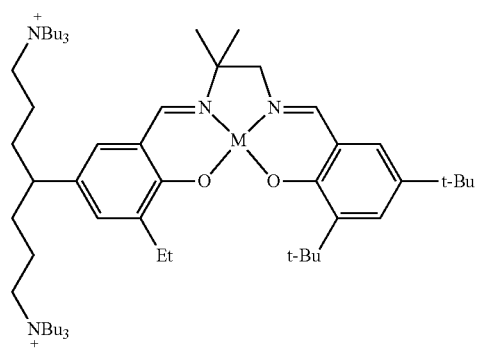
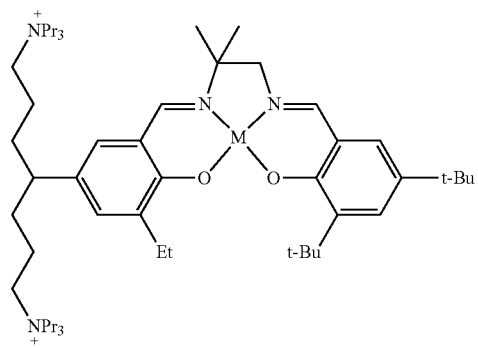
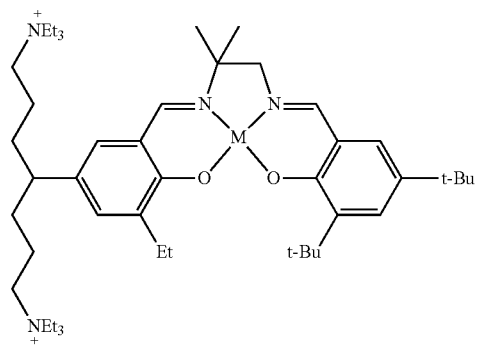
TABLE 1⊥-continued
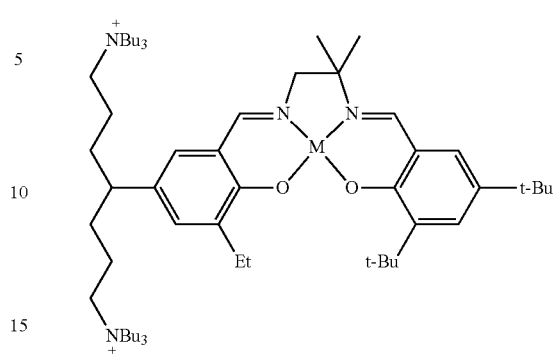
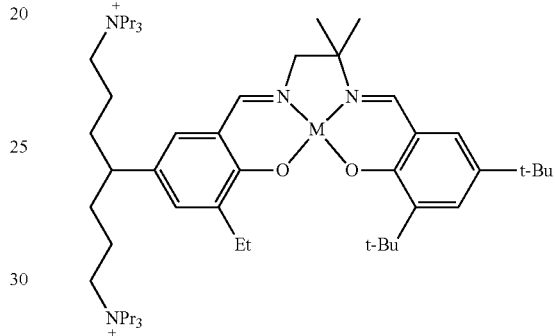
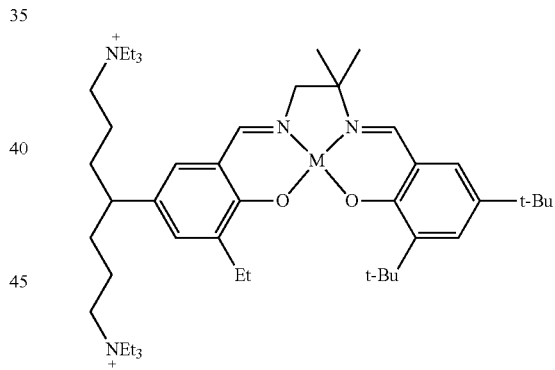
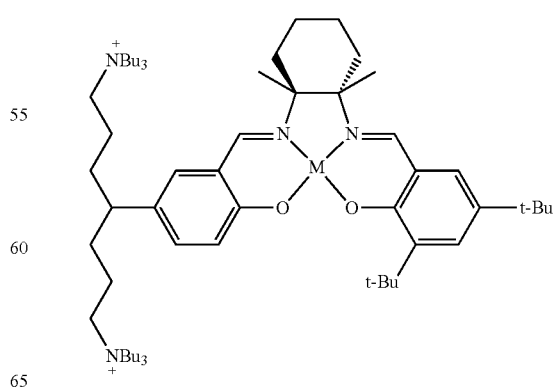

TABLE 1⊥-continued
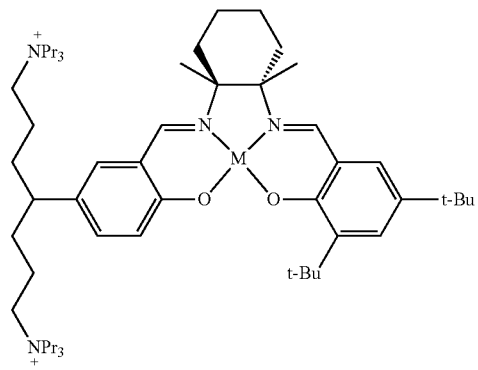
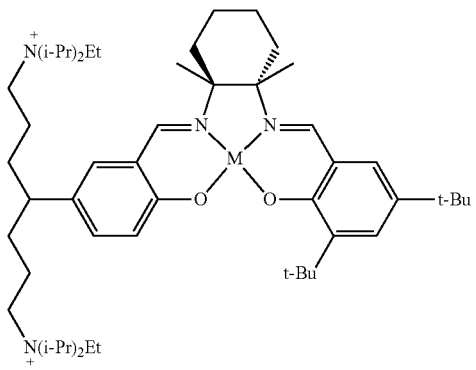
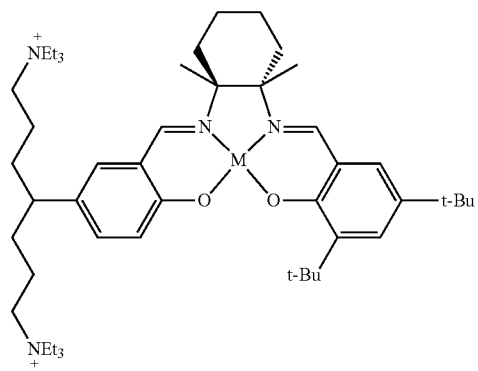
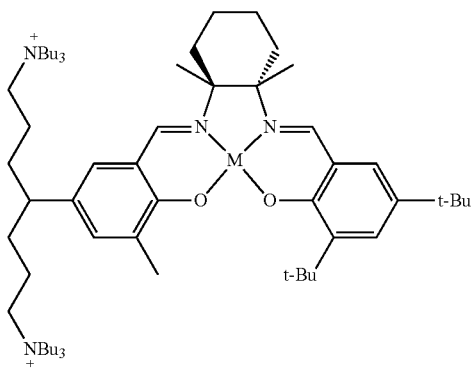
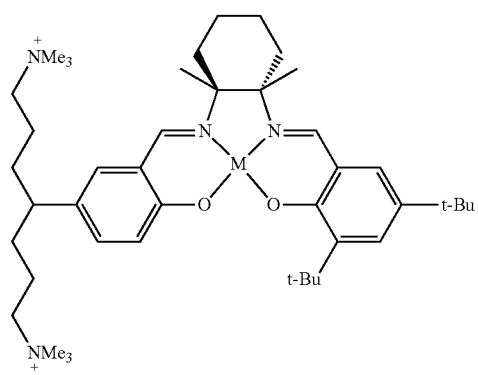
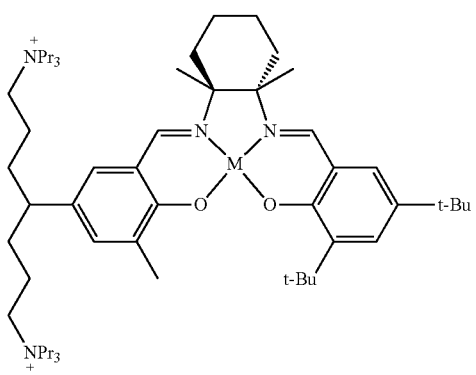
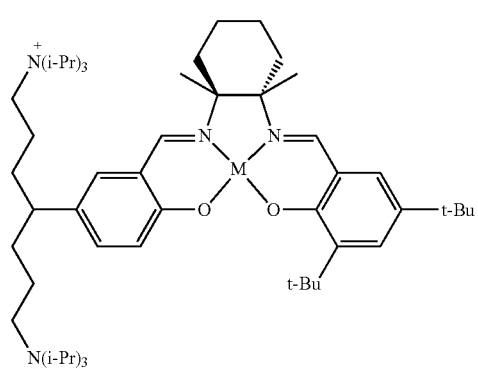
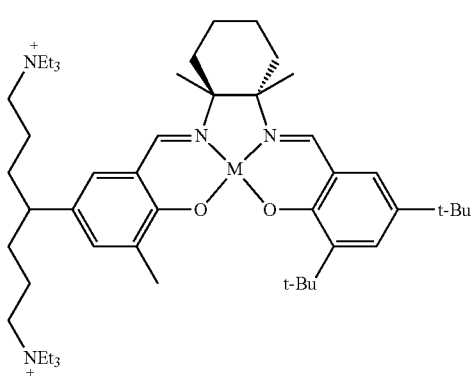

TABLE 1-continued
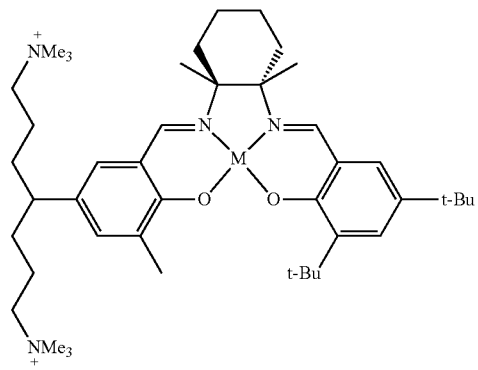
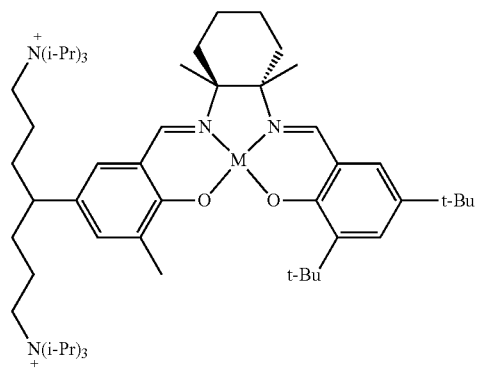
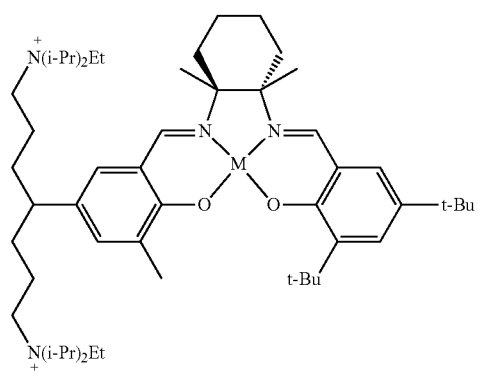
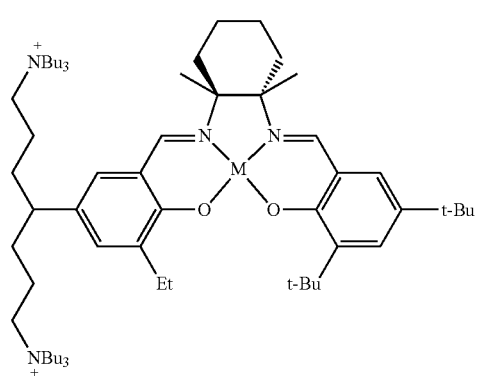
TABLE 1-continued
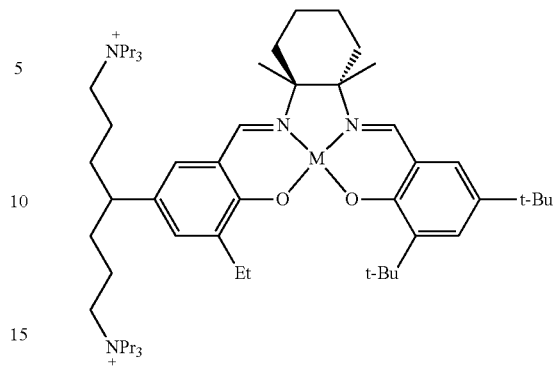
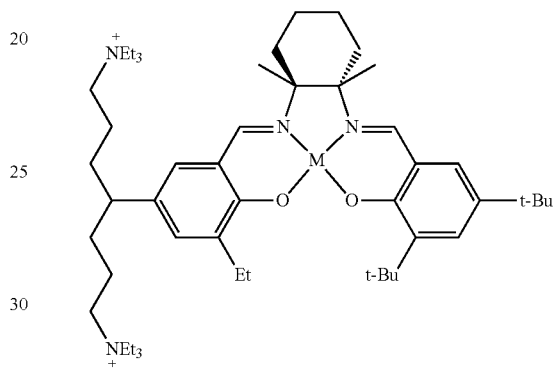
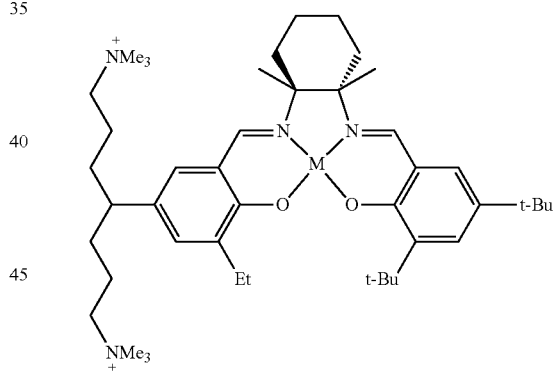
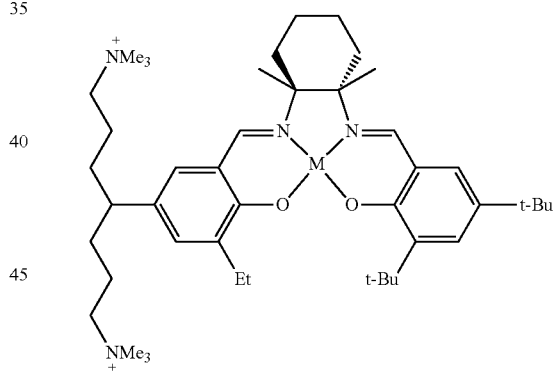

TABLE 1⊥-continued
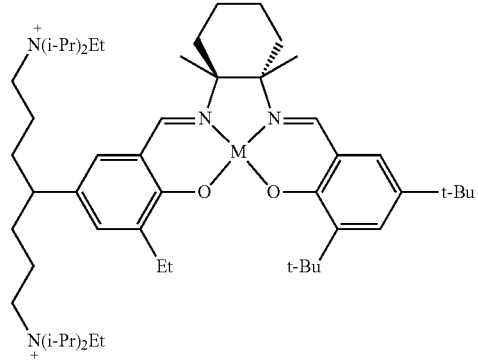
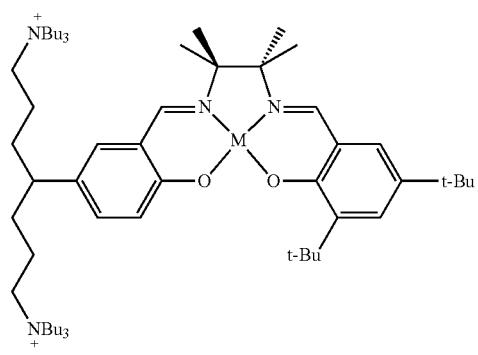
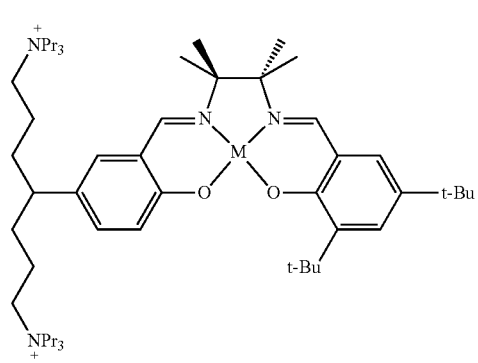
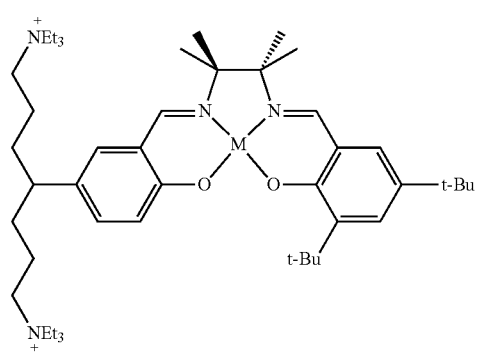
TABLE 1⊥-continued
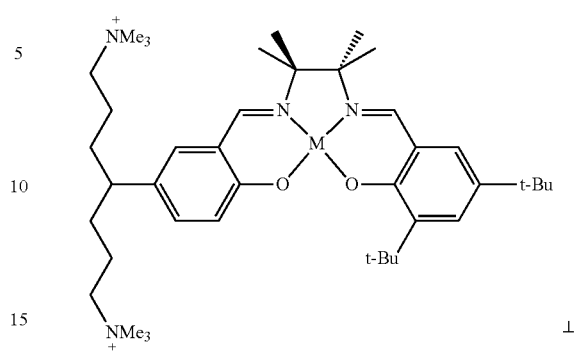
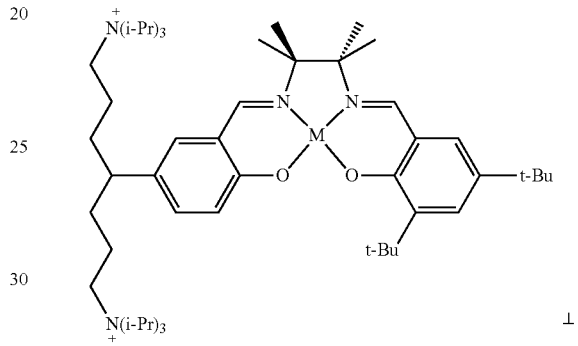
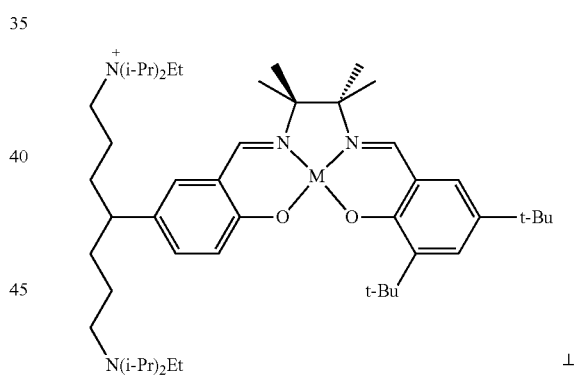
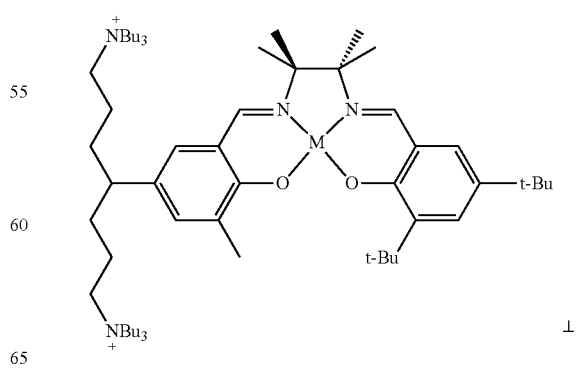

TABLE 1⊥-continued
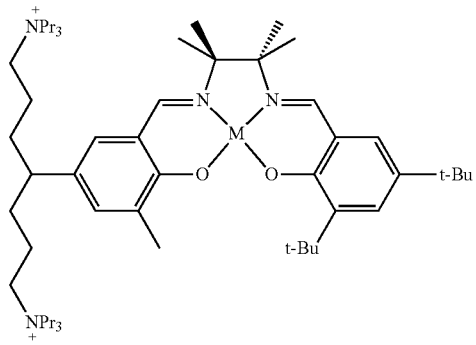
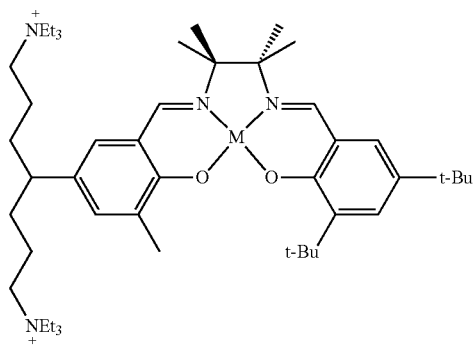
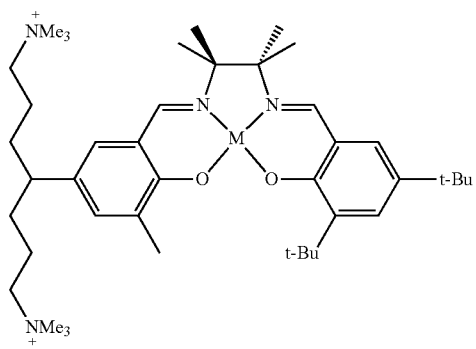
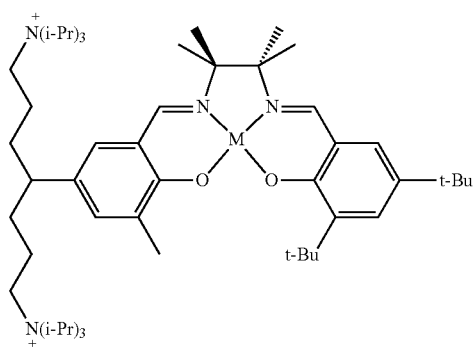
TABLE 1⊥-continued
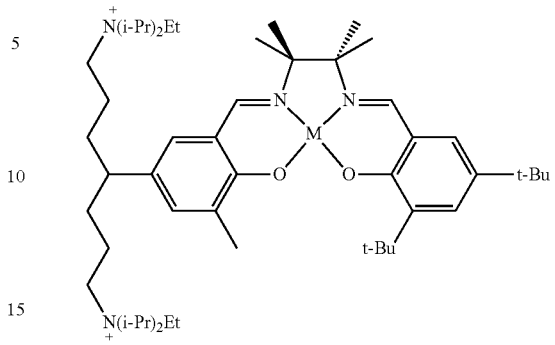
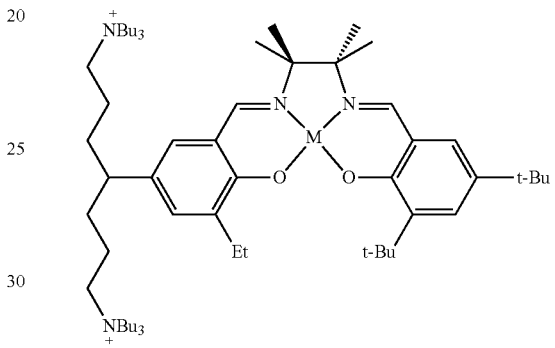
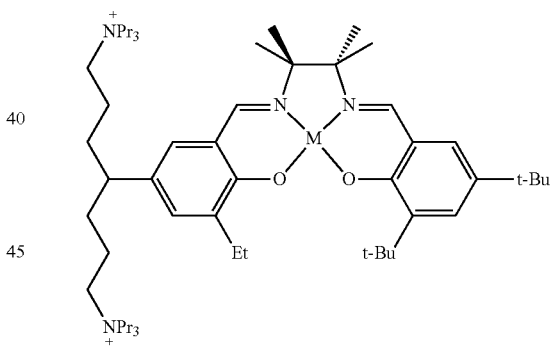
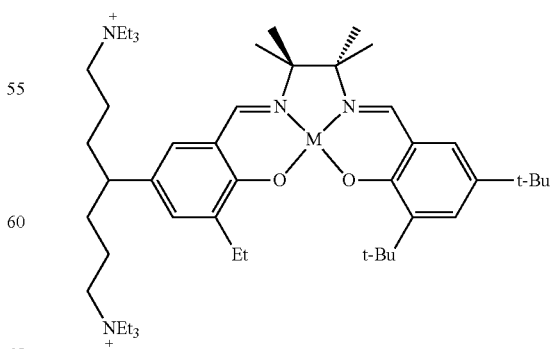

TABLE 1⊥-continued
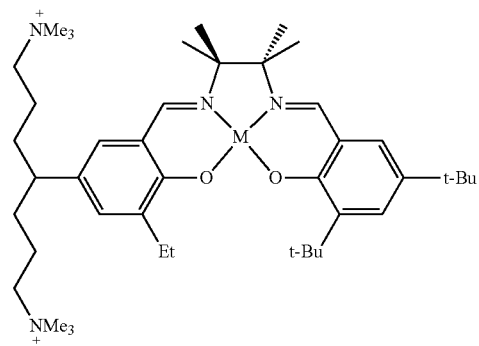
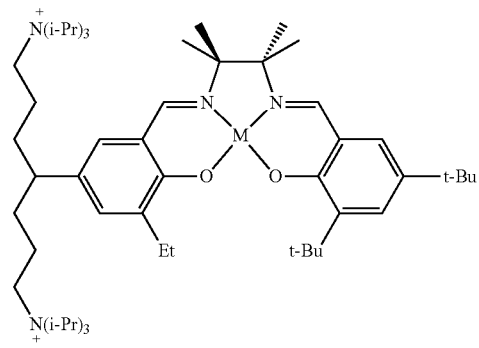
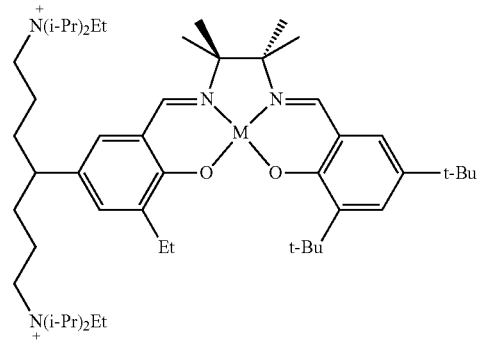
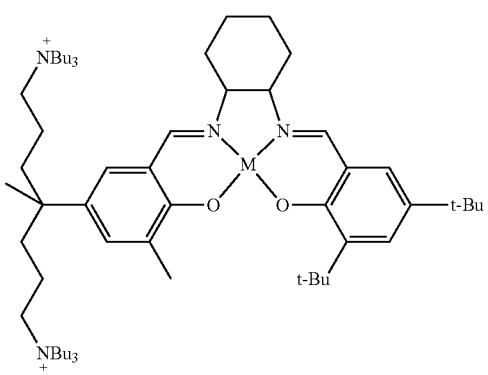
TABLE 1⊥-continued
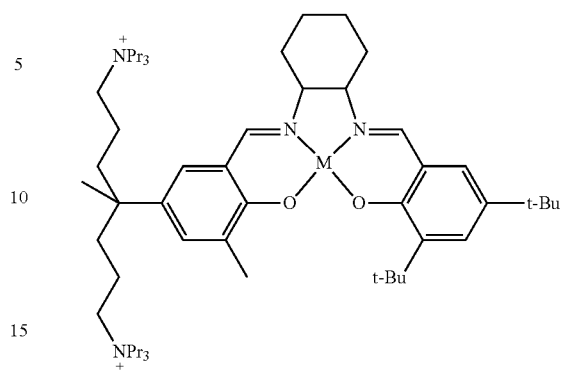
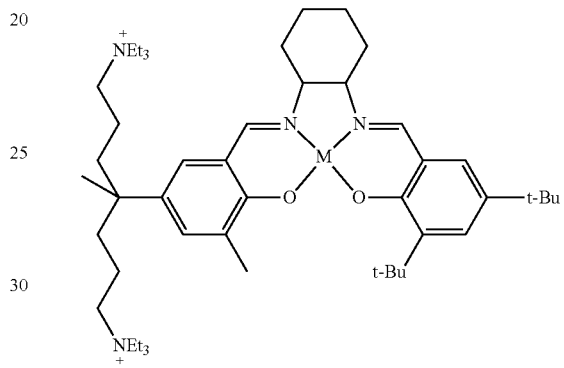
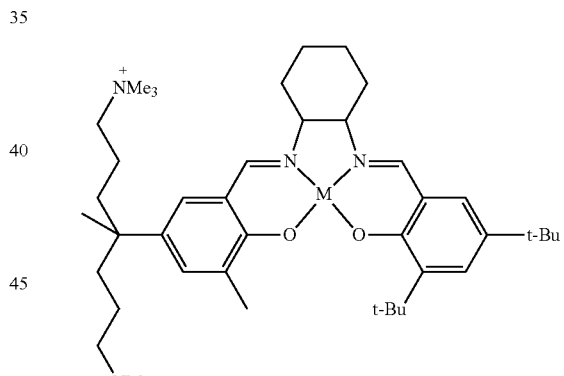
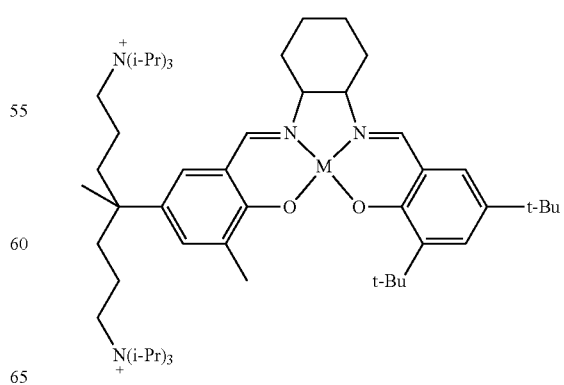

TABLE 1⊥-continued
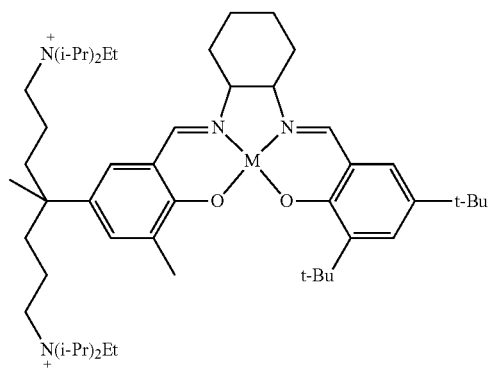
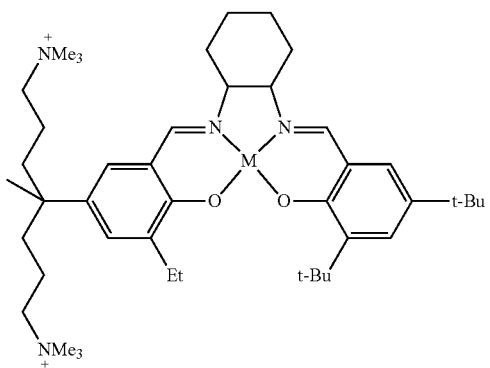
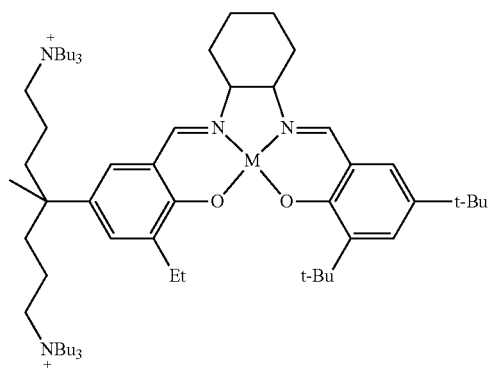
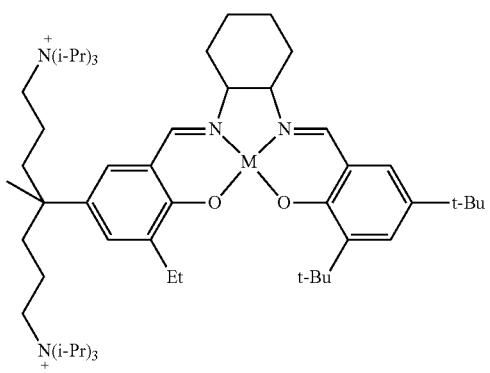
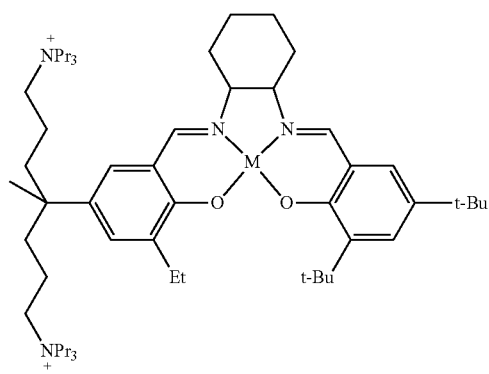
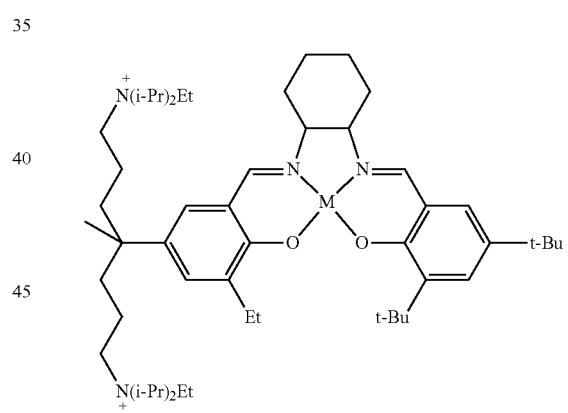
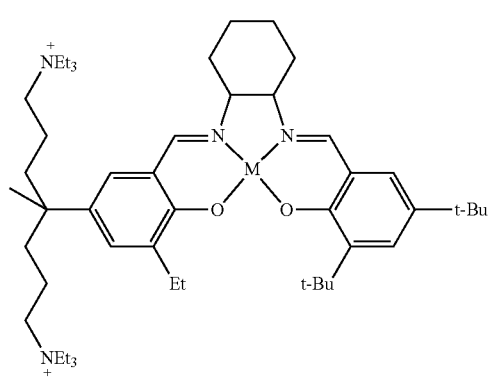
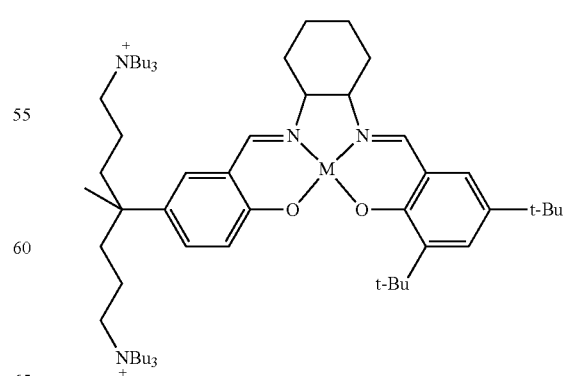

TABLE 1⊥-continued
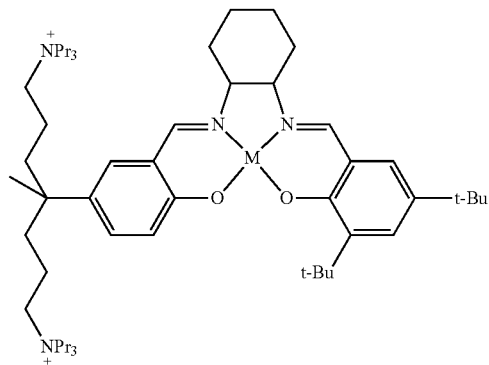
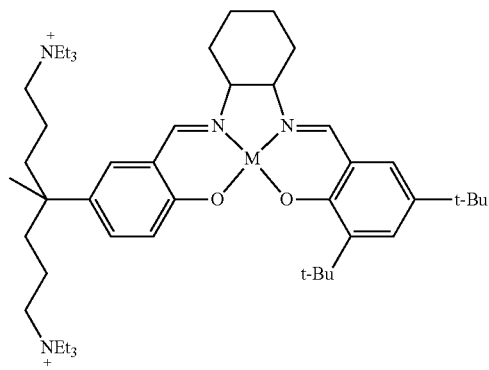
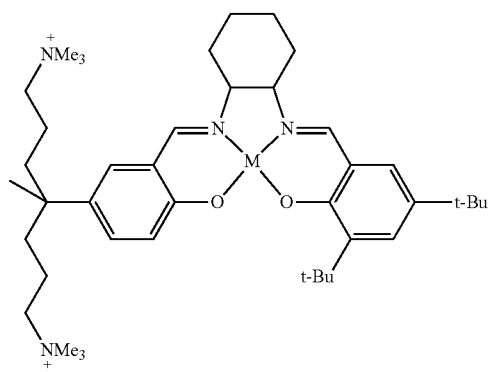
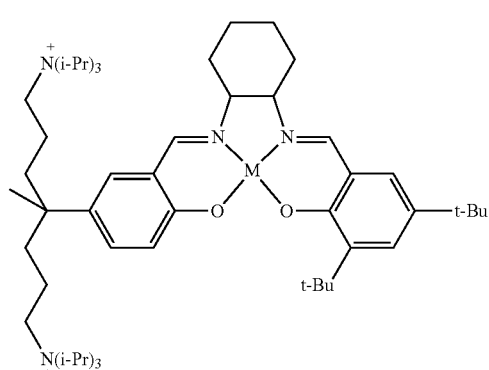
TABLE 1⊥-continued
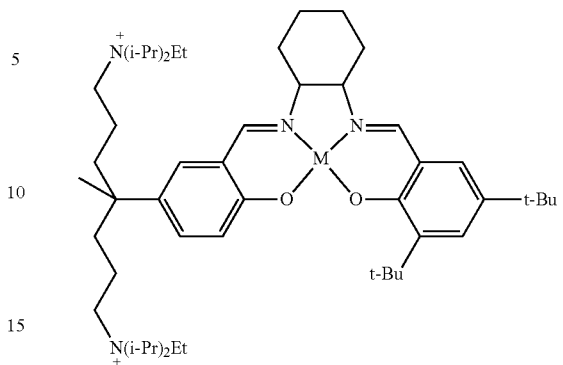
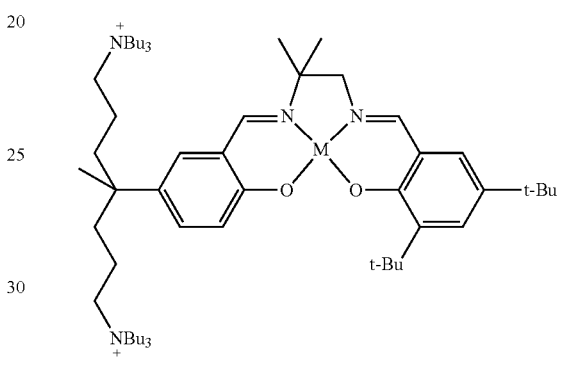
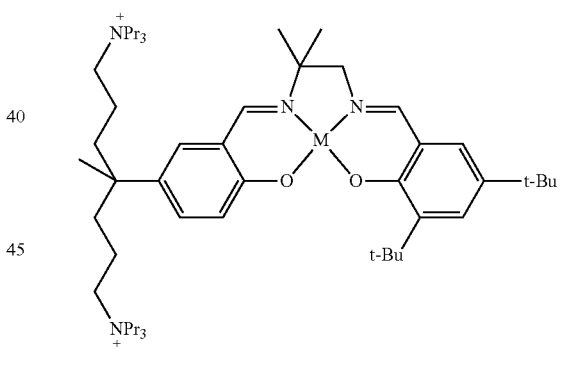
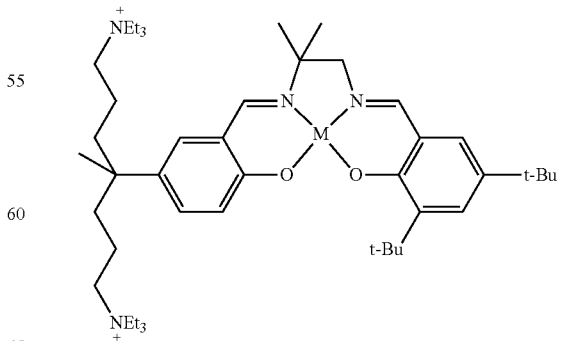

TABLE 1⊥-continued
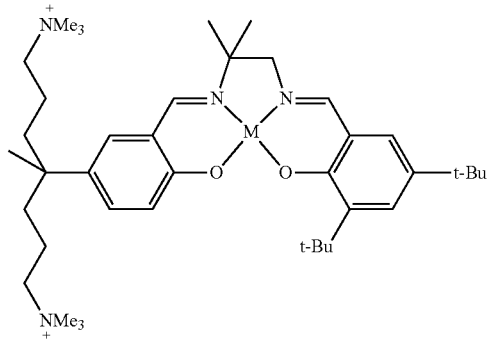
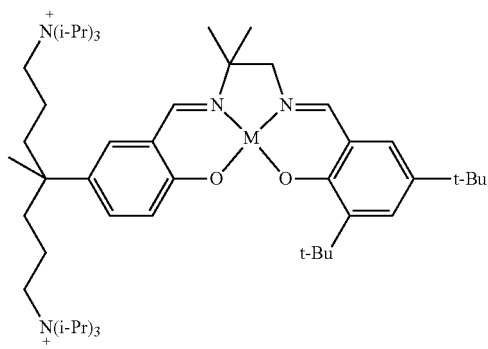
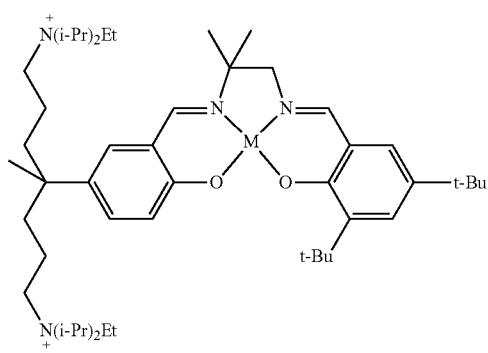
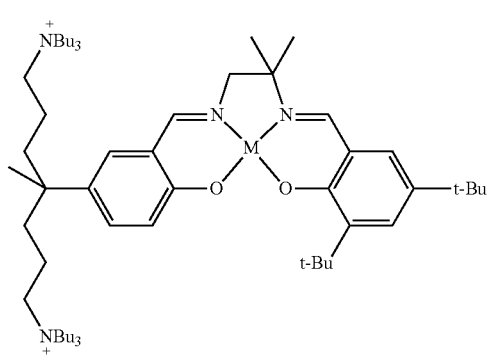
TABLE 1⊥-continued
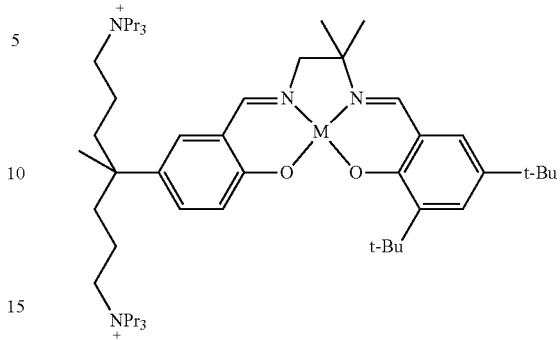
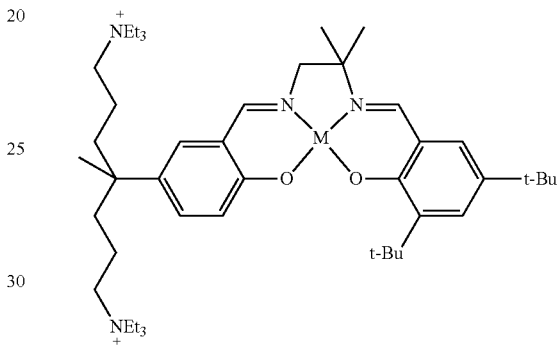
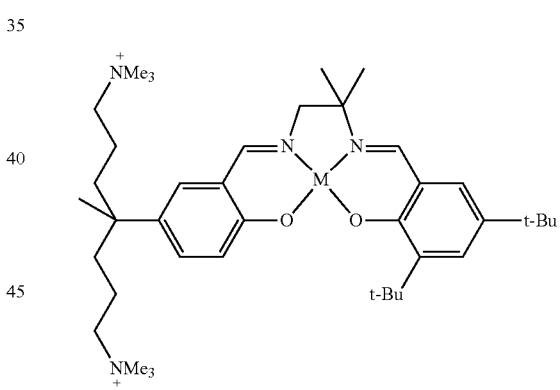
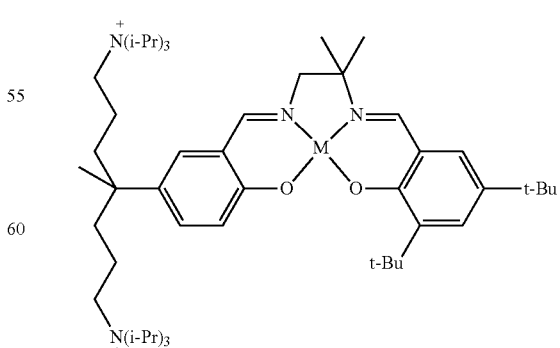

TABLE 1⊥-continued
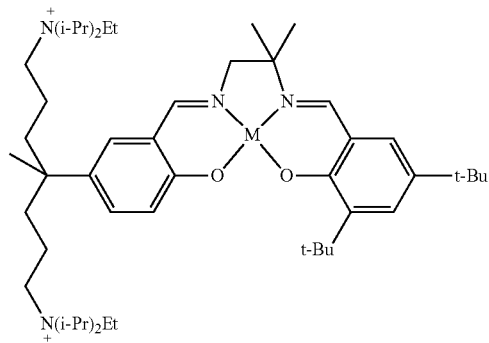
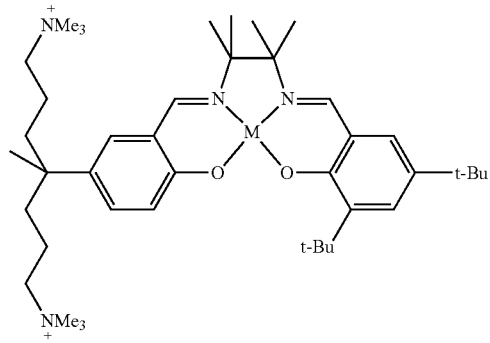
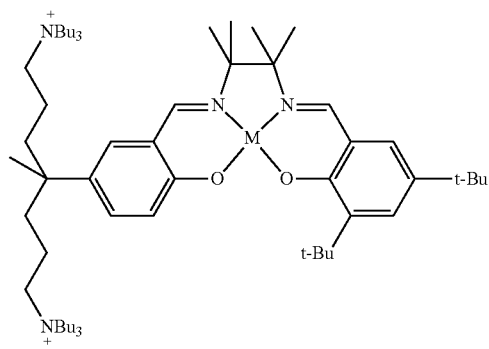
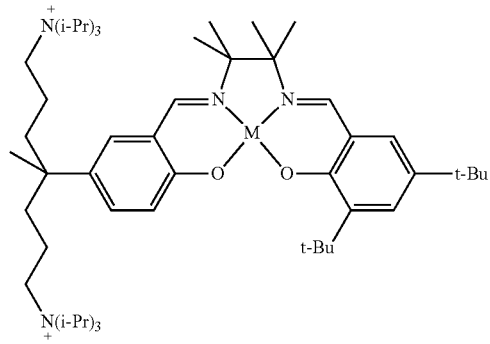
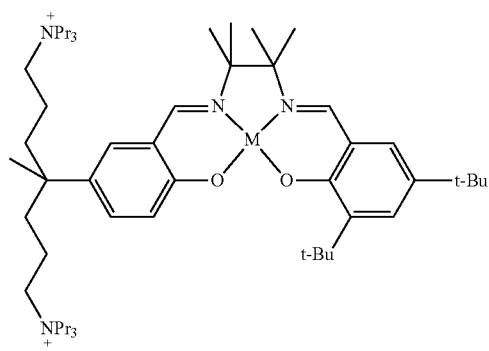
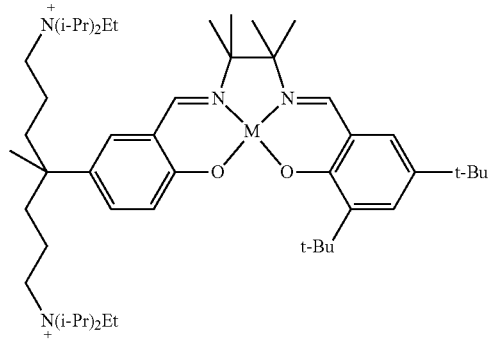
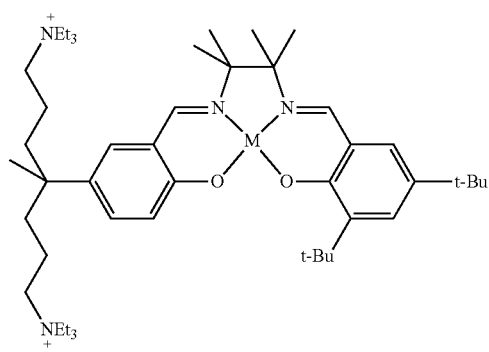
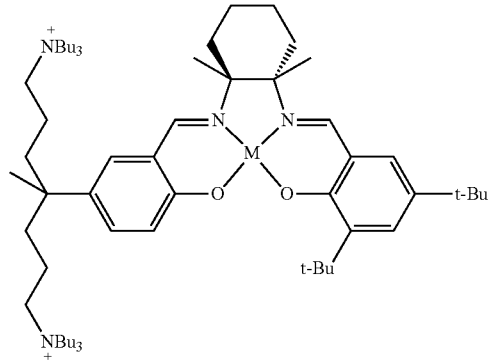

TABLE 1⊥-continued
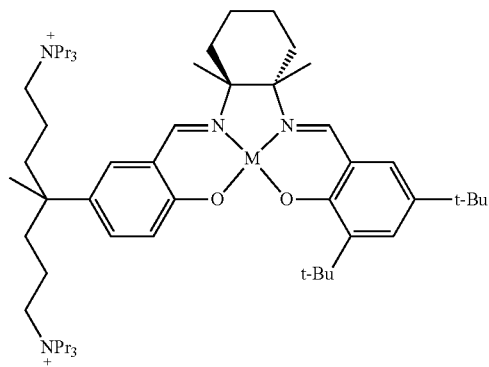
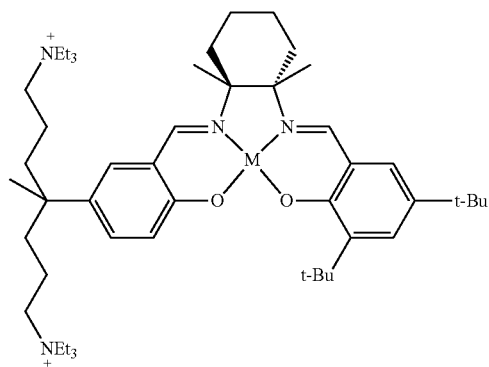
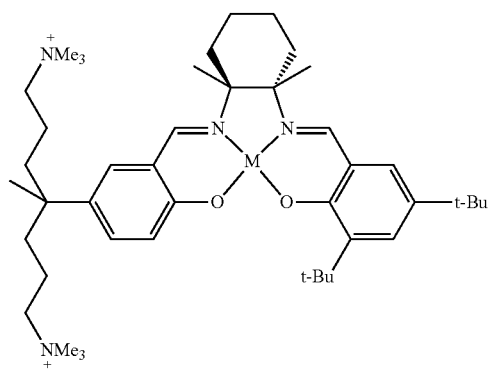
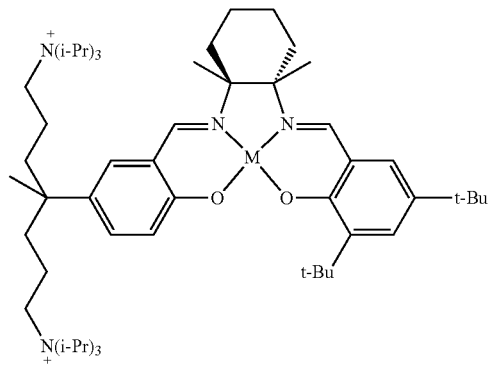
TABLE 1⊥-continued
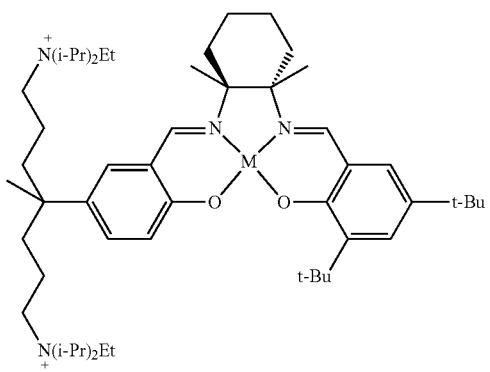
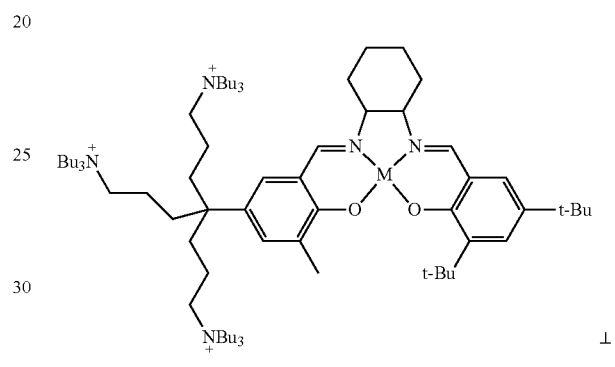
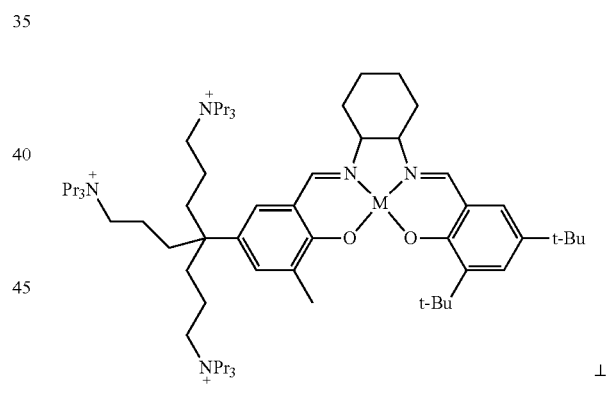
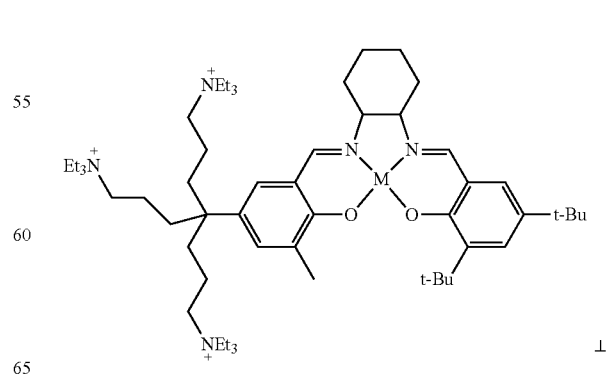

TABLE 1⊥-continued
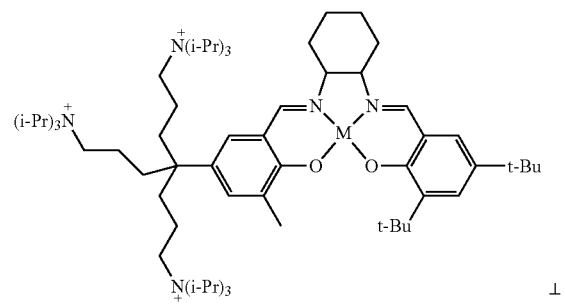
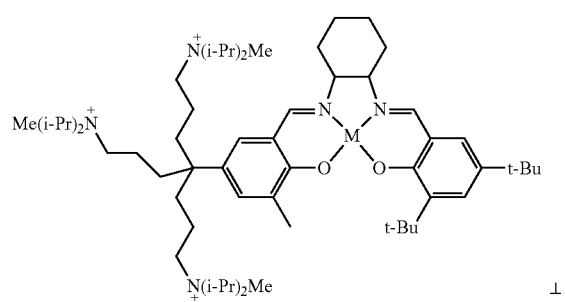
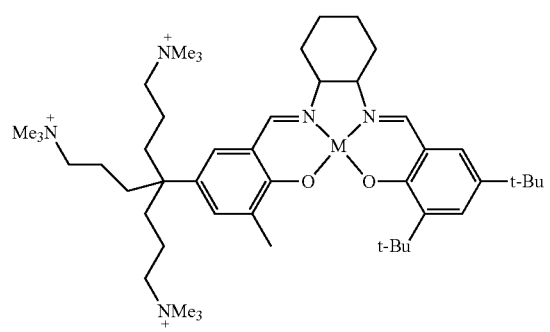
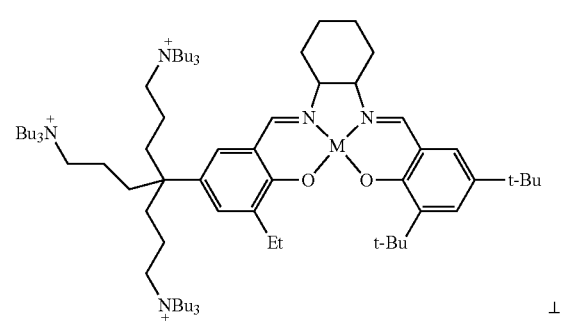
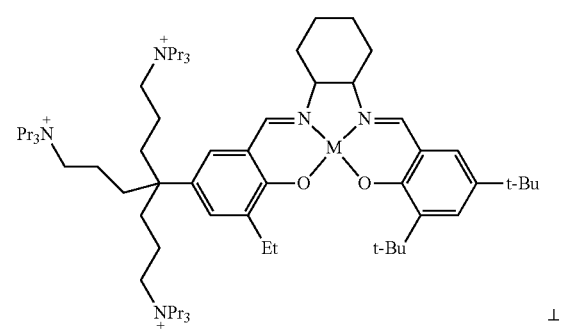
TABLE 1⊥-continued
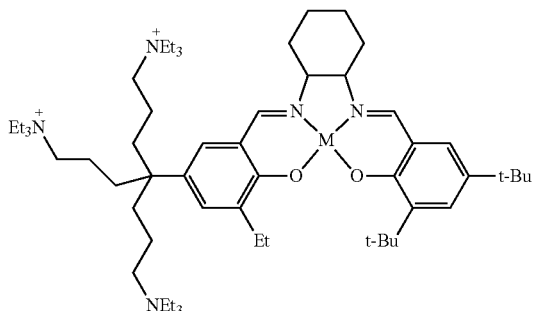
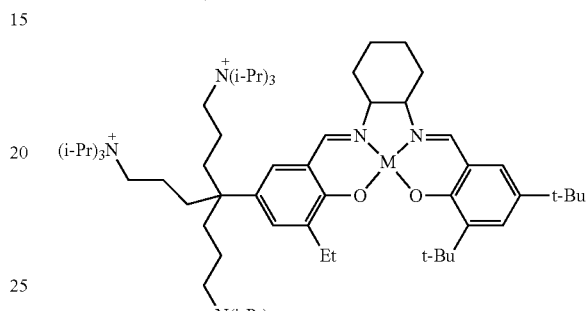
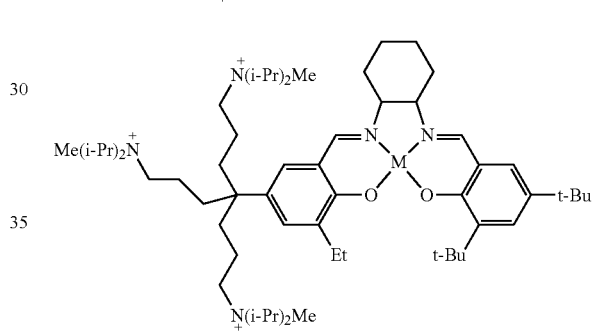
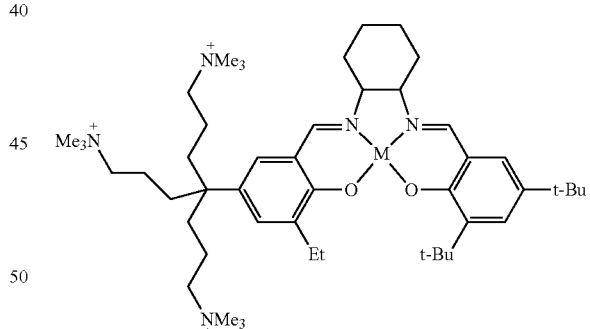
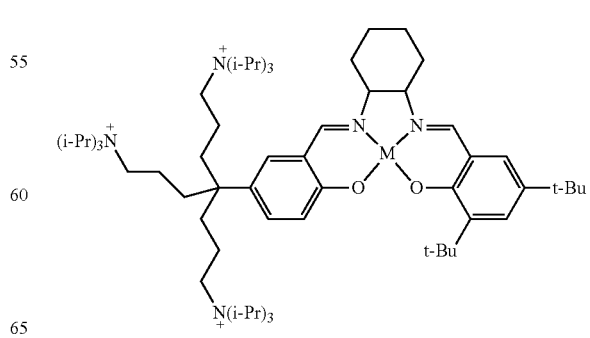

TABLE 1⊥-continued
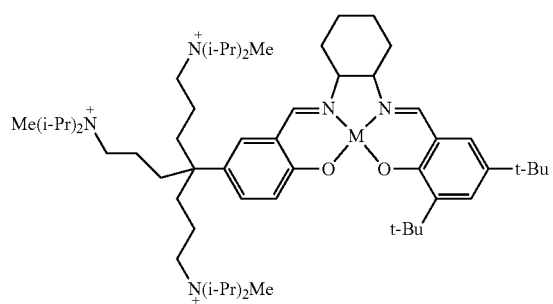
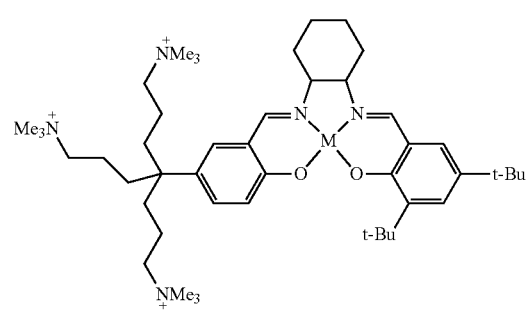
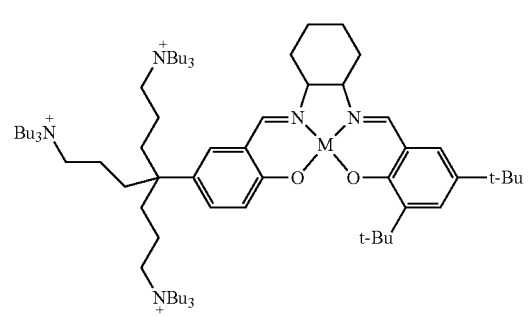
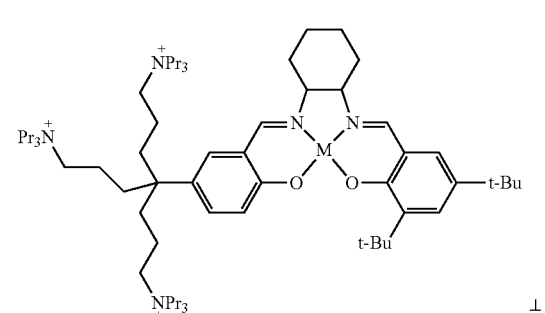
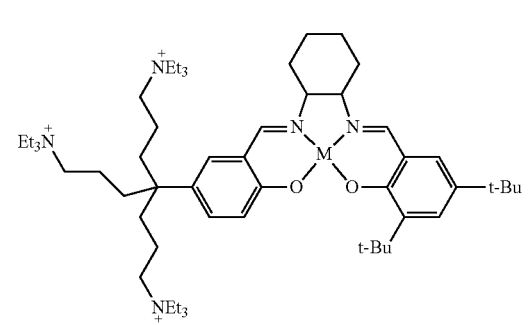
TABLE 1⊥-continued
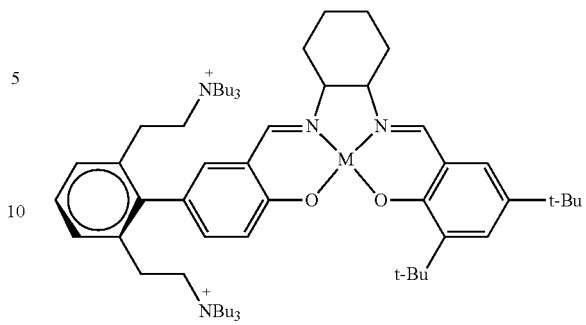
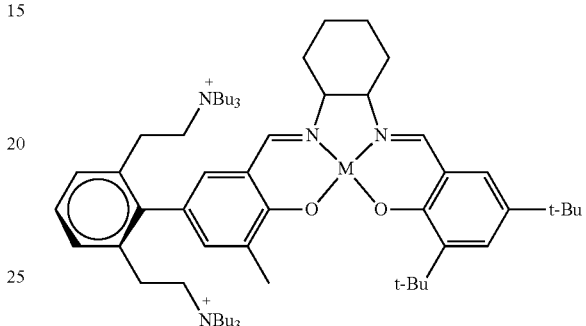
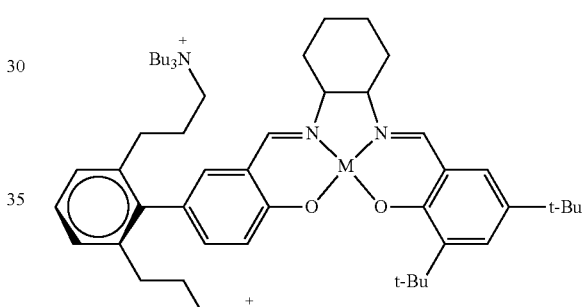
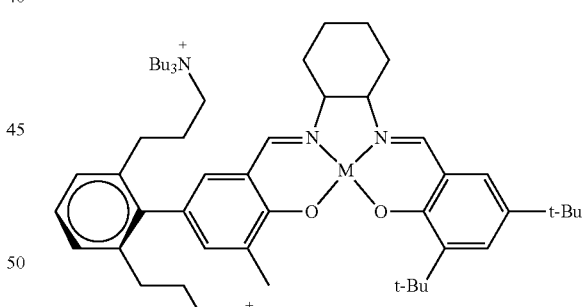
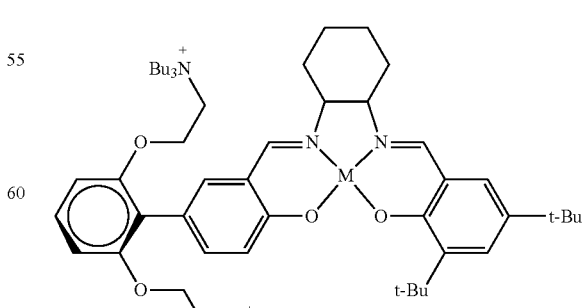

TABLE 1⊥-continued
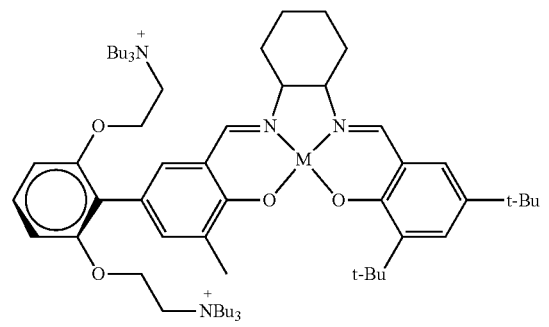
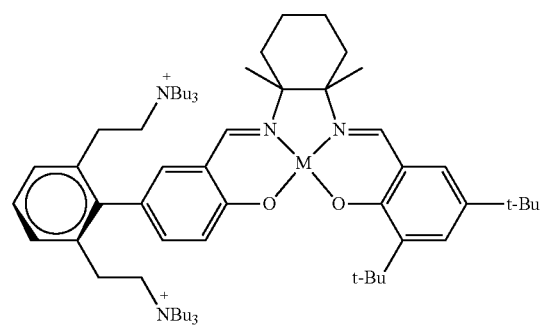
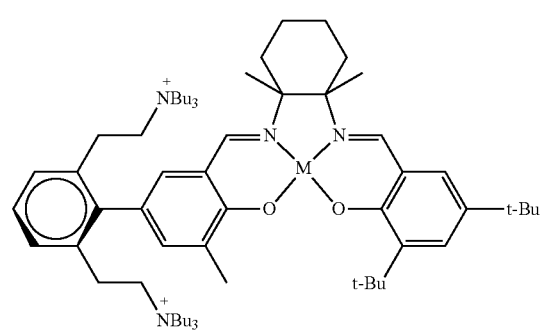
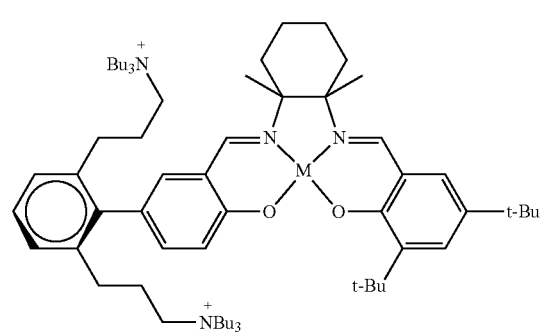
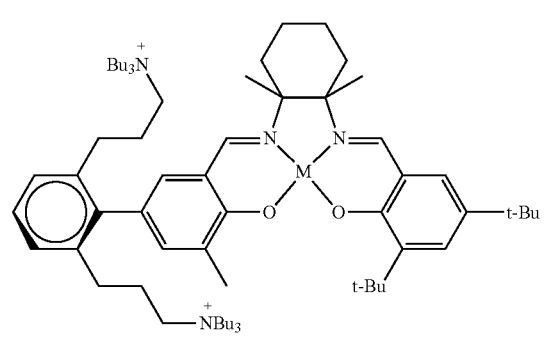
TABLE 1⊥-continued
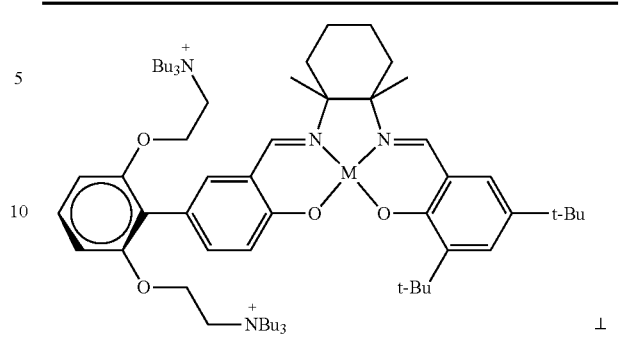
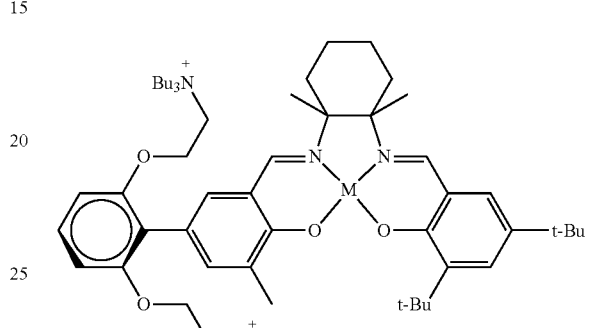
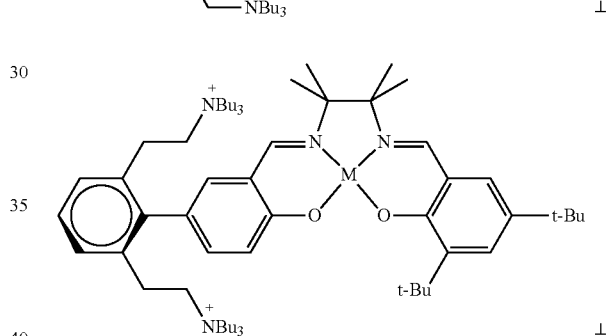
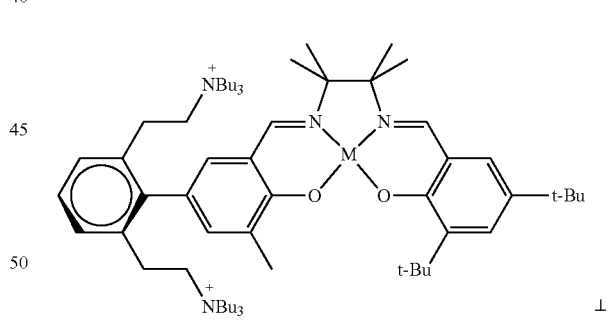
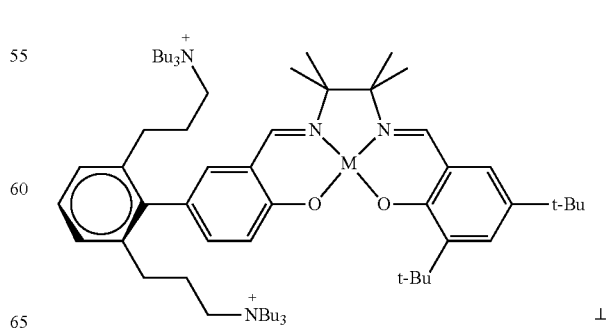

TABLE 1⊥-continued
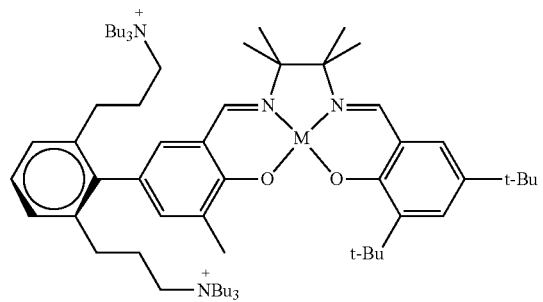
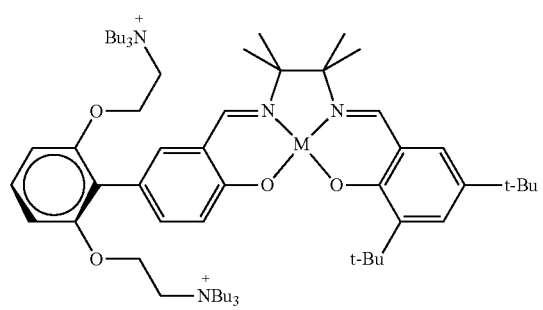
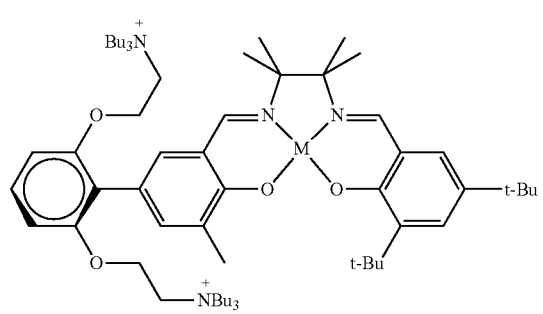
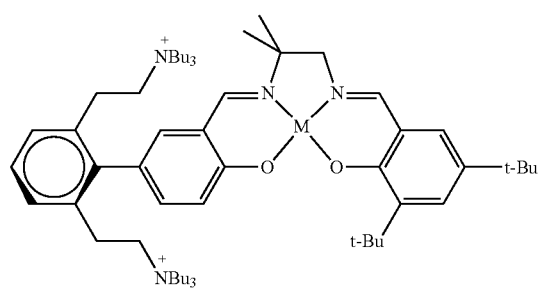
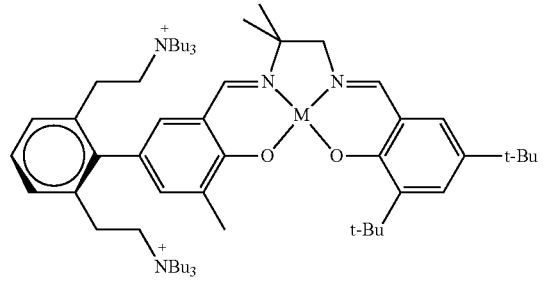
TABLE 1⊥-continued
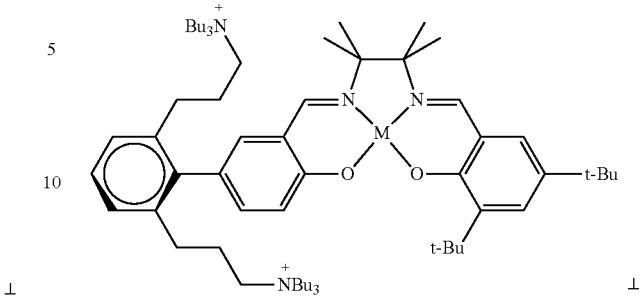
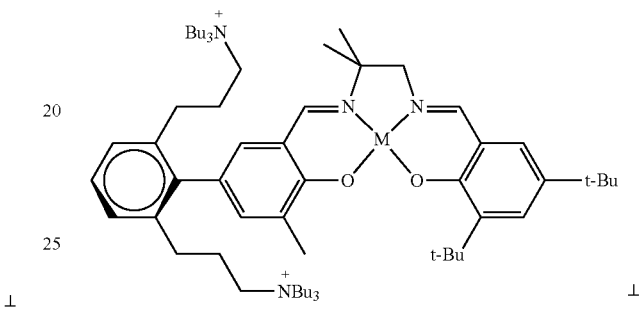
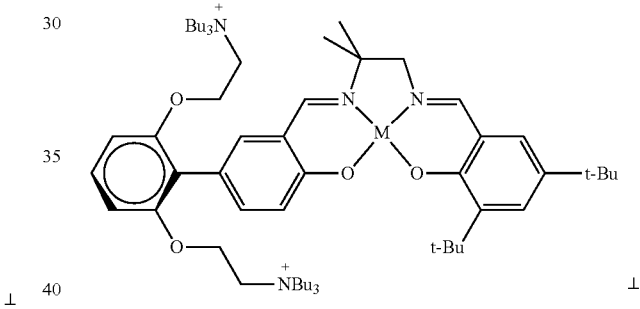
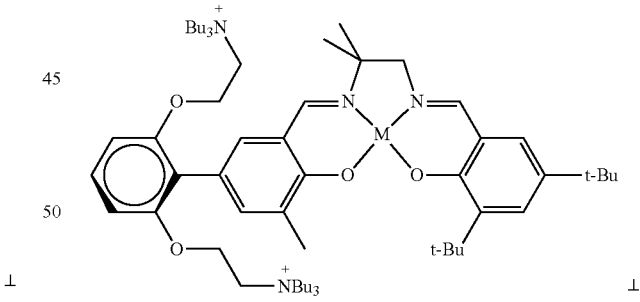
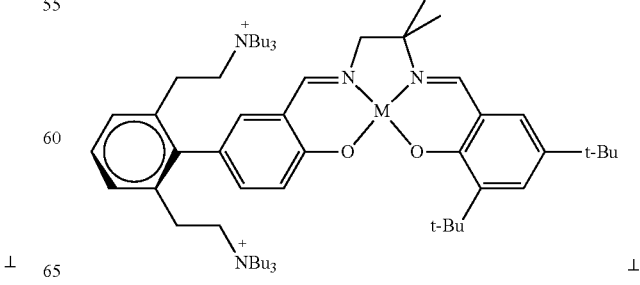

TABLE 1⊥-continued

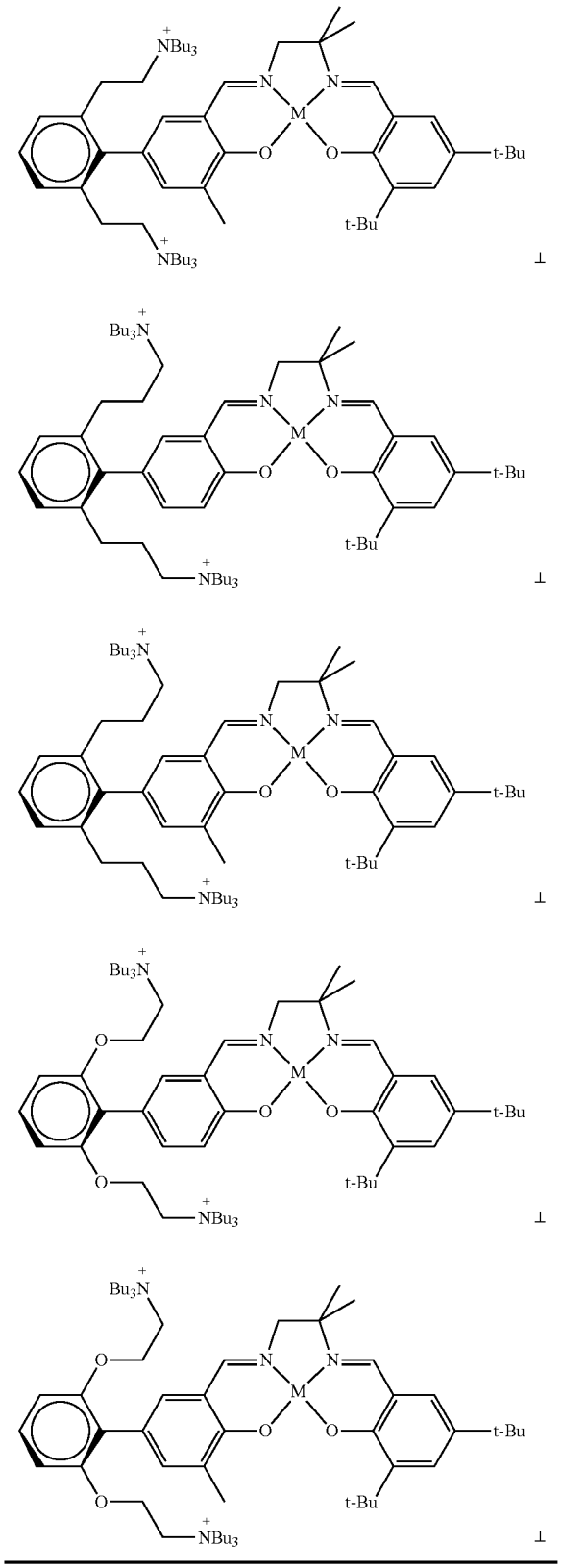

Metal Atoms

In certain embodiments, M is a metal atom selected from periodic table groups 3-13, inclusive. In certain embodiments, M is a transition metal selected from periodic table groups 5-12, inclusive. In certain embodiments, M is a transition metal selected from periodic table groups 4-11, inclusive. In certain embodiments, M is a transition metal selected from periodic table groups 5-10, inclusive. In certain embodiments, M is a transition metal selected from periodic table groups 7-9, inclusive. In some embodiments, M is selected from the group consisting of Cr, Mn, V, Fe, Co, Mo, W, Ru, Al, and Ni. In some embodiments, M is a metal atom selected from the group consisting of: cobalt; chromium; aluminum; titanium; ruthenium, and manganese. In some embodiments, M is cobalt. In some embodiments, M is chromium. In some embodiments, M is aluminum.

In certain embodiments, a metal complex is a zinc, cobalt, chromium, aluminum, titanium, ruthenium, or manganese complex. In certain embodiments, a metal complex is an aluminum complex. In some embodiments, a metal complex is a chromium complex. In some embodiments, a metal complex is a zinc complex. In certain some embodiments, a metal complex is a titanium complex. In some embodiments, a metal complex is a ruthenium complex. In certain embodiments, a metal complex is a manganese complex. In certain embodiments, a metal complex is cobalt complex. In certain embodiments where the metal complex is a cobalt complex, the cobalt metal has an oxidation state of 3+ (i.e., Co(III)). In some embodiments, the cobalt metal has an oxidation state of 2+.

In certain embodiments, at least one activating moiety is tethered to a carbon atom of one phenyl ring of the salicylaldehyde-derived portions of a salen ligand. In certain embodiments, at least one activating moiety is tethered to one or more carbon atoms of only one phenyl ring of the salicylaldehyde-derived portions of a salen ligand, as shown in formula I:

In certain embodiments, for complexes of Table 1, M is Co—X, where X is as defined above and described in classes and subclasses herein. In certain embodiments, for complexes of Table 1, M is Co—OC(O)CF$_3$. In certain embodiments, for complexes of Table 1, M is Co—OAc. In certain embodiments, for complexes of Table 1, M is Co—OC(O)C$_6$F$_5$. In certain embodiments, for complexes of Table 1, M is Co—N$_3$. In certain embodiments, for complexes of Table 1, M is Co—NO$_3$. In certain embodiments, for complexes of Table 1, M is Co—Cl. In certain embodiments, for complexes of Table 1, M is Co-nitrophenoxy. In certain embodiments, for complexes of Table 1, M is Co-dinitrophenoxy.

In some embodiments, for complexes of Table 1, M is Cr—X, where X is as defined above and described in classes and subclasses herein.

Polymerization Methods

In another aspect, the present invention provides methods of making aliphatic polycarbonates. In certain embodiments, the methods comprise contacting one or more epoxides with CO$_2$ in the presence of any of the metal complexes described hereinabove.

In some embodiments, the present invention provides a method of polymerization, the method comprising:

a) providing an epoxide of formula:

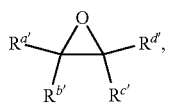

wherein:

$R^{a\prime}$ is hydrogen or an optionally substituted radical selected from the group consisting of $C_{1-30}$ aliphatic; $C_{1-30}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; and each of $R^{b\prime}$, $R^{c\prime}$, and $R^{d\prime}$ is independently hydrogen or an optionally substituted radical selected from the group consisting of $C_{1-12}$ aliphatic; $C_{1-12}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur;

wherein any of ($R^{a\prime}$ and $R^{c\prime}$), ($R^{c\prime}$ and $R^{d\prime}$), and ($R^{a\prime}$ and $R^{b\prime}$) can be taken together with intervening atoms to form one or more optionally substituted rings;

b) contacting the epoxide and carbon dioxide in the presence of a metal complex as described herein to provide a polymer having a formula selected from the group consisting of:

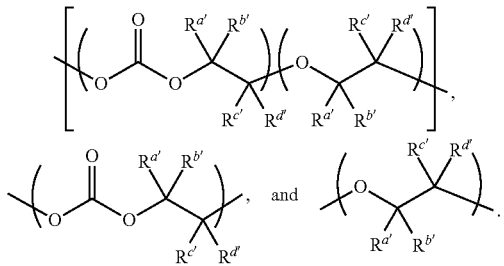

In some embodiments, a provided polymer has a formula:

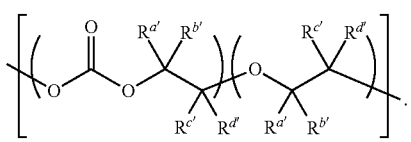

In some embodiments, a provided polymer has a formula:

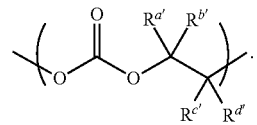

In some embodiments, carbon dioxide is optional and a provided polymer has a formula:

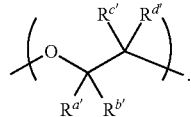

In some embodiments, the epoxide is ethylene oxide, propylene oxide, butylene oxide, cyclohexene oxide, or mixtures of any of these. In some embodiments, the epoxide is propylene oxide. In some embodiments, the epoxide is ethylene oxide. In some embodiments, the epoxide is a mixture of propylene oxide with one or more of ethylene oxide, cyclohexene oxide, and butylene oxide. In certain embodiments, the epoxide is a mixture of ethylene oxide and propylene oxide. In some embodiments, the epoxide is a mixture of propylene oxide and cyclohexene oxide.

In certain embodiments, $R^{b\prime}$, $R^{c\prime}$, and $R^{d\prime}$ are each hydrogen. In some embodiments, $R^{a\prime}$ is optionally substituted $C_{1-12}$ aliphatic. In some embodiments, $R^{a\prime}$ is optionally substituted $C_{1-12}$ heteroaliphatic.

In certain embodiments, one of $R^{a\prime}$, $R^{b\prime}$, $R^{c\prime}$, and $R^{d\prime}$ is hydrogen. In certain embodiments, two of $R^{a\prime}$, $R^{b\prime}$, $R^{c\prime}$, and $R^{d\prime}$ are hydrogen. In certain embodiments, three of $R^{a\prime}$, $R^{b\prime}$, $R^{c\prime}$, and $R^{d\prime}$ are hydrogen.

In certain embodiments, $R^{a\prime}$ is hydrogen. In certain embodiments, $R^{b\prime}$ is hydrogen. In certain embodiments, $R^{c\prime}$ is hydrogen. In certain embodiments, $R^{d\prime}$ is hydrogen.

In certain embodiments, $R^{a\prime}$, $R^{b\prime}$, $R^{c\prime}$, and $R^{d\prime}$ are each independently an optionally substituted $C_{1-30}$ aliphatic group. In certain embodiments, $R^{a\prime}$, $R^{b\prime}$, $R^{c\prime}$, and $R^{d\prime}$ are each independently an optionally substituted $C_1$-20 aliphatic group. In certain embodiments, $R^{a\prime}$, $R^{b\prime}$, $R^{c\prime}$, and $R^{d\prime}$ are each independently an optionally substituted $C_{1-12}$ aliphatic group. In certain embodiments, $R^{a\prime}$, $R^{b\prime}$, $R^{c\prime}$, and $R^{d\prime}$ are each independently an optionally substituted $C_{1-8}$ aliphatic group. In certain embodiments, $R^{a\prime}$, $R^{b\prime}$, $R^{c\prime}$, and $R^{d\prime}$ are each independently an optionally substituted $C_{3-8}$ aliphatic group. In certain embodiments, $R^{a\prime}$, $R^{b\prime}$, $R^{c\prime}$, and $R^{d\infty 0}$ are each independently an optionally substituted $C_{3-12}$ aliphatic group.

In certain embodiments, $R^{a\prime}$ is an optionally substituted $C_{1-30}$ aliphatic group. In certain embodiments, $R^{b\prime}$ is an optionally substituted $C_{1-30}$ aliphatic group. In certain embodiments, $R^{c\prime}$ is an optionally substituted $C_{1-30}$ aliphatic group. In certain embodiments, $R^{d\prime}$ is an optionally substituted $C_{1-30}$ aliphatic group.

In some embodiments, an $R^{a\prime}$ and an $R^{b\prime}$ attached to the same carbon are taken together to form one or more optionally substituted 3-12-membered carbocyclic rings. In some embodiments, an $R^{a\prime}$ and an $R^{b\prime}$ attached to the same carbon are taken together to form a polycyclic carbocycle comprising two or more optionally substituted 3-8-membered carbocyclic rings. In some embodiments, an $R^{a\prime}$ and an $R^{b\prime}$ attached to the same carbon are taken together to form a polycyclic carbocycle comprising two or more optionally substituted 5-7-membered carbocyclic rings.

In some embodiments, an $R^{a'}$ and an $R^{b'}$ attached to the same carbon are taken together to form a bicyclic carbocycle comprising two optionally substituted 3-12-membered carbocyclic rings. In some embodiments, an $R^{a'}$ and an $R^{b'}$ attached to the same carbon are taken together to form a bicyclic carbocycle comprising two optionally substituted 3-8-membered carbocyclic rings. In some embodiments, an $R^{a'}$ and an $R^{b'}$ attached to the same carbon are taken together to form a bicyclic carbocycle comprising two optionally substituted 5-7-membered carbocyclic rings.

In certain embodiments, an $R^{a'}$ and an $R^{b'}$ attached to the same carbon are taken together to form an optionally substituted 3-12-membered carbocyclic ring. In certain embodiments, an $R^{a'}$ and an $R^{b'}$ attached to the same carbon are taken together to form an optionally substituted 3-8-membered carbocyclic ring. In certain embodiments, an $R^{a'}$ and an $R^{b'}$ attached to the same carbon are taken together to form an optionally substituted 5-7-membered carbocyclic ring.

In some embodiments, an $R^{b'}$ and an $R^{c'}$ attached to adjacent carbons are taken together to form one or more optionally substituted 3-12-membered carbocyclic rings. In some embodiments, an $R^{b'}$ and an $R^{c'}$ attached to adjacent carbons are taken together to form a polycyclic carbocycle comprising two or more optionally substituted 3-8-membered carbocyclic rings. In some embodiments, an $R^{b'}$ and an $R^{c'}$ attached to adjacent carbons are taken together to form a polycyclic carbocycle comprising two or more optionally substituted 5-7-membered carbocyclic rings.

In some embodiments, an $R^{b'}$ and an $R^{c'}$ attached to adjacent carbons are taken together to form a bicyclic carbocycle comprising two optionally substituted 3-12-membered carbocyclic rings. In some embodiments, an $R^{b'}$ and an $R^{c'}$ attached to adjacent carbons are taken together to form a bicyclic carbocycle comprising two optionally substituted 3-8-membered carbocyclic rings. In some embodiments, an $R^{b'}$ and an $R^{c'}$ attached to adjacent carbons are taken together to form a bicyclic carbocycle comprising two optionally substituted 5-7-membered carbocyclic rings.

In certain embodiments, an $R^{b'}$ and an $R^{c'}$ attached to adjacent carbons are taken together to form an optionally substituted 3-12-membered carbocyclic ring. In certain embodiments, an $R^{b'}$ and an $R^{c'}$ attached to adjacent carbons are taken together to form an optionally substituted 3-8-membered carbocyclic ring. In certain embodiments, an $R^{b'}$ and an $R^{c'}$ attached to adjacent carbons are taken together to form an optionally substituted 5-7-membered carbocyclic ring.

In certain embodiments, the polymer comprises a copolymer of two different repeating units where $R^{a'}$, $R^{b'}$, and $R^{c'}$ the two different repeating units are not all the same. In some embodiments, a polymer comprises a copolymer of three or more different repeating units wherein $R^{a'}$, $R^{b'}$, and $R^{c'}$ of each of the different repeating units are not all the same as $R^{a'}$, $R^{b'}$, and $R^{c'}$ of any of the other different repeating units. In some embodiments, a polymer is a random copolymer. In some embodiments, a polymer is a tapered copolymer.

In some embodiments, a polymer contains a metal complex as described herein. In some embodiments, a polymer comprises residue of a metal complex as described herein. In some embodiments, a polymer comprises a salt of an organic cation and X, wherein X is a nucleophile or counterion. In some embodiments, X is 2,4-dinitrophenolate anion.

In some embodiments, $R^{a'}$ is optionally substituted $C_{1-12}$ aliphatic. In some embodiments, $R^{a'}$ is optionally substituted $C_{1-12}$ heteroaliphatic. In some embodiments, $R^{a'}$ is optionally substituted phenyl. In some embodiments, $R^{a'}$ is optionally substituted 8- to 10-membered aryl. In some embodiments, le is optionally substituted 5- to 10-membered heteroaryl. In some embodiments, $R^{a'}$ is optionally substituted 3- to 7-membered heterocyclic.

In certain embodiments, $R^{a'}$ is selected from methyl, ethyl, propyl, butyl, vinyl, allyl, phenyl, trifluoromethyl,

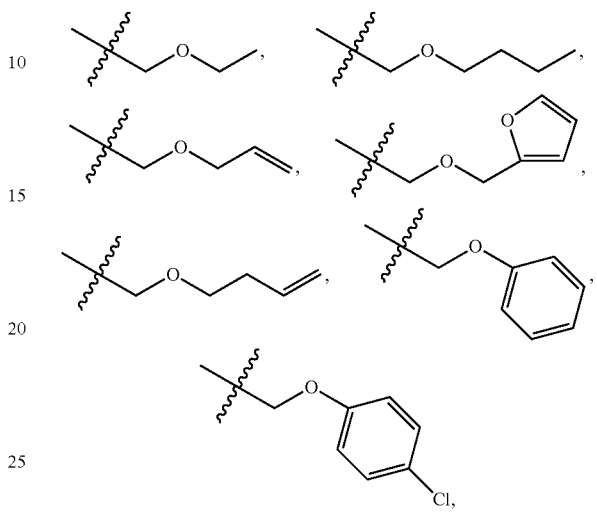

or any two or more of the above. In certain embodiments, $R^{a'}$ is methyl. In certain embodiments, $R^{a'}$ is ethyl. In certain embodiments, $R^{a'}$ is propyl. In certain embodiments, le is butyl. In certain embodiments, $R^{a'}$ is vinyl. In certain embodiments, $R^{a'}$ is allyl. In certain embodiments, $R^{a'}$ is phenyl. In certain embodiments, $R^{a'}$ is trifluoromethyl. In certain embodiments, $R^{a'}$ is

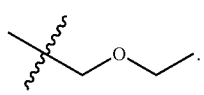 [SMILES: *COCC]

In certain embodiments, $R^{a'}$ is

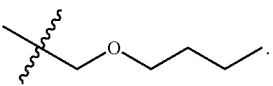 [SMILES: *COCCCC]

In certain embodiments, $R^{a'}$ is

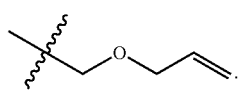 [SMILES: *COCC=C]

In certain embodiments, $R^{a'}$ is

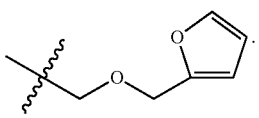 [SMILES: *COCc1ccco1]

In certain embodiments, $R^{a'}$ is

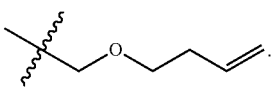

In certain embodiments, $R^{a'}$ is

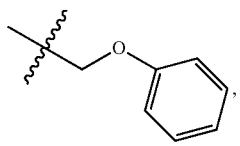 [SMILES: *COc1ccccc1]

In certain embodiments, $R^{a'}$ is

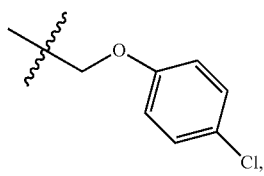 [SMILES: *COc1ccc(Cl)cc1]

In some embodiments, $R^{b'}$ is hydrogen. In some embodiments, $R^{b'}$ is optionally substituted $C_{1-12}$ aliphatic. In some embodiments, $R^{b'}$ is optionally substituted $C_{1-12}$ heteroaliphatic. In some embodiments, $R^{b'}$ is optionally substituted phenyl. In some embodiments, $R^{b'}$ is optionally substituted 8- to 10-membered aryl. In some embodiments, $R^{b'}$ is optionally substituted 5- to 10-membered heteroaryl. In some embodiments, $R^{b'}$ is optionally substituted 3- to 7-membered heterocyclic.

In some embodiments, $R^{c'}$ is hydrogen. In some embodiments, $R^{c'}$ is optionally substituted $C_{1-12}$ aliphatic. In some embodiments, $R^{c'}$ is optionally substituted $C_{1-12}$ heteroaliphatic. In some embodiments, $R^{c'}$ is optionally substituted phenyl. In some embodiments, $R^{c'}$ is optionally substituted 8- to 10-membered aryl. In some embodiments, $R^{c'}$ is optionally substituted 5- to 10-membered heteroaryl. In some embodiments, $R^{c'}$ is optionally substituted 3- to 7-membered heterocyclic.

In some embodiments, $R^{a'}$ and $R^{c'}$ are taken together with intervening atoms to form one or more rings selected from the group consisting of: optionally substituted $C_3$-$C_{14}$ carbocycle, optionally substituted 3- to 14-membered heterocycle, optionally substituted phenyl, optionally substituted $C_8$-$C_{10}$ aryl, and optionally substituted 5- to 10-membered heteroaryl.

In some embodiments, le and $R^{c'}$ are taken together with intervening atoms to form one or more rings selected from the group consisting of: optionally substituted $C_3$-$C_{14}$ carbocycle, optionally substituted 3- to 14-membered heterocycle, optionally substituted phenyl, optionally substituted $C_8$-$C_{10}$ aryl, and optionally substituted 5- to 10-membered heteroaryl.

In some embodiments, $R^{a'}$ and $R^{b'}$ are taken together with intervening atoms to form one or more rings selected from the group consisting of: optionally substituted $C_3$-$C_{14}$ carbocycle, optionally substituted 3- to 14-membered heterocycle, optionally substituted phenyl, optionally substituted $C_8$-$C_{10}$ aryl, and optionally substituted 5- to 10-membered heteroaryl.

In some embodiments, the invention includes methods for synthesizing polyol compounds from epoxides. Suitable methods of performing these reactions are disclosed in co-owned PCT Publication No. WO2010/028362 A1, the entire contents of which are hereby incorporated herein by reference.

In some embodiments, the invention includes methods for synthesizing polyethers from epoxides. Suitable methods of performing these reactions are disclosed in U.S. Pat. No. 7,399,822, the entire contents of which are hereby incorporated herein by reference.

In some embodiments, the invention includes methods for synthesizing cyclic carbonates from carbon dioxide and epoxides using complexes described above, suitable methods of performing this reaction are disclosed in U.S. Pat. No. 6,870,004 which is incorporated herein by reference.

EXAMPLES

Example 1

A typical route to asymmetric cobalt (III) cobalt complexes of the present invention is shown in Scheme E1:

Scheme E1

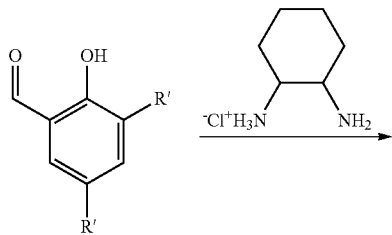

E1-b

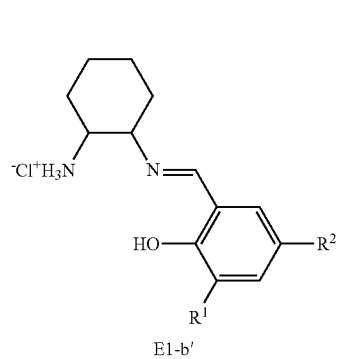 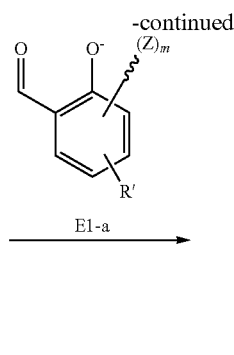 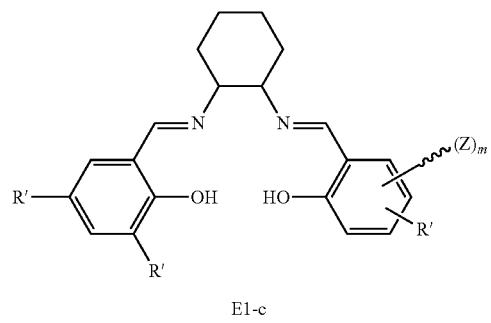

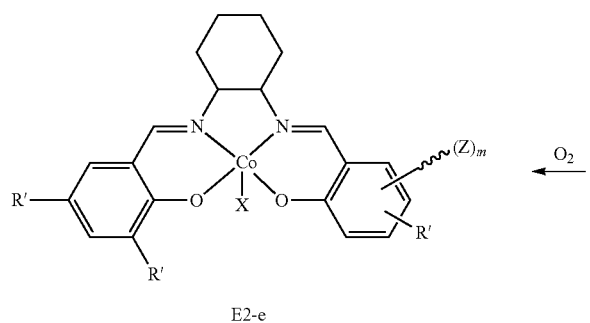 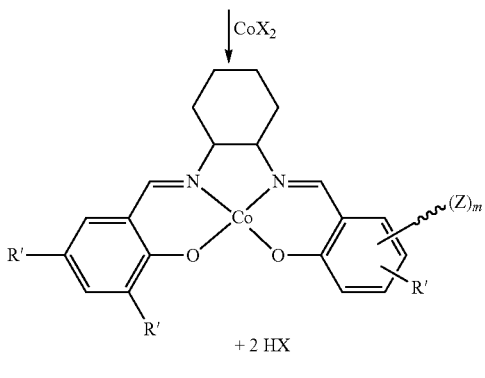

where R', ⁓⁓⁓ $(Z)_m$, and X are as defined above and described in classes and subclasses herein.

As shown in Scheme E1, disubstituted salicylaldehyde derivative E1-b is treated with one equivalent of a monohydrochloride salt of 1,2 cyclohexanediamine. The resulting Schiff base E-1b' is then contacted with the phenolate anion of a second salicylaldehyde compound E1-a. This provides ligand E1-c which is then treated with a cobalt salt and oxidized in the usual fashion to afford the cobalt III complex E2-e. As will be appreciated by the skilled artisan, numerous variations of the process shown in Scheme E1 are possible. In one variant of this process, an external base is added at the second step rather than relying on the phenolate salt to deprotonate the ammonium salt E-1b'. In another variant, an acid is added during the oxidation step such that the X group bound to the cobalt atom in the final catalyst is not the same as the counterion(s) present on the cobalt salt used in the preceding step. In another variant, the metal complex E2-e is treated in additional steps to change the identity of the anion X associated with the cobalt atom and/or those associated with the cationic Z groups. In another variant, the salicylaldehyde E1-a is reacted with the monohydrochloride salt of 1,2 cyclohexanediamine and salicylaldehyde E1-b is added in the subsequent step. In other variants, diamines other than cyclohexanediamine are utilized in the first step. In still other variants, chromium or other metal salts are substituted for the cobalt salt.

Numerous preparations of salicylaldehyde derivatives bearing cationic Z groups are known in the literature: examples include WO 2010/022388; WO 2008/136591, WO 2010/013948, WO 2011/105846 each of which is incorporated herein by reference. The compounds and/or methods disclosed in these references can be used to provide numerous compounds of formula E1-a suitable for the present invention, and any of these compounds can be utilized in the sequence shown in Scheme E1 to provide compounds of the present invention.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been presented by way of example.

What is claimed is:

1. A method for the synthesis of aliphatic polycarbonates comprising the step of contacting an epoxide and carbon dioxide with a metal complex comprising a metal atom coordinated with a salen ligand, the salen ligand comprising two halves, each half coordinated to the metal atom via an imine and an oxygen atom, wherein the metal complex is characterized in that one of the two halves of the salen ligand has two or more cationic activating functional groups tethered to it and the other half has no tethered cationic activating functional groups, wherein the half of the ligand having no tethered cationic activating functional groups comprises or is derived from a gamma dicarbonyl compound.

2. The method of claim 1, wherein the cationic activating functional groups tethered to the ligand are independently selected from the group consisting of: onium salts, nitrogen-containing functional groups; phosphorous-containing functional groups; and arsenic-containing functional groups.

3. The method of claim 1, wherein at least one cationic activating functional group comprises an ammonium salt.

4. The method of claim 1, wherein at least one cationic activating functional group is selected from the group consisting of amidinium salts and guanidinium salts.

5. The method of claim 1, wherein the gamma dicarbonyl compound comprises optionally substituted acetylacetone.

6. The method of claim 1, wherein the metal complex contains a total of 2 to 4 cationic activating functional groups.

7. The method of claim 6, wherein the metal complex contains a total of 2 cationic activating functional groups.

8. The method of claim 6, wherein the metal complex contains a total of 3 cationic activating functional groups.

9. The method of claim 6, wherein the metal complex contains a total of 4 cationic activating functional groups.

10. The method of claim 1, wherein the epoxide is selected from the group consisting of: ethylene oxide, propylene oxide, butylene oxide, cyclohexene oxide, 1,2 octene oxide, 3-vinyl cyclohexene oxide, epichlorohydrin and mixtures of any two or more of these.

11. The method of claim 10, wherein the epoxide is propylene oxide.

12. The method of claim 1, wherein the $CO_2$ pressure is between about 50 and 800 psi.

13. The method of claim 1, wherein a molar ratio of the metal complex to the epoxide is between about 1:1000 and about 1:100,000.

14. The method of claim 1, further comprising the steps of letting the polymerization proceed until a desired polymer molecular weight has been achieved, quenching the polymerization reaction and isolating the polymer.

\* \* \* \* \*